: US008350014B2

(12) United States Patent
Raines et al.

(10) Patent No.: US 8,350,014 B2
(45) Date of Patent: Jan. 8, 2013

(54) PREPARATION OF DIAZO AND DIAZONIUM COMPOUNDS

(75) Inventors: Ronald Thaddeus Raines, Madison, WI (US); Eddie Leonard Myers, Munich (DE)

(73) Assignee: Wisconsin Alumni Research Foundation, Madison, WI (US)

( * ) Notice: Subject to any disclaimer, the term of this patent is extended or adjusted under 35 U.S.C. 154(b) by 182 days.

(21) Appl. No.: 12/620,567

(22) Filed: Nov. 17, 2009

(65) Prior Publication Data

US 2010/0125132 A1 May 20, 2010

Related U.S. Application Data

(60) Provisional application No. 61/115,474, filed on Nov. 17, 2008.

(51) Int. Cl.
*C07C 245/14* (2006.01)
*C07C 245/20* (2006.01)
*C07C 245/24* (2006.01)

(52) U.S. Cl. .................................. 534/555; 534/565
(58) Field of Classification Search .................. None
See application file for complete search history.

(56) References Cited

U.S. PATENT DOCUMENTS

| 6,972,320 | B2 | 12/2005 | Raines et al. |
| 6,974,884 | B2 | 12/2005 | Raines et al. |
| 7,256,256 | B1 | 8/2007 | Paterson et al. |
| 7,317,129 | B2 | 1/2008 | Raines et al. |
| 7,939,626 | B2 | 5/2011 | Saxon et al. |
| 2007/0037964 | A1 | 2/2007 | Saxon et al. |
| 2008/0274057 | A1 | 11/2008 | Robillard et al. |

FOREIGN PATENT DOCUMENTS

WO WO 2010/057220 5/2010

OTHER PUBLICATIONS

Dube, Daniele Hilda, "Probing Glycosylation Using Azidosugars and the Staudinger Ligation in vivo", Avail. UMI, Order No. DA3210568. (2005), 160 pp. From: Diss Abstr. Int. B 2006, 67(4), 2005.*
Baumgarten, R.J. (Feb. 1967) "The Preparation of Ethyl Diaxoacetate via a Triazene Intermediate," *J. Org. Chem.* 32:484-485.
Benati et al. (Jan. 1997) "Diazo Transfer Reactions of Tosyl Azide with Carbocyclic Beta-Keto Esters: 14-16,33,34-35 Production and Decomposition of Ring-Opened N-Tosylcarbamoylsubstituled Alpha-Diazo Esters," *J. Chem. Soc. Perkin Trans.* 1(4):457-461.
Charafeddine et al. (2007) "First Synthesis of 2'-Deoxyfluoropuromycin Analogues: Experimental Insight into the Mechanism of the Staudinger Reaction," *Chem. Eur. J.* 13:5566-5584.
Fresneda et al. (2004) "Application of Iminophosphorane-Based Methodologies for the Synthesis of Natural Products," *SynLett.* : 1197-1218.
Froyen (Apr. 1994) "One-Flask Synthesis of Acyl Azides from Carboxylic Acids; A Facile Route to Iminophosphoranes," *Phosphorus, Sulfur, and Silicon and the Related Elements* 89(1-4).
International Search Report and Written Opinion, Corresponding to International Application PCT/US09/64874, Mailed Feb. 25, 2010.
International Preliminary Report on Patentability, Corresponding to International Application PCT/US09/64874, Mailed May 26, 2011.
Kelly et al. (Jan. 1982) "Substituent Effects on Tautomerisation Constants of Alkylaryltriazenes," *J. Chem. Soc., Perkin Trans.* 21982:1649-1654.
Köhn, et al. (2004) "The Staudinger Ligation—A Gift to Chemical Biology," *Angew. Chem. Int. Ed.* 43:3106-3116.
Lin et al. (2005) "Mechanistic Investigation of the Staudinger Ligation," *J. Am. Chem. Soc.* 127(8):2686-2695.
Liu et al. (Web Release Oct. 21, 2004) "An Investigation of Staudinger Reactions Involving cis-1,3,5-Triazidocyclohexane and Tri(alkylamino)phosphines," *Inorg. Chem.* 43(23):7431-7440.
Mizuno et al. (1999) "A Simple Method for the Synthesis of $N^\beta$-Glycosylated-Asparagine and -Glutamine Derivatives," *Synthesis* (1)162-165.
Molina et al. (1996) "Unexpected Staudinger Reaction of α-Phenyl Substituted with Triphenylphosphone. Preparation, X-Ray Crystal and Molecular Structures of a Phosphaxine, and Aminophosphonium Carbanion Salt and a Phosphazide, with (Z)-Configuration," *Tetrahedron* 52(28):9629-9642.
Myers et al. (Mar. 2009) "A Phosphine-Mediated Conversion of Azides to Diazo-Compounds," *Angew. Chem. Int Ed. Engl.* 48(13):2359-2363.
Nilsson et al. (Web Release Jun. 9, 2000) "Staudinger Ligation: A Peptide from a Thioester and Azide," *Org. Lett.* 2(13):1939-1941.
Oddo et al. (1936) "Über AcylTriazene; ein besonders schoner Fall von mesohydrischer Isomerie," *Ber. Dtsch. Chern. Ges. B* 69B:279-282. Restituyo et al. (Web Release Oct. 17, 2003) "Conversion of Aryl Azides to O-Alkyl Imidates via Modified Staudinger Ligation," *Org. Lett.* 5(23):4357-4360.
Saxon et al. (Mar. 17, 2000)"Cell Surface Engineering by a Modified Staudinger Reaction," *Science* 287:2007-2010.
Schroen et al. (Web Release Nov. 2, 2005) "Polymer-Bound Diazonium Salts for the Synthesis of Diaxoacetic Esters," *Tetrahedron* 61:12186-12192.
Shalev et al. (Mar. 8, 1996) "Sequence of Reactant Combination Alters the Course of the Staudinger Reaction of Azides with Acyl Derivatives Bimanes. 30." *J. Org. Chem.* 61(5):1689-1701.
Velasco et al. (2000) "Isolation, Reactivity and Intermolecular Trapping of Phosphazide Intermediates in the Staudinger Reaction of Tertiary Phosphones with Azides," *Tetrahedron* 56:4079-4084.
Wamhoff et al. (1995) "Iminophosphoranes: Versatile Tools in Heterocyclic Synthesis," *Adv. Heterocycl. Chem.* 33:159-249.

* cited by examiner

*Primary Examiner* — Fiona T Powers
(74) *Attorney, Agent, or Firm* — Greenlee Sullivan P.C.

(57) ABSTRACT

A method for making diazo-compounds, diazonium salts thereof and other protected forms of these compounds. Diaz-compounds are prepared by reaction of a tertiary phosphine reagent carrying a reactive carbonyl group with an azide. The reaction can also generate an acyl triazene which can be converted thermally or by addition of base to form the diazo-compound or the acyl triazene can be isolated. The method is particularly useful for conversion of azides carrying one or more electron withdrawing groups to diazo-compounds. The method can be carried out in aqueous medium under mild conditions and is particularly useful for conversion of azido sugars to diazo-compound and diazonium salts thereof under physiological conditions. Tertiary phosphine reagents, particularly those that are water-soluble, and precursors for preparation of the reagents are provided.

23 Claims, 2 Drawing Sheets

PREPARATION OF DIAZO AND DIAZONIUM COMPOUNDS

CROSS-REFERENCE TO RELATED APPLICATIONS

This application claims the benefit of U.S. provisional application 61/115,474, filed Nov. 17, 2008, which is incorporated by reference herein in its entirety.

STATEMENT REGARDING FEDERALLY SPONSORED RESEARCH OR DEVELOPMENT

This invention was made with support from the United States government under grant number GM044783 from the National Institutes of Health. The U.S. government has certain rights in this invention.

BACKGROUND OF THE INVENTION

Diazo-compounds are remarkably versatile intermediates in organic synthesis, participating in a variety of thermal, photochemical and metal-catalyzed rearrangement, addition, cycloaddition and insertion reactions, typically with concomitant expulsion of $N_2$.[1] They have been found in nature, examples of which include azaserine[2] and members of the kinamycin[3] and lomaiviticin[4] families of marine natural products. Depending upon their stability and coexisting functional groups, diazo-compounds can present a challenge with respect to their preparation and isolation. Current methods include (a) diazo-transfer,[5] (b) diazotization,[6] (c) decomposition[7] or oxidation[8] of hydrazones, (d) rearrangement of N-alkyl N-nitroso-compounds,[9] (e) fragmentation of 1,3-disubstituted alkyl aryl-triazenes,[10] and (f) elaboration of more readily available diazo-compounds (FIG. 1).[11]

The preparation of diazo-compounds via the fragmentation of triazenes is uncommon. This route was described originally by Baumgarten, who isolated ethyl diazoacetate by the acid-catalyzed fragmentation of an aryl-triazene derivative (Eq. 1).[10a] More recent work by Bräse demonstrated that similar solid-supported triazenes, specifically those substituted with electron-deficient aryl groups, also undergo fragmentation under basic conditions (Eq. 2).[10b] The triazene precursors can be prepared by the addition of nitrogen-based nucleophiles to aryl diazonium salts or by the addition of organometallic species to azides with subsequent trapping of the resulting triazenyl anion with electrophiles, the former being the more popular approach.[12] These methods have limited synthetic utility.

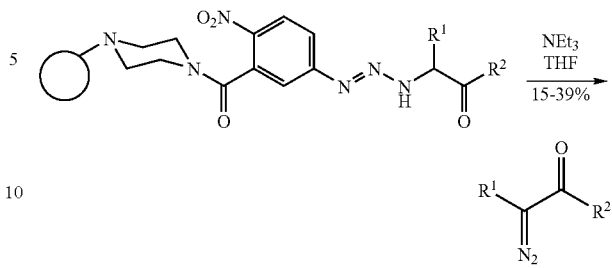

(1)

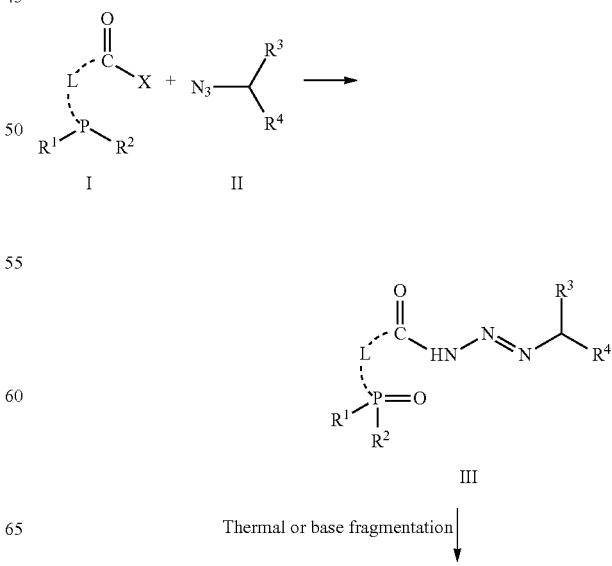

(2)

The present invention provides a convenient synthetic route converting azides to diazo-compounds employing a tertiary phosphine reagent under mild conditions. The method is believed to proceed via formation of an acyl triazene which undergoes fragmentation in situ to form the diazo-compound in high yield. Certain acyl triazenes can be isolated and have been found to undergo thermal or base catalyzed fragmentation to diazo-compounds.

SUMMARY OF THE INVENTION

The invention relates to a method for making diazo compounds, diazonium salts thereof and other protected forms of these compounds. Diazo compounds (IV) are prepared by reaction of a tertiary phosphine (I) carrying a reactive carbonyl group with an azide (II)(Scheme 1). In certain embodiments, the reaction forms an acyl triazene (III) which can be converted thermally or by addition of base to form the diazo-compound. In certain embodiment, the diazo-compound is formed directly without isolation of the acyltriazene and without a separate thermal or base fragmentation step.

More specifically, diazo compounds of formula IVa are prepared by reaction of a tertiary phosphine of structure I with an azide of formula IIa wherein the azide carries an electron withdrawing group (EWG), see Scheme 1

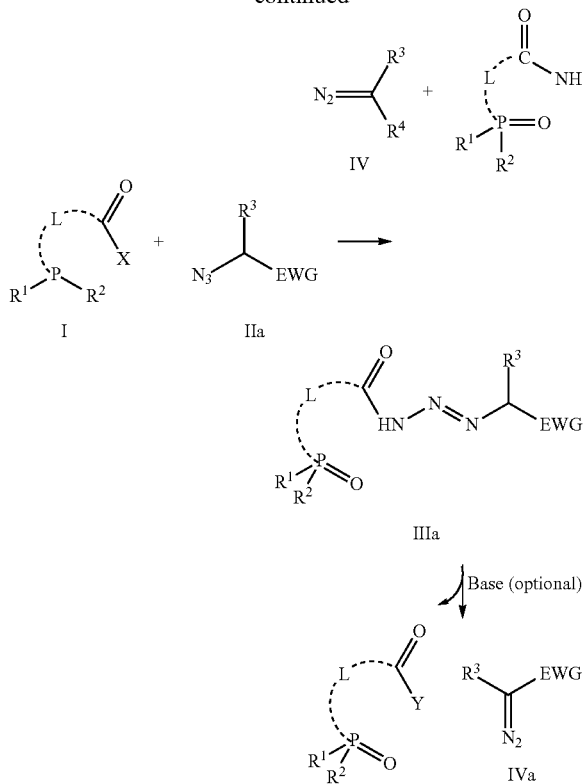

Without wishing to be bound by any particular mechanism of reaction, it is presently believed that phosphine I reacts with an azide II to form an acyl triazene III. In certain cases, e.g., when the azide has the structure of azide IIa (with an electron withdrawing group), the acyl triazene IIIa fragments thermally or optionally in the presence of added base to form diazo compound IVa. The triazenes III or IIIa can in some cases be isolated. Thus, the invention, in one aspect, provides a method for making diazo compounds from the corresponding azides. Phosphine reagent I functions as a reagent for converting the azide to the diazo compound. In another aspect, the invention provides a method for making acyl triazene compounds (III and IIIa).

The synthetic method herein for making diazo compounds is relatively mild and as such is particularly useful for the synthesis of diazo compounds which are sensitive to acids, base or oxidation conditions.

In an embodiment herein, the method of the invention generates diazo compound IVa or acyl triazene IIIa on reaction with azide IIa with a phosphine reagent of this invention. Alternatively, acyltriazene III is formed on reaction of azide II with a phosphine reagent of this invention.

In a specific embodiment, the method generates predominantly (greater than 50 molar % of the total diazo-compound and acyl triazene product formed) of the diazo-compound product. In a specific embodiment, the method generates predominantly (greater than 75 molar % of the total diazo-compound and acyl triazene product formed) of the diazo-compound product. In a specific embodiment, the method generates predominantly (greater than 95 molar % of the total diazo-compound and acyl triazene product formed) of the diazo-compound product.

In a specific embodiment, the method generates predominantly (greater than 50 molar % of the total diazo-compound and acyl triazene product formed) of the acyl triazene product. In a specific embodiment, the method generates predominantly (greater than 75 molar % of the total diazo-compound and acyl triazene product formed) of the acyl triazene product. In a specific embodiment, the method generates predominantly (greater than 95 molar % of the total diazo-compound and acyl triazene product formed) of the acyl triazene product.

In a specific embodiment, the method generates only the diazo-compound product as a stable product, for example, the acyl triazene may be unstable to fragmentation under the reaction conditions.

In specific embodiments, the method generates a total yield (based on limiting starting materials) of diazo-compound and acyl triazene product that is greater than 40%. In specific embodiments, the method generates a total yield (based on limiting starting materials) of diazo-compound and acyl triazene product that is greater than 50%. In specific embodiments, the method generates a total yield (based on limiting starting materials) of diazo-compound and acyl triazene product that is greater than 75%. In specific embodiments, the method generates a total yield (based on limiting starting materials) of diazo-compound and acyl triazene product that is greater than 90%. In specific embodiments, the method generates a yield (based on limiting starting materials) of diazo-compound that is greater than 50%. In specific embodiments, the method generates a yield (based on limiting starting materials) of diazo-compound that is greater than 75% or 90%.

In specific embodiments, the method generates less than about 10% (of the total product yield) of products of the Staudinger Ligation or Staudinger Reaction as described in FIG. 2. In specific embodiments, the method generates less than about 5% of such products.

The invention provides tertiary phosphine reagents of formula I:

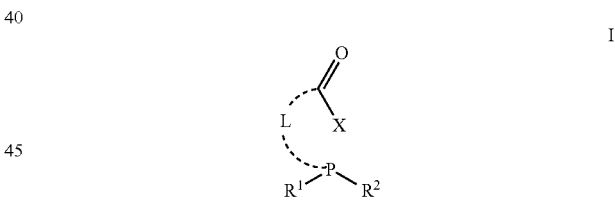

and salts thereof where:

X is a leaving group;

$R^1$ and $R^2$, independently, are selected from optionally substituted alkyl, alkenyl, alkynyl, aryl, alkylaryl, arylalkyl, heteroaryl, heterocyclic, —OR', or —N(R")$_2$ groups, phosphite (—P(R''')$_{3-r}$(OR')$_r$, aminophosphine (—P(R''')$_{3-r}$(N(R")$_2$)$_r$, or aminophosphite (—P(R''')$_{3-s-t}$(OR')$_s$(N(R")$_2$)$_t$, where r is 1-3, s and t are 1 or 2, where each R' and R''' is, independently, selected from hydrogen, alkyl, aryl, alkoxyalkyl, alkylaryl, arylalkyl, heteroaryl or heterocyclic groups; and each R" is, independently, selected from hydrogen, guanidine, alkyl, alkenyl, alkynyl, aryl, alkoxyalkyl, alkylaryl, arylalkyl, heteroaryl or heterocylic, and two R" or R''' together can form a 5- to 8-member optionally substituted heterocyclic ring containing one or more heteroatoms, one or more —CO— groups or both; or $R^1$ and $R^2$ together can form a 5- to 10-member optionally substituted heterocyclic ring containing the phosphorous atom and optionally containing one or more additional heteroatoms, one or more —CO— groups or both; or
one of $R^1$ or $R^2$ provides a linker to a solid surface;
L is a linking diradical which is an optionally substituted alkylene, arylene, heterocyclene, heteroarylene or combinations thereof; or
L is a linking diradical which is an optionally substituted alkylene, arylene, heterocyclene, heteroarylene or combinations thereof wherein one or more of the —C—, —CH—, or —CH$_2$— moieties of the linker can be replaced with one or more —O—, —S—, —NR—, —CO—, —COO—, —CONR—, —CS—O—, or —NRCO—NR— moieties, where each R is a hydrogen, an alkyl or an aryl group. More specifically, R of the L linking group is hydrogen or an alky group, particularly an alkyl having 1-3 carbon atoms.

In a related embodiment, the tertiary phosphine reagent of formula I is immobilized on a solid phase. In this case $R^1$ or $R^2$ is represented by -M-Solid, where M is a linking species which links the reagent moiety to the solid phase. M can be an organic diradical covalently linking the reagent to a surface. In an embodiment, M is a linking diradical which is an optionally substituted alkylene, arylene, arylalkylene, alkylarylene, heterocyclene, heteroarylene or combinations thereof in which one or more of the —C—, —CH—, or —CH$_2$— moieties of the linker can be replaced with one or more —O—, —S—, —NR—, —CO—, —COO—, —CONR—, —CS—O—, or —NRCO—NR— moiety, where each R is a hydrogen, an alkyl or an aryl group. and more specifically R is H or an alkyl having 1-3 carbon atoms. In an embodiment, M comprises a ligand (Lig)/ligand binding (LigB) species, for example represented by S-$M^1$-Lig-LigB-$M^2$-, where $M^1$ and $M_2$ are linking organic diradical each as described for M.

The surface to which the reagent of formula I can be linked can be any appropriate surface compatible with the reaction conditions and the desired applications. In specific embodiments, surfaces include glass, quartz, plastic or polymers, latex, silicon wafers, multi-wellplates, or metals. In specific embodiments, the surface is a plurality of beads or particles. In specific embodiments, the surface is polystyrene or polyethylene glycol.

In a specific embodiment, the tertiary phosphine reagent of the invention has formula I-1 or I-2:

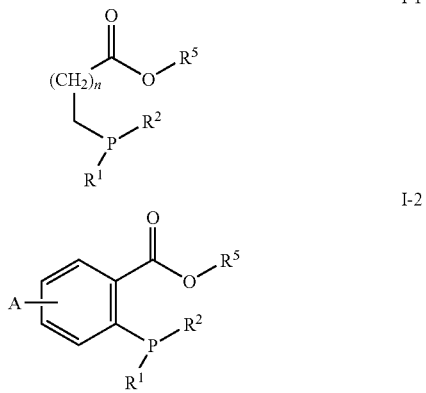

where $R^1$ and $R^2$ are as defined herein, n is an integer ranging from 1-5 inclusive, A represents hydrogen or one to five optional non-hydrogen substituents on the ring, and —CO—$OR^5$ is an activated ester group. In specific embodiments, n is 1, 2 or 3.

In a specific embodiment, —$OR^5$ is selected from:
(1) a-ON($R^7$)$_2$ group, a —O—$NR^7$—CO—$R^7$ group or a —O—N(CO$R^7$)—CO$R^7$, where each $R^7$ is an optionally substituted alkyl or aryl, or where the two $R^7$ groups together form an optionally substituted 5-8 member heterocyclic ring having one or more heteroatoms or —CO— groups or both in the ring;

(2) a phenyloxy group substituted with one or more halogens, hydroxy, nitro, alkyl, alkenyl, alkynyl, aryl, halogenated alkyl, hydroxy-substituted alkyl, amino-substituted alkyl, cyano, isocyano, thiocyano, isothiocyano, —SO$_2$, —SO$_3$R, —N(R)$_2$, —COR, —COOR, —CON(R)$_2$, —NR—CO—NR—, —CO—SR, —OR, or —SR, where each R, independently, is selected from hydrogen, alkyl, halogenated alkyl, alkenyl, alkynyl, aryl, halogenated aryl, heteroaryl, or heterocyclic groups, or two R together form a 5-8 member optionally substituted heterocyclic ring containing one or more heteroatoms, optionally one or more —CO— groups or both;

(3) —O—$R^5$ where $R^5$ is an optionally substituted heterocylic or heteroaromatic group; or (4) —O—SO$_2$—O—$R_S$ where $R_S$ is selected from halogen, optionally substituted alkyl, optionally substituted aryl, optionally substituted phenyl, halogenated alkyl, halogenated aryl, halogenated phenyl, fluorinated alkyl, fluorinated aryl, fluorinated phenyl, unsubstituted alkyl, unsubstituted phenyl, methyl, ethyl, —CF$_3$, —C$_4$F$_9$.

In specific embodiments, $R^5$ is —N(R')$_2$ where two R" together form a 5- or 6-member heterocyclic ring. In additional, specific embodiments —N(R")$_2$ is a oxo or dioxo-5- or 6-member heterocyclic ring. In exemplary embodiments, —N(R")$_2$ is 2,5-dioxo pyrrolidinyl, 2-oxopyrrolidinyl, 2,6-dioxopiperidinyl. 1-piperazenyl, 1-piperidinyl or 1-pyrrolidinyl.

In specific embodiments, $R^5$ is a substituted aryl group. In specific embodiments, $R^5$ is a substituted phenyl group. In specific embodiments, $R^5$ is a phenyl group substituted with one or more halogen, amino (—N(R")$_2$, nitro, cyano, —COR', —COOR', —CON(R")$_2$ or —SO$_3$R' groups, where R' is hydrogen or an optionally substituted alkyl or aryl group and each R", independently, is hydrogen, guanidine, alkyl, alkenyl, alkynyl, aryl, alkoxyalkyl, alkylaryl, arylalkyl, heteroaryl or heterocyclic, and two R" together can form a 5-8 member optionally substituted heterocyclic ring containing N and optionally one or more additional heteroatoms or one or more —CO— groups In specific embodiments, $R^5$ is a phenyl group substituted with 1-5 fluorines. In specific embodiments, $R^5$ is pentafluorophenyl, 4-nitrophenyl, 3-dialkyl aminophenyl, 3-dimethylaminophenyl, or 3-diethylaminophenyl. In specific embodiments, $R^5$ is a phenyl group substituted with one or more alkyl groups which in turn are substituted with one or more halogen, amino (—N(R")$_2$, nitro, cyano, or —SO$_3$R groups. In specific embodiments, $R^5$ is a heteroaryl group. In specific embodiments, $R^5$ is a 3-pyridinyl group.

In specific embodiments, the tertiary phosphine reagent is of formula V:

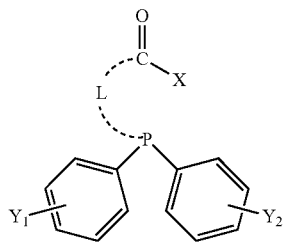

where X and L are as defined for formula I and $Y_1$ and $Y_2$ represents one or more non-hydrogen substituents on each phenyl ring. In specific embodiments, X is —$OR^5$ as defined herein. In specific embodiments, each $Y_1$ and each $Y_2$ substituent is, independently, selected from a halogen, —OH, an amino group (—$N(R_N)_2$), an optionally substituted alkyl group or an alkoxyalkyl group. In specific embodiments, each $Y_1$ and each $Y_2$ substituent is an amino group (—$N(R_N)_2$) or an alkyl group substituted with one or more —OH, —$N(R_N)_2$, —CO—$N(R_N)_2$, —COOH, or $COOR_C$ groups, where each $R_N$ is, independently, hydrogen, an alkyl, an alkenyl, an alkynyl, an aryl, an arylalkyl, an alkylaryl group or a guanidine, and $R_C$ is an alkyl, an aryl, an arylalkyl or an alkylaryl group. More specifically, each $R_N$ is, independently, selected from an optionally substituted alkyl or aryl. Two $R_N$ can be linked to form a 5-8 member ring which contains N and optionally contains one or more additional heteroatoms or which contains one or two oxy (—CO—) groups. The —$N(R_N)_2$ groups may be protonated or quaternary ammonium groups, particularly, —$NR(R_N)_2^+$, where R is hydrogen or an alkyl group. More specifically, $R_C$ is an alkyl group or an aryl group. Charged compounds can be in the form of salts with appropriate counter ions. In specific embodiments, each $R_N$, independently, is a hydrogen or an alkyl group having 1-6 or 1-3 carbon atoms. In specific embodiments, the substituted alkyl group has 1-6 or 1-3 carbon atoms. In specific embodiments, substituted alkyl groups are substituted with one or two of the listed substituents.

In a specific embodiment, the tertiary phosphine reagent of formula I is water-soluble and the reaction to form the acyl triazene or the diazo-compound can be carried out in an aqueous reaction medium. In specific embodiments the water soluble phosphine reagent is a compound of formula V.

In general any azide can be employed in the reaction herein. In a specific embodiment, the azides of the invention can be described, for example, by formula II, where $R^3$ is hydrogen, or an optionally substituted alkyl, alkenyl, alkynyl, aryl, alkyl aryl, aryl alkyl, heteroaryl, or heterocyclic group and $R^4$ is an optionally substituted alkyl, alkenyl, alkynyl, aryl, alkyl aryl, aryl alkyl, heteroaryl, heterocyclic group, where $R^3$ or $R^4$ together can form a 5- to 10-member ring which may be an optionally substituted carbocyclic ring or an optionally substituted heterocyclic ring in which one or more of the ring atoms can be replaced with —CO—. In a specific embodiment, at least one of $R^3$ or $R^4$ comprises an electron withdrawing group (EWG) or $R^3$ or $R^4$ together form a 5- to 10-member ring which comprises or is substituted with one or more EWG. In a specific embodiment, one or both of $R^3$ or $R^4$ are alkyl, alkenyl, alkynyl, aryl, alkyl aryl, aryl alkyl groups substituted with one or more EWG groups. In an embodiment, one or both of $R^3$ or $R^4$ are alkyl, alkenyl, alkynyl, or aryl groups substituted with one or more EWG groups. A number of EWG are known in the art and include, among others, nitro, cyano, halogen, ammonium (—$NR_3^+$), aryloxy, alkoxy, sulfonic ester (—$SO_2$—R), sulfonium (—$S(R)_2$)$^+$, phosphonium (—$P(R)_3$)$^+$, —COOR, —COR, —$CON(R)_2$, —OCOR, alkylthio, arylthio, aryl, —C≡CR, and —C=CR, where each R, independently, is hydrogen, or optionally substituted alky, alkenyl, alkynyl, aryl, alkylaryl, or arylalkyl, where two R the same atom may together form a 5- to 8-member heterocyclic ring in which one or more ring atoms can be replaced with —CO—.

In a related embodiment, the azide of the reaction may be immobilized on a surface. In an embodiment, $R^3$ or $R^4$ of the azide may include a linker species P-Solid for immobilization on the surface. IN general linker P is any chemical species which can provide for immobilization to a selected surface. In specific embodiments, linker P can be a diradical linker as described for the M linker herein or may contain a Lig/LigB pair as described for linker M herein. In a specific embodiment herein, the azide may be a molecule immobilized in tissue, in a cell, for example, in a cell membrane, or on a cell surface, for example, bouind to a cell surface receptor.

In an embodiment, the azide is of formula IIa where $R_3$ is hydrogen, or an optionally substituted alkyl, alkenyl, alkynyl, aryl, heteroaryl, or heterocyclic group and EWG is an electron withdrawing group, including among others, nitro, cyano, halogen, ammonium (—$NR_3^+$), aryloxy, alkoxy, sulfonic ester (—$SO_2$—R), sulfonium (—$S(R)_2$)$^+$, phosphonium (—$P(R)_3$)$^+$, —COOR, —COR, —$CON(R)_2$, —OCOR, alkylthio, arylthio, aryl, —C≡CR, and —C=CR, where each R, independently, is hydrogen, or optionally substituted alky, alkenyl, alkynyl, aryl, alkylaryl, or arylalkyl, where two R the same atom may together form a 5- to 8-member heterocyclic ring in which one or more ring atoms can be replaced with —CO—; and $R^3$ and EWG together can form a 5-8 member heterocyclic ring which optionally can have one or more heteroatoms and optionally can have one or more —CO— groups.

In specific embodiments, the azide of the reaction is a biological molecule having one or more azide groups. In specific embodiments, the may be an azide of a peptide or protein, or a sugar (a monosaccharide, disaccharide, oligosaccharidne or polysaccharide). In a specific embodiment, the azide may be a biological molecule in vitro or in vivo, for example, in an organism, in a cell (optionally in an organism or removed from an organism), in tissue (optionally in an organism or removed from an organism). In a specific embodiment, the azide of the biological molecule may be immobilized on a solid.

The diazo compounds made by the methods herein can be employed using art known methods to make diazonium salts. Diazonium salts are the conjugate acids of diazo-compounds and can be obtained by adding acid to the diazo compound. Certain diazonium salts, such as alkyl-based diazonium salts, as illustrated in Scheme 7, cannot be isolated. They can, however, be generated in situ and subsequently trapped. The acyl triazenes in this invention can be used to generate diazonium salts for in situ trapping. Aryl diazonium salts are often quite stable and can be isolated. Acyl triazenes derived from aryl azides (such as 8, Scheme 3), can fragment to diazonium salts under acidic conditions and certain of these diazonium salts can be isolated.

Acyl triazenes (III or IIIa) can in some cases be isolated from the reactions herein by precipitation. For example, after allowing the azide and the phosphine to react in THF/$H_2O$, a non-polar solvent can be added (such as diethyl ether) to induce precipitation of the acyl triazene (if it has not already completely fragmented thermally to diazo-compound). The acyl triazenes can also be isolated by silica gel column chromatography, but again some decomposition can occur in the process. In general acyl triazenes derived from aryl azides and alkyl azides (such as benzyl azides) are stable enough for column chromatography. Those azides bearing EWG groups may in some cases be too unstable for efficient isolation via column chromatography.

The invention also provides a method for making an acyl triazene compound which comprises the step of reacting a tertiary phosphine carrying a reactive carbonyl group with an azide. In a specific embodiment, the acyl triazene can be isolated.

In specific embodiments, the invention is directed to making an acyl triazene wherein the azide is an aryl or heteroaryl azide in which the azide group is bonded to the aryl or heteroaryl group and the aryl or heteroaryl group is optionally substituted.

The invention also provides isolated acyl triazenes made by the method of this invention The invention also provides reagent kits which comprise one or more reagents (of formula I) of this invention and which optionally include one or more of the following: one or more azides, one or more of solvents for carrying out the reaction, one or more bases for fragmenting the acyl triazene, or instructions for carrying out the invention. Kits may also comprise reagent immobilized on a selected solid or more reagents for immobilizing the reagent upon a solid. The kits of this invention are useful for carrying out methods of this invention. A kit comprises one or more components in appropriate packing. A kit may contain one or more reagents, substrates, solvents or the like in appropriate containers in an amount sufficient to carry out one or more than one reaction. In a specific embodiment, a kit may contain all reagents and solvents for carrying out one or a plurality of reactions.

Additional aspects and embodiments of the invention will be apparent on review of the detailed description and examples.

DETAILED DESCRIPTION OF THE INVENTION

Figure 1:
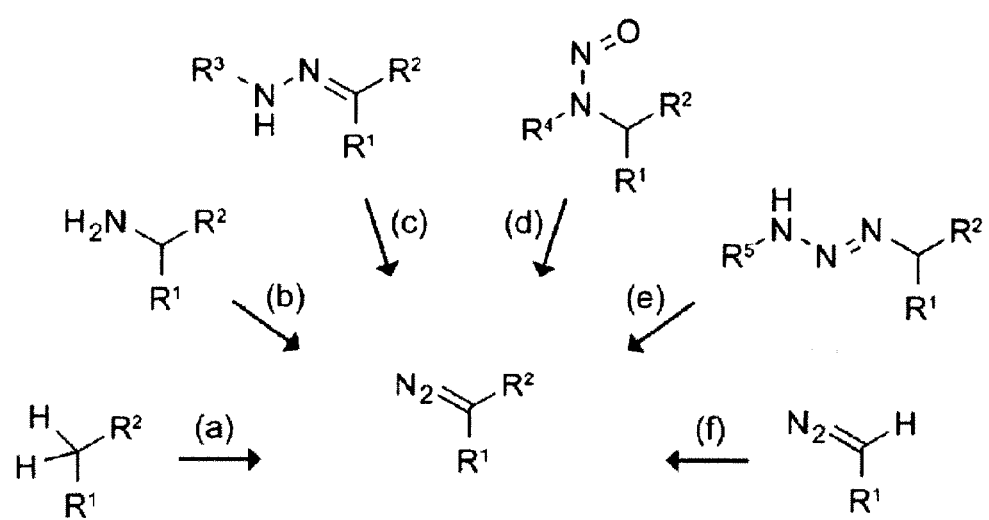
FIG. 1 illustrates various methods for known methods for preparation of diazo-compounds including (a) diazo-transfer,[5] (b) diazotization,[6] (c) decomposition[7] or oxidation[8] of hydrazones, (d) rearrangement of N-alkyl N-nitroso-compounds,[9] (e) fragmentation of 1,3-disubstituted alkyl aryl-triazenes,[10] and (f) elaboration of more readily available diazo-compounds.[11]
Figure 2:
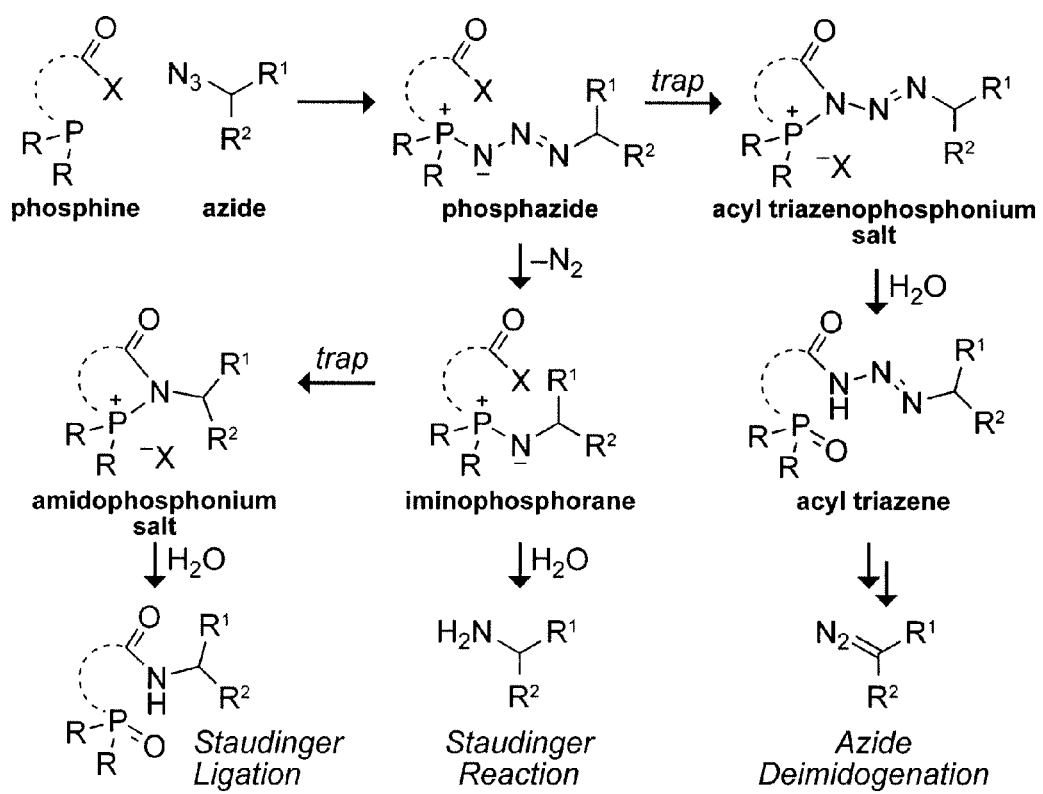
FIG. 2 illustrates possible reactions of a phosphine and an azide via formation of a phosphazides. An iminophosphorane is generated by the rapid extrusion of $N_2(g)$ from the phosphazide.[13] The Staudinger Reaction is amine formation on loss of water from the iminophosphorane. Intramolecular trapping in the iminophosphorane is the basis of the Staudinger Ligation.[15] Intramolecular trapping in the phosphazide, before loss of nitrogen, is the proposed mechanism of the reaction (azide deimidogenation) of the present invention. In this mechanism, loss of water after intramolecular trapping results in an acyl triazene which fragments (optionally thermally or base catalyzed) to give the azide.

Phosphazides are produced by the highly chemoselective reaction of a phosphine and azide (FIG. 2). Much of the interesting chemistry associated with this reaction emanates from an iminophosphorane, a species generated by the rapid extrusion of $N_2(g)$ from the phosphazide.[13] As illustrated in FIG. 2, the triazene and ultimately diazo compounds might be accessible from the phosphazide. A clear requirement for forming the triazenes and diazo compound is avoidance of $N_2(g)$-extrusion from the phosphazide. The isolation and trapping of phosphazides has typically been achieved through the careful choice of both the phosphine and the azide components.[14] The present invention is based at least in part on the discovery that the phosphazide can, under conditions and with reagents and azides as described herein, be trapped by an intramolecular acylation event reminiscent of the Staudinger ligation.[15]

Phosphines employed in the Staudinger ligation possess an O- or S-ester proximal to the phosphorus. This ester is reactive enough to trap the iminophosphorane, but not the foregone phosphazide, because extrusion of $N_2$ is apparently the faster process (FIG. 2).[16] It has been found that the presence of a more potent acylating moiety in the phosphine reagent resulted in formation of azides and acyltriazenes. It is believed that use of the more potent acylating moiety allowed trapping of the phosphazide by forming a triazenophosphonium species, which upon hydrolysis would provide an acyl triazene (FIG. 2). The electron distribution in acyl triazenes is similar to that in the triazenes employed by Baumgarten and Bräse in the preparation of diazo compounds (Eq 1 and 2[10]), so it is believed that the triazenes formed can fragment to form diazo-compounds.

The invention provides a method for making diazo compounds or acyl triazene compounds employing a deimidogenation phosphine reagent of formula I:

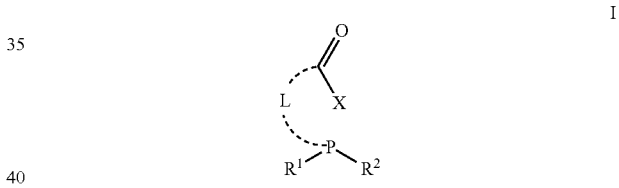

and salts thereof wherein:

X is a leaving group, and preferably is a good leaving group;

$R^1$ and $R^2$, independently, are selected from optionally substituted alkyl, alkenyl, alkynyl, aryl, alkylaryl, arylalkyl, heteroaryl, heterocyclic, —OR', or —N(R")$_2$ groups, phosphite (—P(R''')$_{3-r}$(OR')$_r$), aminophosphine (—P(R''')$_{3-r}$(N(R")$_2$)$_r$), or aminophosphite (—P(R''')$_{3-s-t}$ (OR')$_s$(N(R")$_2$)$_t$), where r is 1-3, s and t are 1 or 2, where each R' and R''' is, independently, selected from hydrogen, alkyl, aryl, alkoxyalkyl, alkylaryl, arylalkyl, heteroaryl or heterocylic groups; and each R" is, independently, selected from hydrogen, guanidine, alkyl, alkenyl, alkynyl, aryl, alkoxyalkyl, alkylaryl, arylalkyl, heteroaryl or heterocylic, or two R" or R''' together can form a 5- to 8-member optionally substituted heterocyclic ring containing one or more heteroatoms, one or more —CO— groups or both; or $R^1$ and $R^2$ together can form a 5- to 10-member optionally substituted heterocyclic ring containing the phosphorous atom and optionally containing one or more additional heteroatoms, one or more —CO— groups or both; or one of $R^1$ or $R^2$ provides a linker to a solid surface;

L is a linking diradical which is an optionally substituted alkylene, arylene, heterocyclene, heteroarylene or combinations thereof wherein one or more of the —C—, —CH—, or —CH$_2$— moieties of the linker can be replaced with one or more —O—, —S—, —NR—, —CO—, —COO—, —CONR—, —CS—O—, or —NRCO—NR— moieties, where each R is a hydrogen, an alkyl or an aryl group.

R$^1$ or R$^2$ linked to a surface can be represented by -M-, where M is a linking group which most generally is any art-recognized chemical species appropriate for linking the reagent of formula I to a selected solid surface.

In specific embodiments, the linker L herein can range from 1-30 atoms in length (length herein refers to the number of bonds between the groups linked and does not include branches) and typically ranges from 2-10 atoms in length. The L linker includes those having 1-30, 1-12, 1-6 and 1-3 carbon atoms. In specific embodiments, the L linker can be an alkylene, arylene, heterocyclene, or heteroarylene linker which is optionally substituted. In specific embodiments, the L linker can be an alkylene in which one or more of the —CH$_2$— moieties of the alkylene is replaced with one or more of —O—, —S—, —NR—, —CO—, —COO—, —CONR—, —CS—O—, or —NRCO—NR— moieties. More specifically, L is an optionally substituted alkylene, arylene, arylalkylene, alkylarylene, heterocyclene, heteroarylene in which one or more of the —CH$_2$-moieties of the linker are replaced with one or more —O—, or —S— moieties. In specific embodiments, the linker is a —CH$_2$—, a —CH$_2$—CH$_2$— or a —CH$_2$—CH$_2$—CH$_2$—. In specific embodiments, the L linker is a 1, 2-phenylene, a 1,3-phenylene or a 1,4-phenylene.

In specific embodiments, L is 1-8, 1-6, 2-6, 1-3 or 2-3 atoms in length. In specific embodiments, L has from 1-10, 1-6 or 1-3 carbon atoms. In specific embodiments, L is an optionally substituted alkylene or arylene. In a specific embodiment, L is —CH$_2$—CH$_2$—.

Linker M is selected for compatibility with the ligation chemistry and for compatibility with the application of the resulting surface carrying immobilized molecules. The M linker may be a linker covalently bonded between the reagent and the solid surface. Alternatively, the linker may be formed by binding of a ligand (bound to the reagent or to the surface) to a ligand binding agent (bound to the surface or to the reagent), e.g., a protein, antibody or other biological molecule having a binding affinity for a ligand can be immobilized on a surface or the ligand can be immobilized on a surface. Specific examples, of ligand (Lig)/ligand binding agent (LigB) pairs useful in immobilization of reagents of the invention on a surface, include, among others, antigen/antibody, biotin (or biotin derivative)/avidin or streptavidin, poly His-tag/metal (Ni or Cu). In this case R$_1$ or R$_2$ can be represented by -M$_1$-Lig-LigB-M$_2$-Solid or -M$_1$-LigB-Lig-M$_2$-, where Lig is a ligand and LigB is a corresponding ligand binding species that can bind to that ligand and M$_1$ and M$_2$ are chemical linking moieties each as defined for M above linking the ligand or liganding binding agent to the reagent and the ligand rer or to the surface, respectively. For example, the ligand, such as a biotinyl group, can be covalently bonded to the reagent and the ligand binding agent, such as avidin or streptavidin can be mobilized on a surface.

The M linker may be a cleavable linker, for example a linker which is photocleavable or chemically cleavable. The M linker to the solid surface can generally be any useful length, but in specific embodiments is 2 to 1000, 2-100, 2-50, 2-25 or 2-10 atoms in length. The M linker to the solid surface can generally contain any number of carbon atoms, but in specific embodiments contains is 2 to 1000, 2-100, 2-50, 2-25 or 2-10 carbon atoms.

In specific embodiments, M is an optionally substituted alkylene, arylene, arylakylene, alkylarylene, heterocyclene, heteroarylene, or combinations thereof with optional end groups, including among others, —(CH$_2$)$_s$— (where s is an integer, typically 1-10), —O—, —S—, —NR—, —CO—, —CS—, —COO—, —CO—S—, —CO—NR—, —NRCO—NR—, —SO—, —SO$_2$—, —SO$_3$—, —Si(R)$_2$—, —O—Si(R)$_2$—, that function for bonding the linker between the compound of formula I and the surface of the solid. In other embodiments, M is an optionally substituted alkylene, arylene, arylalkylene or alkylarylene linker. in which one or more —C—, —CH—, —CH$_2$— moieties are replaced with one or more of —O—, —NR—, —S—, —CO—, —CS—, —COS—, —COO—, —CONR, —NRCO—NR—, —SO—, —SO$_2$—, —SO$_3$—, —Si(R)$_2$—, or —O—Si(R)$_2$—. In other embodiments, M is an optionally substituted alkylene, arylene, arylalkylene or alkylarylene linker. in which one or more —C—, —CH—, —CH$_2$— moieties are replaced with one or more of O—, —NR—, —S—, —CO—, —CS—, —COS—, —COO—, —CONR, —NRCO—NR—, —SO—, —SO$_2$—, —Si(R)$_2$—, or —O—Si(R)$_2$— and end groups as noted above which function for bonding between the compound of formula I and the solid. In the linkers above, each R, independently, is hydrogen, alkyl, or aryl and two R groups in the linker may be bonded together to form a 5-8 member carbocyclic or heterocyclic ring. In specific embodiments of the listed linker groups, R is hydrogen or alkyl having 1-3 carbon atoms.

In specific embodiments, the linker M comprises a straight-chain alkylene in combination with a cycloalkylene, heterocyclene, arylene or heteroarylene, e.g., —(CH$_2$)$_{s1}$—B—(CH$_2$)$_{s2}$— (where s1 and s2 are integers, typically 1-10, and B is the cycloalkylene, heterocyclene, arylene or heteroarylene. Preferred B have 5- or 6-member rings. B includes among others, 1,4-cyclohexylene, 1,4-phenylene, 1,3-phenylene, 2,5-pyridylene, or 1,4-piperazinylene.

In specific embodiments, the linker L comprises a straight-chain alkylene in combination with a cycloalkylene, heterocyclene, arylene or heteroarylene, e.g., —(CH$_2$)$_{s1}$—C—(CH$_2$)$_{s2}$— (where s1 and s2 are integers, typically 1-10, and C is the cycloalkylene, heterocyclene, arylene or heteroarylene. Preferred C have 5- or 6-member rings. B includes among others, 1,4-cyclohexylene, 1,4-phenylene, 1,3-phenylene, 2,5-pyridylene, or 1,4-piperazinylene.

In specific embodiments, leaving group X is selected from, a halogen (particularly I, Br or Cl), fluorosulfonate (—OSO$_2$—F), —OClO$_3$ (perchlorate), an —OR$_Y$, —SR$_Y$, —O—N(R$_Z$)$_2$, or —OSO$_2$—R$_Y$, where each R$_Y$, independently, is hydrogen, or an optionally substituted alkyl, alkenyl, alkynyl, aryl, heteroaryl or heterocyclic group, each R$_Z$, independently, is an optionally substituted alkyl, aryl or heterocyclic group and where two R$_Z$ together can form an optionally substituted 4-10 member carbocyclic or heterocylic ring. In specific embodiments, X is —OR$^5$ where R$^5$ is a substituted phenyl group.

In more specific embodiments, the X group of formulas herein is selected from aryloxy groups (aryl-O—) arylthio group (aryl-S—), a sulfonic ester group (aryl/alkyl-OSO$_2$—) or an aminooxy group ((alkyl/aryl)$_2$—N—O—) a halogen (e.g., Br, Cl and I), fluorosulfonate (—OSO$_2$—F) and —OClO$_3$ (perchlorate), wherein any alkyl or aryl groups in these leaving groups are optionally substituted as defined herein below. Additional X are substituted aryloxy, heterocylooxy, heteroaryloxy, alkylthio, arylthio, alkyl sulfonic esters, aryl sulfonic esters, alkyl aminooxy, aryl aminooxy, and halogen. More specific leaving groups useful in the methods of this invention include, a —ON(R$_Z$)$_2$ group, a —O—NR$_Z$—CO—R$_Z$ group, a —O—N(COR$_Z$)—COR$_Z$, where each R$_Z$, independently, is an optionally substituted alkyl or aryl, or where two R$_Z$ groups together form an optionally substituted 5- to 8-member heterocyclic ring.

Additional specific useful leaving groups X are difluorophenoxy, trifluorophenoxy, pentafluorophenoxy, p-toluenesulfonate, p-bromobenzenesulfonate, p-nitrobenzenesulfonate, methanesulfonate, trifluoromethanesulfonate, nonafluorobutanesulfonate, 2,2,2-trifluoroethanesulfonate, ammoniumalkanesulfonate, 2-oxopyrrolidinyl and 2,5-dioxopyrrolidinyl.

In specific embodiments of the formulas herein, $R^1$ and $R^2$ are optionally substituted alkyl or aryl groups. In specific embodiments of the formulas herein, $R^1$ and $R^2$ are unsubstituted alkyl or aryl groups. In more specific embodiments of the formulas herein, $R^1$ and $R^2$ are optionally substituted alkyl or phenyl groups. In specific embodiments of the formulas herein, $R^1$ and $R^2$ are optionally substituted phenyl, biphenyl or naphthyl groups. In specific embodiments of the formulas herein, $R^1$ and $R^2$ are optionally substituted alkyl groups having 1-10, 1-6 or 7-10 carbon atoms. In additional embodiments of the formulas herein, $R^1$ and $R^2$ are fluorinated alkyl groups which can contain 1-20 carbon atoms and 3-41 fluorines. In more specific embodiments of the formulas herein, $R^1$ and $R^2$ are fluorinated alkyl groups having 6-12, 8-20, or 12-20 carbon atoms which can be substituted by 5-41 fluorines. In specific embodiments of the formulas herein, the alkyl groups are perfluorinated alkyl groups. More specific $R^1$ and $R^2$, include trifluoromethyl and perfluoroethyl groups.

In specific embodiments, $R^1$ and $R^2$, independently, are $R_V$, —OR$_W$, or —N(R$_X$)$_2$ groups where R$_V$ is an optionally substituted alkyl, aryl, heteroaryl or heterocyclic, and each R$_W$ and R$_X$, independently, is selected from hydrogen, or optionally substituted alkyl, aryl, heteroaryl or heterocyclic. In specific embodiments, both of $R^1$ and $R^2$ are —OR$_W$, or both of $R^1$ and $R^2$ are —N(R$_X$)$_2$, or $R^1$ is —OR$_W$ and $R^2$ is —N(R$_Z$)$_2$. In specific embodiments, two R$_Z$ together form an optionally substituted 5-8 member heterocyclic ring including the N and optionally including one or more additional heteroatoms and/or one or more —CO— groups. In specific embodiments, two R$_Z$ together form an optionally substituted 5-8 member heterocyclic ring including only the one heteroatom, N.

In specific embodiments, $R^1$ and $R^2$ together form a 5- to 10-member ring containing the phosphorous atom. In specific embodiments, $R^1$ and $R^2$ together form a 5- to 10-member ring containing the phosphorous atom and optionally one or more additional heteroatoms and/or one or more —CO— groups. In other embodiments, the ring is a 5- to 8-member ring. In other embodiments, the ring is a 5- or 6-member ring. In any such embodiments, the ring can contain only carbon atoms and the phosphorous atom. In any such embodiments, the ring can contain carbon atoms and one or two hetero atoms in addition to the phosphorous. In specific embodiments, the other heteroatoms are O, NR, or P. In specific embodiments, the ring can contain one or more —CO— groups.

In specific embodiments, $R^1$, $R^2$ or both can be oxoalkyl, oxoalkenyl, oxoalkynyl or oxoheterocyclic groups having one or more —CO— groups therein.

In more specific embodiments, $R^1$ and $R^2$ are phenyl groups substituted with one or more of a halogen, an optionally substituted alkyl group, an alkoxy group, or an alkoxyalkyl group. In other specific embodiments, $R^1$ and $R^2$ are phenyl groups substituted with one or more amino groups (—N(R$_N$)$_2$) or alkyl groups which are in turn substituted with one or more —OH, —N(R$_N$)$_2$, —COOH, or —COOR$_C$ groups, where each R$_N$ is, independently, hydrogen, an alkyl, an alkenyl, an alkynyl, an aryl, an arylalkyl, an alkylaryl group, a guanidine or a heteroaryl group wherein two R$_N$ can be linked together to form a 5-8 member ring which contains N and optionally contains one or more additional heteroatoms or which contains one or two oxy (—CO—) groups, and R$_C$ is an alkyl, an alkenyl, an alkynyl, an aryl, an arylalkyl or an alkylaryl group. More specifically, each R$_N$ is, independently, a hydrogen or an alkyl group. Alkyl groups can be straight-chain, branched or cycloalkyl groups. More specifically, R$_C$ is an alkyl group or an aryl group.

In specific embodiments of formulas herein, $R^1$ and $R^2$ are both phenyl groups which are each substituted with one or more alkyl groups which are in turn substituted with one or more amino groups (—N(R$_N$)$_2$), or ammonium groups (—NH(R$_N$)$_2$$^+$ or —N(R$_N$)$_3$$^+$ where each R$_N$ is, independently, hydrogen, alkyl, aryl, alkylaryl, or arylalkyl and two RN can together for a 5-8 member heterocyclic ring containing N and optionally containing one or more additional heteroatoms and/or one or more —CO—. In specific embodiments, the substituent is —NH(R$_N$)$_2$$^+$. In specific embodiments, each alkyl substituent on the phenyl ring is substituted with only one amino or ammonium group. More specifically, each R$_N$ is, independently, hydrogen or an alkyl groups having 1-3, 1-6 or 1-10 carbon atoms. In a specific embodiment, each R$_N$ is, independently, an alkyl group. In a specific embodiment, two R$_N$ are alkyl groups. In specific embodiments, two R$_N$ are the same alkyl groups. In specific embodiments, two R$_N$ are both methyl groups or ethyl groups. Compounds carrying positively charged substituents can be in the form of salts with appropriate anions.

In specific embodiments of formulas herein, $R^1$ and $R^2$ are both phenyl groups each of which is substituted with one or more alkyl groups which are in turn substituted with one or more —OH, —COOH, —COO$^-$, or —COOR$_C$, groups, where R$_C$ is an alkyl, alkenyl, alkynyl, aryl, alkylaryl, or arylalkyl group. In specific embodiments, each alkyl substituent on the phenyl ring is substituted with only one of the listed groups. In specific embodiments, each alkyl substituent on the phenyl ring is substituted with one, two or more —OH groups. Compounds carrying negatively charged substituents can be in the form of salts with appropriate cations.

In specific embodiments of the formulas herein, $R^1$ and $R^2$ are both phenyl groups each of which is substituted with one or more alkyloxyalkyl groups. In specific embodiments, the alkyoxyalkyl groups have 2-10 carbon atoms and 1, 2 or 3 oxygen atoms.

In specific embodiments of formulas herein, $R^1$ and $R^2$ are both phenyl groups each substituted with one or more amino groups (—N(R$_N$)$_2$), or ammonium groups (—N(R$_N$)$_3$$^+$, —OH, —COOH, —COO$^-$, or —COOR$_C$ groups, where each R$_N$ is, independently, hydrogen, alkyl, aryl, alkylaryl, or arylalkyl and In specific embodiments, the substituent is —NH(R$_N$)$_2$$^+$ and where R$_C$ is an alkyl, aryl, alkylaryl, or arylalkyl group. More specifically, each R$_N$ is, independently, hydrogen or an alkyl group having 1-3, 1-6 or 1-10 carbon atoms. In a specific embodiment, each R$_N$ is, independently, an alkyl group. In a specific embodiment, two R$_N$ are alkyl groups. In specific embodiments, two R$_N$ are the same alkyl groups. In specific embodiments, two R$_N$ are both methyl groups or ethyl groups. Compounds carrying positively or negatively charged substituents can be in the form of salts with appropriate counterions.

In specific embodiments of formulas herein, $R^1$ and $R^2$ are both phenyl groups each of which is substituted with one or more alkyl groups which are in turn substituted with one or more —OH, —COOH, —COO$^-$, or —COOR$_C$, groups, where $R_C$ is an alkyl, alkylaryl, or arylalkyl group. In specific embodiments, each alkyl substituent on the phenyl ring is substituted with only one of the listed groups. In specific embodiments, each alkyl substituent on the phenyl ring is substituted with one, two or more —OH groups. Compounds carrying charged groups may be in the form of salts with appropriate counterions.

In specific embodiments of the formulas herein, $R^1$ and $R^2$ are both phenyl groups each of which is substituted with one or more alkyloxyalkyl groups. In specific embodiments, the alkyoxyalkyl groups have 2-10 carbon atoms and 1, 2 or 3 oxygen atoms.

In additional specific embodiments of formulas herein, both of $R^1$ and $R^2$ are unsubstituted phenyl rings.

In specific embodiments of formulas herein, $-N(R_N)_2$ is a 5- or 6-member heterocyclic ring. In additional, embodiments $-N(R_N)_2$ is a oxo or dioxo-5- or 6-member heterocyclic ring. In exemplary embodiments, $-N(R_N)_2$ is 2,5-dioxo pyrrolidinyl, 2-oxopyrrolidinyl, or 2,6-dioxopiperidinyl. In exemplary embodiments, $-N(R_N)_2$ is 1-piperazenyl, 1-piperidinyl or 1-pyrrolidinyl.

In specific embodiments of chemical groups, moieties and substituents herein, two R groups (any of the various R, R', R", $R_N$, etc. groups herein), particularly which are substituted on the same N atom or substituted on the same P atom, can together form a 5- to 10-member (or 5- to 8-member or preferably a 5- or 6-member) ring, which may be carbocyclic or heterocyclic ring. In these cases, the two R groups represent a diradical species bonding across one atom or more than one atoms. The rings formed may contain one or more heteroatoms in the ring. In specific embodiments, there are 1, 2 or 3 heteroatoms in a ring. The heteroatoms may be the same (e.g., all N) or they may be a combination of different heteroatoms (e.g., N and O; N and S; N and P; P and O etc.) Additionally, one or more ring members can be a —CO— group. In specific embodiments, a ring can contain one —CO— or two —CO— groups. The ring formed by the two R groups together may also be unsaturated, having one or more double bonds. Further, the ring is optionally substituted. In specific embodiments, the ring is optionally substituted with one or more halogen, hydroxyl, alkyl or aryl groups.

In general any azide can be employed in the reaction of this invention. In specific embodiments, the azide contains one or more electron withdrawing groups. In specific embodiments, the azide is an alkyl, alkenyl, alkynyl, aryl, heteroaryl, or heterocyclic azide which in addition is substituted with one or more EWG. A number of EWG are known in the art and include among others, nitro, cyano, halogen, ammonium ($-NR_3^+$), aryloxy, alkoxy, sulfonic ester ($-SO_2-R$), sulfonium ($-S(R)_2)^+$, phosphonium ($-P(R)_3)^+$, —COOR, —COR, —CON(R)$_2$, —OCOR, alkylthio, arylthio, aryl, —C≡CR, and —C=CR.

In an embodiment, the azide is of formula IIa where $R_3$ is hydrogen, or an optionally substituted alkyl, alkenyl, alkynyl, aryl, heteroaryl, or heterocyclic group and EWG is an EWG group, including among others, nitro, cyano, halogen, ammonium ($-NR_3^+$), aryloxy, alkoxy, sulfonic ester ($-SO_2-R$), sulfonium ($-S(R)_2)^+$, phosphonium ($-P(R)_3)^+$, —COOR, —COR, —CON(R)$_2$, —OCOR, alkylthio, arylthio, aryl, —C≡CR, and —C=CR. In this embodiment, $R^3$ and EWG can together form a 5- to 8-member heterocyclic ring.

In specific embodiments, the azide (II or IIa) is an optionally substituted 5-7 member ring ketone (where $R^3$ and $R^4$ or $R^3$ and EWG are joined to form the ring), lactone or lactam of formula:

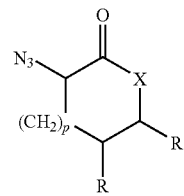

II-1 where p is zero, 1 or 2, X is —CH$_2$—, —O—, or NR', where R' is hydrogen, or an optionally substituted alkyl, alkenyl, alkynyl or aryl group and each R is hydrogen or an optionally substituted alkyl, alkenyl, alkynyl or aryl group or two R together form an optionally substituted 5-10 member carbocyclic or heterocyclic ring optionally having one or more —CO— in the ring or two R together form an aryl or heteroary group having one or two rings.

In other specific embodiments, of formula IIa, $R^3$ is hydrogen and EWG is a —CO—OR$^6$ group. In other specific embodiments of formula IIa, $R^6$ is an optionally substituted alkyl, aryl, alkoxy, thioalkyl, aryloxy, thioaryl, or an amino ($-N(R")_2$) or protected amino group ($-NR"PR$). In specific embodiments of formula IIa, $R^3$ is an optionally substituted aryl or arylalkyl group and EWG is an optionally substituted aryl group. In specific embodiments of formula IIa, $R^3$ is an optionally substituted aryl or arylalkyl group and EWG is the —CO—OR$^6$ group. In other specific embodiments, $R^3$ and EWG together form an oxo-substituted carbocyclic group having one, two or three rings, one, two or three of which are aromatic rings, wherein the oxo group is optionally positioned on the carbon alpha to the carbon carrying the azide group.

In additional specific embodiments, azide of formula II or IIa contains more than one azide group. In a specific embodiment, the azide contains a single azide group. In other embodiments, the azide contains two azide groups. In some cases, the azide may contain azide groups which because of their positions in the compound exhibit significantly different reactivity in the reaction of this invention. In this case, reaction may occur predominantly or exclusively at one of the azide groups.

In specific embodiments of formulas herein:

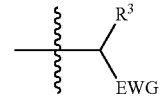

is an optionally substituted aryl or heteroaryl group, e.g., a phenyl, biphenyl, naphthyl or fluorene group or an optionally substituted phenyl, biphenyl, naphthyl or fluorene group.

In specific embodiments of formulas herein, EWG is an optionally substituted aryl or heteroaryl group or a —CO—R$^6$ group, where $R^6$ is an alkyl, alkenyl, alkynyl, aryl, heteroaryl, heterocycly, alkoxy, alkylthio, aryloxy, heteroaryloxy, arylthio, heteroarylthio, heterocyclyoxy, heterocyclythio, each of which is optionally substituted, an amino ($-N(R_T)_2$) or a protected amino group ($-NR_TPR$) group, where each $R_T$ is hydrogen or an optionally substituted alkyl or aryl group and PR is an appropriate art-recognized amine protecting group and wherein $R^3$ and EWG or —CO—R$^6$ together can optionally form an optionally substituted heterocyclic ring having 5-10 ring member atoms. In specific embodiments, the ring contains 5- to 8-members. In other specific embodiments, the ring contains 5- or 6-members. In any of such embodiments, the ring members can be carbon atoms. In any of such embodiments, the ring members are carbon atoms with one or two heteroatoms. In specific embodiments, the heteroatoms in the ring are oxygen, or nitrogen. In specific embodiments, the ring contains one, two or more —CO groups.

In specific embodiments, $R^3$ is hydrogen and EWG is an optionally substituted aryl or heteroaryl group.

In specific embodiments, $R^3$, $R^6$ or both which are alkyl, alkenyl, alkynyl or heterocyclic can be oxoalkyl, oxoalkenyl, oxoalkynyl or oxoheterocyclic groups having one or more —CO— groups therein.

In the azide, $R^3$ and EWG may together form an optionally substituted carbocyclic or heterocyclic ring. In a specific embodiment, $R^3$ and EWG together form a 5- or 6-member ring. In a specific embodiment, the 5- or 6-member is an electron withdrawing group or is substituted with one or more electron withdrawing groups.

In a specific embodiment, the tertiary phosphine reagent of the invention has formula I-1 or I-2:

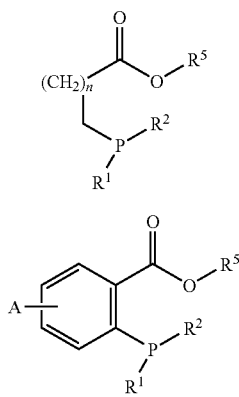

where $R^1$ and $R^2$ are as defined herein, n is an integer ranging from 1-5 inclusive, A represents hydrogen or one to five optional non-hydrogen substituents on the ring, and —CO—$OR^5$ is an activated ester group. An "activated ester group" refers to a carboxylic acid ester which is more reactive than an alkyl ester (e.g., methyl ester) in reactions in which the carbonyl moiety is an electrophilic center. In specific embodiments, —$OR^5$ is —O—$N(R')_2$, or —$OSO_2$—R, as defined herein. Additional examples of activated ester groups include those in which $R^5$ is a nitro-substituted, —$N(R')_2$-substituted, or a halogenated phenyl group, particularly those having 2-5 halogens, including, for example, pentafluorophenyl and 2,4,6-trichlorophenyl, 4-nitrophenyl groups. Additional examples of $R^5$ include heterocyclic and heteroaryl groups, particularly those having 5- o5 6-member rings, and particularly those heterocyclic and heteroaryl groups having one or two nitrogens and optionally having one oxygen or optionally having one or two —CO— groups in the ring.

In another embodiment, $R_5$ is a phenyl ring substituted with one or more alkyl groups which in turn are substituted with one or more —OH, —$N(R_N)_2$, —COOH, or —$COOR_C$ groups, where each $R_N$ is, independently, hydrogen, an alkyl, an alkenyl, an alkynyl, an aryl, an arylalkyl, an alkylaryl group or a guanidine, and $R_C$ is an alkyl, an aryl, an arylalkyl or an alkylaryl group. More specifically, each $R_N$ is, independently, an alkyl group. Two $R_N$ can be linked to form a 5-8 member ring which contains N and optionally contains one or more additional heteroatoms or which contains one or two oxy (—CO—) groups. The —$N(R_N)_2$ groups may be protonated or quaternary ammonium groups. More specifically, $R_C$ is an alkyl group or an aryl group. Charged compounds can be in the form of salts with appropriate counter ions. In specific embodiments, $R_N$ are hydrogens or alkyl groups having 1-6 or 1-3 carbon atoms. In specific embodiments, the substituted alkyl group has 1-6 or 1-3 carbon atoms. In specific embodiments, substituted alkyl groups are substituted with one or two of the listed substituents.

In more specific embodiments of formula I-1, and I-2 n is 1 and —$OR^5$ is —O—$N(R')_2$. In other more specific embodiments of formula I-1 and I-2, n is 1 and —$N(R')_2$ is: 2,5-dioxo pyrrolidinyl, 2-oxopyrrolidinyl, or 2,6-dioxopiperidinyl. In additional specific embodiments, both of $R^1$ and $R^2$ are phenyl rings.

In embodiments of formulas herein, —$OR^5$ is —O—$N(R')_2$. In other more specific embodiments, —$N(R')_2$ is: 2,5-dioxo pyrrolidinyl, 2-oxopyrrolidinyl, or 2,6-dioxopiperidinyl.

In specific embodiments, the tertiary phosphine has the formula:

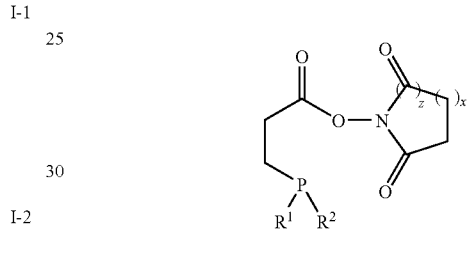

where $R^1$ and $R^2$ are as defined herein and z is 1 or 0 and when z is 1, x is 1-8 and when z is 0, x is 2 to 8. In more specific embodiments, $R^1$ and $R^2$ are optionally substituted phenyl groups In specific embodiments, the tertiary phosphine reagent is of formula V:

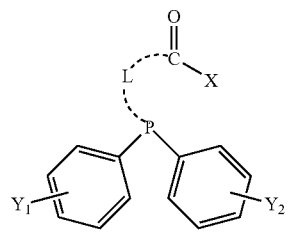

where X and L are as defined for formula I and $Y_1$ and $Y_2$ represents one or more non-hydrogen substituents on each phenyl ring. In specific embodiments, each $Y_1$ and each $Y_2$ substituent is, independently, selected from a halogen, —OH, an amino group (—$N(R_N)_2$), an optionally substituted alkyl group or an alkoxyalkyl group. In specific embodiments, each $Y_1$ and each $Y_2$ substituent is an amino group (—$N(R_N)_2$) or an alkyl group substituted with one or more —OH, —$N(R_N)_2$, —COOH, or —$COOR_C$ groups, where each $R_N$ is, independently, hydrogen, an alkyl, an alkenyl, an alkynyl, an aryl, an arylalkyl, an alkylaryl group or a guanidine, and $R_C$ is an alkyl, an aryl, an arylalkyl or an alkylaryl group. More specifically, each $R_N$ is, independently, selected from an optionally substituted alkyl or aryl. Two $R_N$ can be linked to form a 5-8 member ring which contains N and optionally contains one or more additional heteroatoms and/or which contains one or two oxy (—CO—) groups. The —N(R$_N$)$_2$ groups may be protonated or quaternary ammonium groups. More specifically, R$_C$ is an alkyl group or an aryl group. Charged compounds can be in the form of salts with appropriate counter ions. In specific embodiments, R$_N$ are hydrogens or alkyl groups having 1-6 or 1-3 carbon atoms. In specific embodiments, the substituted alkyl group has 1-6 or 1-3 carbon atoms. In specific embodiments, substituted alkyl groups are substituted with one or two of the listed substituents.

In specific embodiments, the tertiary phosphine reagent is of formula V-1 or V-2:

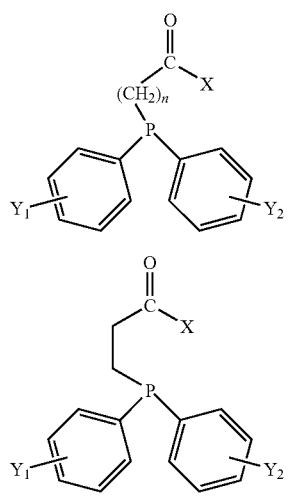

V-1

V-2 where n is an integer ranging from 1-5 inclusive, X is as defined for formula I above and Y$_1$ and Y$_2$ are as defined in formula V. In specific embodiments, each Y$_1$ or Y$_2$ is an alkyl substituted with an —N(R$_N$)$_2$ where each R$_N$ is an alkyl group or the two R$_N$ together form a 5-8 member heterocyclic ring containing the N and optionally another heteroatom or —CO— moiety.

In specific embodiments, the tertiary phosphine reagent is of formula V-3 or V-4:

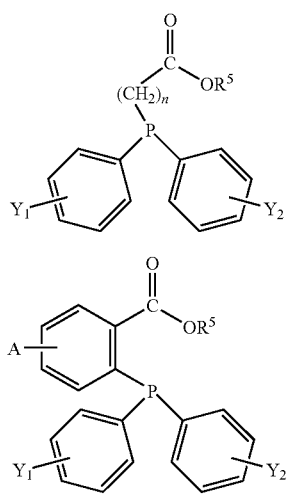

V-3

V-4 where n is an integer ranging from 1-5, inclusive, Y$_1$ and Y$_2$ are as defined in formula V, A represents hydrogen or one to five optional non-hydrogen substituents on the ring, and —CO—OR$^5$ is an activated ester group as defined above. Additional examples of activated ester groups include those in which R$^5$ is a nitro-substituted or halogenated phenyl group, particularly those having 3-6 halogens, including, for example, pentafluorophenyl and 2,4,6-triclorophenyl and 4-nitrophenyl groups. In specific embodiments, —OR$^5$ is —O—N(R')$_2$, or —OSO$_2$—R, as defined above. In specific embodiments, A is hydrogen. In specific embodiments, A is a halogen, —OH, alkyl, or alkoxy group. In specific embodiments, each Y$_1$ or Y$_2$ is an alkyl substituted with an —N(R$_N$)$_2$ where each R$_N$ is an alkyl group or the two R$_N$ together form a 5-8 member heterocyclic ring containing the N and optionally another heteroatom or —CO— moiety.

In specific embodiments, the tertiary phosphine reagent is of formula V-5:

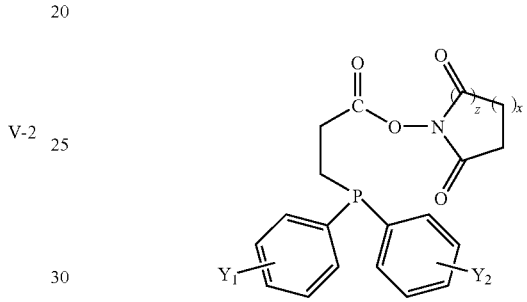

where Y$_1$ and Y$_2$ are as defined in formula V and z is 1 or 0 and when z is 1, x is 1-8 and when z is 0, x is 2 to 8. In specific embodiments, A is hydrogen. In specific embodiments, A is a halogen, —OH, alkyl, or alkoxy group. In specific embodiments, each Y$_1$ or Y$_2$ is an alkyl substituted with an —N(R$_N$)$_2$ where each R$_N$ is an alkyl group or the two R$_N$ together form a 5-8 member heterocyclic ring containing the N and optionally another heteroatom or —CO— moiety.

In specific embodiments of all formulas herein one or both of R$^1$ and R$^2$ are groups of formula:

Structure VIa

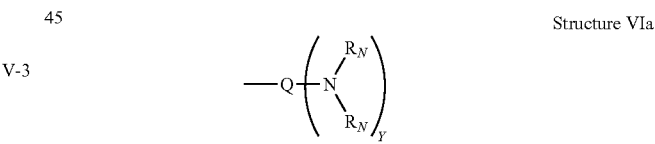

as well as protonated and quaternary ammonium ions and salts thereof wherein:

Q is a linker that is an organic biradical which can be selected from optionally substituted arylene (e.g., —C$_6$H$_4$—), optionally substituted heteroarylene, optionally substituted alkylene chains, e.g., —(CH$_2$)p- where p is an integer indicating the length of the chain, or combinations thereof and wherein the alkylene may be a cycloalkylene;

Y for R$^1$ or R$^2$ is 0 to 6 with the total Y for both R$^1$ and R$^2$ in the phosphine reagent is at least 1; the total Y for both R$^1$ and R$^2$ is ranges most generally from 1-12, and more preferably from 1-6 or 2-4; and each R$_N$, independently, is selected from guanidine, alkyl, alkenyl, alkynyl, aryl, alkylaryl, arylalkyl or heteroaryl groups all of which are optionally substituted, wherein the two R$_N$ can be linked to form a 5-8 member ring which contains N and optionally contains one or more additional heteroatoms or which contains one or two oxy (—CO—) groups.

In specific embodiments, Q is cyclohexylene (—$C_6H_{10}$—) or an optionally substituted cylohexylene. In a specific embodiment, when Q is cycylohexylene, the —$N(R_N)_2$ groups are substituted in trans-positions with respect to the phosphorous on the cyclohexyl rings. In a specific embodiment when Q is cyclohexylene, the —$N(R_N)_2$ groups are substituted in cis-positions with respect to the phosphorous on the cyclohexyl ring. Each —$N(R_N)_2$ group is preferably substituted on a different carbon of the Q linker.

In specific embodiments, Q is an alkylene optionally substituted with one or more optionally substituted alkyl groups. Each —$N(R_N)_2$ group is preferably substituted on a different carbon of an alkylene Q linker. In specific embodiments, Q is an arylene, e.g. a phenylene. Each —$N(R_N)_2$ group is preferably substituted on a different carbon of the Q linker. When Q is an arylene, such as a phenylene, each —$N(R_N)_2$ group present is substituted on a different ring carbon. The Q linker can be substituted with one or more non-hydrogen substituents other than the —$N(R_N)_2$ group.

In specific embodiments, the linker Q has 4-12 carbon atoms, or 4-6 carbon atoms. In specific embodiments, the linker Q has 4-12 carbon atoms and Y is 1-4.

In specific embodiments of all formulas herein one or both of $R^1$ and $R^2$ can be independently selected from:

Structure VIb

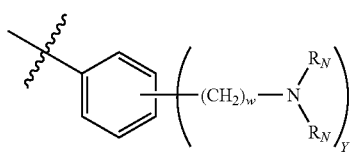

or protonated or quaternary ions or salt thereof where $R_N$ is as defined above; w is an integer ranging from 1-6, or 1, 2 3 or 4, Y is 1 or 2. In specific embodiments, one of $R^1$ or $R^2$ is a group of structure VIb and the other of $R^1$ or $R^2$ is an $R^1$ or $R^2$ group as defined herein, other than structure VIb. In a specific embodiment, the other of $R^1$ or $R^2$ is an unsubstituted phenyl group or a phenyl groups substituted with a non-hydrogen substituent other than that of structure VIb (i.e., other than an alkyl group substituted with an amino or ammonium). In a specific embodiment, both of $R^1$ and $R^2$ are a group of structure VIb. In specific embodiments, $R_N$ is hydrogen, an alkyl, an alkenyl, an alkynyl, an aryl, an arylalkyl or an alkylaryl group and two $R_N$ can be linked to form a 5-8 member ring which contains N and optionally contains one or more additional heteroatoms or which contains an oxy (—CO—) group. In specific embodiments, $R_N$ is a guanidine. In specific embodiments, $R_N$ is an alkyl group. In specific embodiments, $R_N$ is a straight-chain alkyl, branched alkyl or cycloalkyl. In specific embodiments, where $R^1$ and $R^2$ are groups of structure VI, Y for each ring is 1 or 2. Charged compounds can be in the form of salts with appropriate counter ions. In specific embodiments, $R_N$ are hydrogens or alkyl groups having 1-6 or 1-3 carbon atoms. In specific embodiments, the —$N(R_N)_2$ groups are substituted at meta (3 and/or 5-positions), para (4-position) or both meta and para (3, 4 and 5) positions on the ring.

In specific embodiments, the phopshine reagent of the invention is water-soluble. The phosphine reagents can be made water-soluble, for example, by choice of $R^1$, $R^2$, groups.

Water-soluble reagents include, among others, compounds of formula VII-1, VII-2 and VII-3:

VII-1

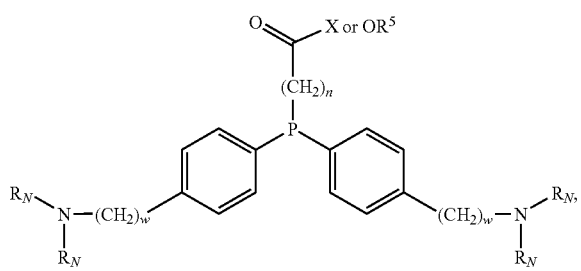

VII-2

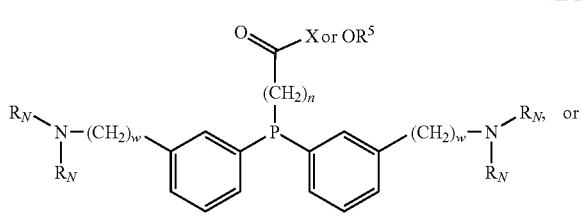

VII-3

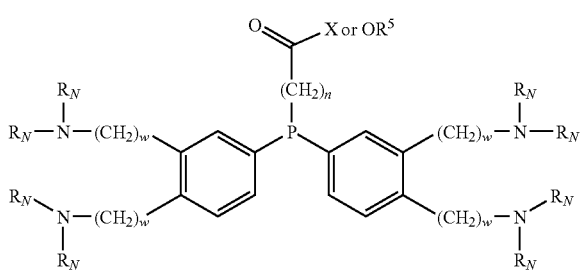

and protinated or quaternary cations and salts thereof where:

each w, independently, is an integer ranging from 1-6, each n, independently, is 1-6 and X, $R_N$ and $R_5$ are as defined herein. In specific embodiments, X is —$OR^5$ and each $R_N$, independently, is an alkyl group having 1-10, 1-6 or 1-3 carbon atoms or two $R_N$ (on the same substituent) can be joined together to form a 5- to 8-member heterocyclic ring having the N and optionally having one or two additional heteroatoms in the ring and optionally having one or two —CO— groups in the ring. Specific —$OR^5$ include —O—$N(R')_2$, or —$OSO_2$—R, as defined herein. Additional examples of activated ester groups include those in which $R^5$ is a nitro-substituted or halogenated phenyl group, particularly those having 3-6 halogens, including, for example, pentafluorophenyl and 2,4,6-triclorophenyl and 4-nitrophenyl groups. Additional —$OR^5$ also include

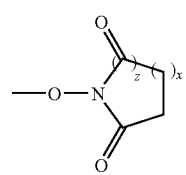

where z is 1 or 0 and when z is 1, x is 1-8 and when z is 0, x is 2 to 8.

In an embodiment, two $R_N$ are linked together to form a heterocyclic 6-member ring, such as:

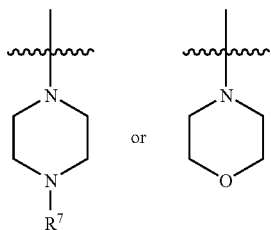

where $R^7$ is hydrogen or an optionally substituted alkyl, alkenyl, alkynyl, heterocyclic,
aryl or heteroaryl group. In specific embodiments, $R^7$ is an unsubstituted alkyl having 1-6 carbon atoms or 1-3 carbon atoms. In specific embodiments, $R^7$ is an optionally substituted phenyl group.

Tertiary phosphine reagents of the various formulas herein can be prepared by methods as described herein, by methods that are well-known in the art or by routine adaptation or modification of such methods by one of ordinary skill in the art. The following references can provide synthetic methods useful in the practice of this invention and as such are incorporated by reference herein: Tam, A. Soellner, M. B., Raines, R. T. 2007 "Water-Soluble Phosphinothiols for Traceless Staudinger Ligation and Integration with Expressed Protein Ligation," J. Amer. Chem. Soc., 129:11421-11430; Tam, A., Raines, R. 2009 "Coulombic effects on the traceless Staudinger ligation in water," *Bioorganic & Medicinal Chemistry* 17, 1055-1063; Tam, A. and "*Methods in Enzymology* 462, 25-44; Tam, A, Soellner, M. B., and Raines, R. T. 2008 "Electronic and steric effects on the rate of the traceless Staudinger ligation," *Organic & Biomolecular Chemistry* 6, 1173-1175; M. Regitz, G. Maas, *Diazo Compounds: Properties and Synthesis*, Academic Press, London, 1986, pp. 65-198; A. Padwa, M. D. Weingarten, *Chem. Rev.* 1996, 96, 223-269; M. P. Doyle, M. A. McKervey, T. Ye, *Modern Catalytic Methods for Organic Synthesis with Diazo Compounds*, John Wiley & Sons, New York, 1998; H. M. L. Davies, R. E. J. Beckwith, *Chem. Rev.* 2003, 103, 2861-2904; Z. Zhang, J. Wang, *Tetrahedron* 2008, 64, 6577-6605; E. Saxon, C. R. Bertozzi, *Science* 2000, 287, 2007-2010; B. L. Nilsson; L. L. Kiessling; R. T. Raines, *Org. Lett.* 2000, 2, 1939-1941; M. Köhn, R. Breinbauer, *Angew. Chem.* 2004, 116, 3168-3178; *Angew. Chem. Int. Ed.* 2004, 43, 3106-3116.

Compounds of formulas I, I-1, I-2, V, V-1, V-2, V-3, V-4 where X is a halogen or OH or $R^5$ is H are useful in the preparation of phosphine reagents of this invention, for example as illustrates in synthetic schemes herein including Scheme 8. Compounds of formulas I, I-1, I-2, V, V-1, V-2, V-3, V-4 where X is OH or $R^5$ is H can be converted to active esters of the phosphine reagents herein by various methods well-known in the art. Several such methods are exemplified herein and additional methods will be readily apparent to one of ordinary skill in the art. Additionally, certain active esters of formulas herein, including formulas I, I-1, I-2, V, V-1, V-2, V-3, V-4, can be used to synthesize alternative active esters employing art-recognized methods.

Methods for preparation of azides for use in the methods herein are known in the art. For example, azido derivatives of amino acids can be prepared by known methods (Lundquist, J. T., and Pelletier, J. C. (2001) "Improved solid-state peptide synthesis method utilizing alpha-azide-protected aminoacids. Org. Lett. 3:781-783.) In specific embodiments, the invention can be practiced with azido derivatives of any of the proteinogenic (or standard) L-amino acids, including L-selenocysteine and L-pyrrolylysine. Methods for formation of azido derivatives of peptides and proteins are known in the art. (See Tam, A., and Raines, R. T. (2009) Methods Enzymol. 462:25-44, and references therein.) An azido peptide can, for example, be formed via solid phase peptide synthesis. Azido sugars can be prepared by methods that are well-known in the art. For example exemplary azido sugars and methods for making them are described in Saxon E. et al 2002 J. Am. Chem, Soc. 124:14893-14902; Saxon E. et al. 2000 Science 287:2007-2010; Prescher et al. 2004 Nature 430:873-877; Laughler et al. 2007 Nat. Protoc. 2(11): 2930-2944; Laughler et al. (2009) Proc. Natl. Acad. Sci. (USA) 106(1):12-17; Bussink et al. 2007 J. Lipid Research 48(6):1417-1421.

In a specific embodiment, the invention provides a method for making a diazo compound by contacting an azide, particularly of formula IIa, with a phosphine reagent of formula I, in an appropriate solvent and optionally in the presence of water to form an azide, particularly a diazo compound of formula IV. The diazo compound may be formed in this step or it may be necessary to heat or add a base to the reaction mixture of the phosphine and the azide to form the diazo compound. The reaction can for example be carried out in a wet organic solvent the organic solvent is THF, dioxane, acetone, acetonitrile, dimethylformamide, dimethylsulfoxide or mixtures thereof. The reaction can be carried out in an anhydrous solvent, particularly toluene, or xylene. In a specific embodiment the reaction can be carried out in aqueous medium.

Base, if needed, will typically be added after initial reaction of the phosphine with the azide. In a specific embodiment, the base added is a non-nucleophilic base, for example, 1,8-Diazabicyclo[5.4.0]undec-7-ene (DBU). The initial reaction of phosphine reagent with azide can proceed for hours up to several days, prior to addition of base. However, more typically, the initial reaction is allowed to proceed for 1 to 24 hours prior to addition of base. The reaction is typically conducted at ambient temperature or below ambient temperature, for example between –15° to 45° C., or more typically between –5° to –30° C. It will however be appreciated by one of ordinary skill in the art that the temperature of the reaction can be optimized for given starting materials and to avoid undesired side-reaction. For example, it may be desirable to raise the temperature of the reaction to thermally fragment acyl triazene formed. The reaction is typically carried out at ambient pressure, but as will be appreciated by one of ordinary skill in the art can be carried out at any practically useful pressure. The reaction is typically carried out in an inert atmosphere (e.g., under argon or other inert gas).

In a specific embodiment, the reaction of the tertiary phosphine with the azide is carried out in a wet organic solvent. Without wishing to be bound by any particular mechanism, it is currently believed that water should be present at the beginning of the reaction, to prevent or limit premature fragmentation to the diazo-compound. Most generally, the term wet organic solvent refers to as much water as the solubility of the reactants and reagents will allow and yet still maintain homogenous solution of components. In specific embodiments, the wet solvent contains from 1% to about 20% by volume water. In additional embodiments, the wet solvent contains from 5% to 20% by volume water.

In a specific embodiment, the reaction of the tertiary phosphine and the azide is carried out in a polar aprotic solvent, which will not itself react with the phosphine, azide or reaction products, such as THF, dioxane or mixtures thereof. In an embodiment, the solvent is selected from acetone, acetonitrile, dimethylformamide or dimethylsulfoxide. The solvent is preferably wet.

In another embodiment, the reaction of the tertiary phosphine and the azide is carried out in anhydrous solvent, particularly a non-polar solvent, such as toluene or xylene, or lightly polar solvents, particularly those that are water immiscible, such as $CH_2Cl_2$. The reaction can also be carried out in anhydrous acetonitrile. Reaction performed in anhydrous solvent is preferably carried out at lower than ambient temperatures.

In another embodiment, the reaction is carried out in an aqueous medium, including water. In this embodiment, the tertiary phosphine is preferably water-soluble. In a specific embodiment conducted in aqueous medium, the azide is an azide of a biological molecule, for example, an azido sugar, an azido protein or an azidopeptide. In another specific embodiment conducted in aqueous medium, the azide is immobilized on tissue or on a cell, immobilized on or in a cell or is in a cell or is in an organism. For example, the azide, such as an azido sugar, may be in a cell membrane.

Certain phosphine reagents of the invention and formulas herein are water-soluble. The term "water soluble" refers to a compound that has a practically useful level of solubility in an aqueous medium such that the concentration of the compound in solution is sufficient to carry out a given reaction on a useful scale. In specific embodiments, water-soluble phosphine reagents include those that exhibit solubility of about 1 mM or more in aqueous medium (e.g., in water or in an aqueous buffer e.g., 0.4 M sodium phosphate buffer (pH 7.8)) at reaction temperatures. More preferably, water-soluble phosphine reagents exhibit solubility of 10 mM in water or in an aqueous buffer, e.g., a 0.4 sodium phosphate buffer (pH 7.8) at reaction temperatures.

The term "aqueous medium" refers to water or a solution where the solvent consists essentially of water. A small amount of organic solvent can be tolerated as long as the amount of such solvent does not interfere with the reaction or with the use of the reaction in a physiological environment. Aqueous media include water (of various purity levels, as known in the art) and "aqueous buffer solution" that is suitable to use for the reaction that keeps the pH in a desired range, preferably in a pH range useful for physiological environments and more specifically between 6.0-8.5. The reactions of this invention may also be carried out in miscible mixed aqueous-organic solvents, particularly where water is the predominant component of the solvent. Mixed aqueous-organic solvents include miscible mixtures of water and alcohol, where alcohols include, among others, methanol and ethanol. Miscible mixed aqueous-organic solvent systems preferably for use in this invention are those which can be used without significant detriment in a physiological environment. In specific embodiments, miscible mixed aqueous-organic solvent systems contain less than 10% by volume organic solvent. In specific embodiments, miscible mixed aqueous-organic solvent systems contain less than 5% by volume organic solvent. In specific embodiments, miscible mixed aqueous-organic solvent systems contain less than 1% by volume organic solvent.

The reaction can be carried out with approximately equimolar amounts of the phosphine and azide or the phosphine may be employed in excess (1-10% molar excess over the azide).

The invention is also directed to novel reagents of formula I which are useful for converting azides to diazo compounds or for the formation of acyl triazenes. In a specific embodiment, the invention provides novel compounds of formulas I-1 and I-2. In a more specific embodiment, the invention provides reagent of formula X where —O—N(R')$_2$ is: 2-oxopyrrolidinyl, 2,5-dioxo pyrrolidinyl, 2-oxopiperidinyl, or 2,6-dioxopiperidinyl. In a more specific embodiment, the invention provides reagents of formula X where n is 1 and —O—N(R')$_2$ is: 2,5-dioxo pyrrolidinyl or 2,6-dioxopiperidinyl.

The diazo compounds made by the methods herein can be employed using art known methods to make diazonium salts. Diazonium salts are the conjugate acids of diazo-compounds and so diazonium salts can be obtained by adding acid to the diazo compound. Alkyl-based diazonium salts, such as the example provided in Scheme 7, cannot be isolated. They can however to generated in situ and subsequently trapped. The acyl triazenes in this invention can be used to generate diazonium salts for in situ trapping. Aryl diazonium salts are often quite stable and can be isolated. Acyl triazenes derived from aryl azides (such as 8, Scheme 3), can fragment to diazonium salts under acidic conditions and certain of these diazonium salts can be isolated.

Acyl triazenes (III or IIIa) can in some cases be isolated from the reactions herein by precipitation. For example, after allowing the azide and the phosphine to react in THF/H$_2$O, a non-polar solvent can be added (such as diethyl ether) to induce precipitation of the acyl triazene (if it has not already completely fragmented thermally to diazo-compound). The acyl triazenes can also be isolated by silica gel column chromatography, but again some decomposition can occur in the process. In general acyl triazenes derived from aryl azides and alkyl azides (such as benzyl azides) are stable enough for column chromatography. Those azides bearing EWG groups may in some cases be too unstable for efficient isolation via column chromatography.

The invention also provides a method for making an acyl triazene compound which comprises the step of reacting a tertiary phosphine carrying a reactive carbonyl group with an azide. In a specific embodiment, the acyl triazene can be isolated.

In specific embodiments, the invention is directed to making an acyl triazene wherein the azide is an aryl or heteroaryl azide in which the azide group is bonded to the aryl or heteroaryl group and the aryl or heteroaryl group is optionally substituted.

The invention also provides acyl triazenes made by the method of this invention. In specific embodiments, the acyl triazene has the formula III-1:

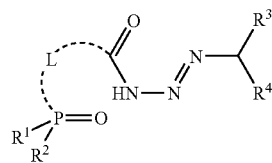

or more specifically has the formula III-2

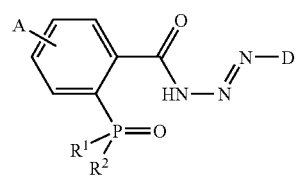

where L, $R^1$, $R^2$, $R^3$, $R^4$ are as defined herein, A indicates optional substitution on the indicated ring and D is an optionally substituted aryl or heteroaryl group. In a specific embodiment $R^4$ is EWG.

More specifically in formula III-1 and III-2, $R^1$ and $R^2$, independently, are optionally substituted alkyl, alkenyl, alkynyl, aryl, heteroaryl, heterocyclic, —OR', or —N(R")$_2$, where each R' and R" are independently hydrogen, or optionally substituted alkyl, aryl, heteroaryl or heterocylic, and wherein $R^1$ and $R^2$ together can form a 5- to 10-member ring containing the phosphorous atom; D is an optionally substituted aryl or heteroaryl group and A indicates optional substitution with 1-4 substituents on the indicated ring. In a more specific embodiment, D is an optionally substituted phenyl ring. In a more specific embodiment, A is selected from one to four hydrogens or halogens. In another specific embodiment, one or both or $R^1$ and $R^2$ is an optionally substituted phenyl ring.

The invention also provides reagent kits which comprise one or more reagents (of formula I) of this invention and which optionally include one or more azides, and one or more of solvents for carrying out the reaction, bases for fragmenting the acyl triazene, or instructions for carrying out the invention. Kits may also comprise reagent immobilized on a selected solid or one or more reagents for immobilizing the reagent upon a solid. The kits of this invention are useful for carrying out methods of this invention. A kit comprises one or more components in appropriate packing. A kit may contain one or more reagents, substrates, solvents or the like in appropriate containers in an amount sufficient to carry out one or more than one reaction. In a specific embodiment, a kit may contain all reagents and solvents for carrying out one or a plurality of reactions. In specific embodiments, in which the reagent is to be immobilized on a solid, the kit can contain precursors of the reagent for immobilization on the solid, reagents for carrying out immobilization and one or more solids for use in immobilization. In a specific embodiment, a kit may comprise one or more azido sugars in addition to one or more phosphine reagents of formula I, particularly water-solubel reagents of formula I.

Definitions

The term "immobilized" is used herein to refer to a bonding association of a chemical species to a solid. In the most general terms solid includes any inorganic surface or particle, non-soluble polymeric material (film, particle, bead or substrate surface) and further generally refers to human, animal, plant, bacterial, fungal, yeast or other tissue or cells in vivo, ex vivo or in vitro. The bonding association can be, among others, by adsorption, by any type of chemical bonding (covalent, ionic bonding, hydrophobic interaction, etc.) The bonding association can also be achieved by binding of two chemical species, e.g., a ligand with a ligand binding agent or species. Conventional art-known methods can be employed to achieve such immobilization. In a specific embodiment, an azide herein is a biological molecule, such as an azido sugar or an azido amino acid, peptide or protein, which can be immobilized by incorporation into tissue or cells by methods that are known in the art. For example, methods are known in the art for introducing azide groups into sugars, amino acids and peptides, and methods are known in the art for introducing such species into tissue and cells. More specifically, methods are known in the art for introducing azido sugars into tissue and cells, for example by metabolic labeling. See, for example, Saxon E. et al 2002 J. Am. Chem. Soc. 124:14893-14902; Saxon E. et al. 2000 Science 287:2007-2010; Prescher et al. 2004 Nature 430:873-877; Laughler et al. 2007 Nat. Protoc. 2(11): 2930-2944; Laughler et al. (2009) Proc. Natl. Acad. Sci. (USA) 106(1):12-17; Bussink et al. 2007 J. Lipid Research 48(6):1417-1421.

The term "leaving group", as used herein, is intended to take the general meaning that it has in the art to refer to a group which is part of and attached to a substrate molecule, but which on is displaced, for example, where the substrate molecule undergoes a displacement reaction, e.g., with a nucleophile. A good leaving group is a group that is readily displaced, which can be ascertained, at least in part, by observing the rate at which the reaction occurs or if there are competing processes occurring by the relative yield of the product of the displacement to that of products of the competing processes. It is recognized in the art that leaving groups differ in the ease with which they are displaced and so it is understood in the art that for a certain leaving groups are better than others as leaving groups.

Functional groups are classified in the art as electron-withdrawing or electron-donating groups with respect to their inductive effect on neighboring bonds compared to that of hydrogen. A number of EWG (electron-withdrawing groups) are known in the art and include among others, nitro, cyano, halogen, ammonium (—NR$_3^+$), aryloxy, alkoxy, sulfonic ester (—SO$_2$—R), —COOR, —COR, —CON(R)$_2$, —OCOR, alkylthio, arylthio, aryl, —C≡CR, and —C≡CR where each R is an optionally substituted alkyl, aryl, heterocyclic, or heteroaryl group.

The term linking diradical (linker) generally refers to an organic species that is bonded between two other chemical groups, species or moieties. Compounds of this invention may contain an L, an M or a P linker. The linker L herein is distinct from the linkers M and P herein in that the linkers M and P are organic species that link the reagent of formula I or an azide, respectively, to a selected solid surface. The terms $(L)_x$, $(M)_x$ or $(P)_x$ where x is 0 or 1 can be used to show the presence (x=1) or absence (x=0) of the linker.

The term "alkylene" refers to a diradical of a branched or unbranched saturated hydrocarbon chain, which unless otherwise indicated can have 1 to 12 carbon atoms, or 1-6 carbon atoms, or 2-4 carbon atoms. This term is exemplified by groups such as methylene (—CH$_2$—), ethylene (—CH$_2$CH$_2$—), more generally —(CH$_2$)$_n$— where n is 1-12 or preferably 1-6 or n is 1, 2, 3 or 4. —(CH$_2$)$_n$—, where n is 0 indicates the absence of the indicated linker. Alkylene groups may be branched, e.g., by substitution with alkyl group substituents. Alkylene groups may be optionally substituted as described herein. Alkylene groups may have up to two non-hydrogen substituents per carbon atoms. Preferred substituted alkylene groups have 1, 2, 3 or 4 non-hydrogen substituents.

The term "alkoxyalkylene" refers to a diradical of a branched or unbranched saturated hydrocarbon chain in which one or more —CH$_2$— groups are replaced with —O—, which unless otherwise indicated can have 2 to 30 carbon atoms, 2-20 carbon, 2-6 carbon atoms, or 2-4 carbon atoms. This term is synonymous with the term "ether linker." This term is exemplified by linkers such as —CH$_2$OCH$_2$—, —CH$_2$CH$_2$OCH$_2$CH$_2$—, —CH$_2$CH$_2$OCH$_2$CH$_2$OCH$_2$CH$_2$— and more generally —[(CR"$_2$)$_a$—O—]$_b$—(CR"$_2$)$_c$, where each R" independently is hydrogen, alkyl, halogen or other optional substitutent, a is 1-6, b is 1-6 and c is 1-10 or more preferably a and c are 1-4 and b is 1-3. Alkoxyalkylene groups may be branched, e.g., by substitution with alkyl group substituents.

The term "thioxyalkylene" refers to a diradical of a branched or unbranched saturated hydrocarbon chain in which one or more CH$_2$— groups are replaced with —S—, which unless otherwise indicated can have 2 to 30 carbon atoms, 2-20 carbon atoms, 2-6 carbon atoms, or 2-4 carbon atoms. This term is synonymous with the term thioether linker. This term is exemplified by linkers such as —CH$_2$SCH$_2$—, —CH$_2$CH$_2$SCH$_2$CH$_2$—, —CH$_2$CH$_2$SCH$_2$CH$_2$SCH$_2$CH$_2$— and more generally —[(CR"$_2$)$_a$—S—]$_b$—(CR"$_2$)$_c$, where each R" independently is hydrogen, alkyl, halogen or other substituent, a is 1-6, b is 1-6 and c is 1-10 or more, preferably a and c are 1-4 and b is 1-3. Thioxyalkylene linkers may be branched, e.g., by substitution with alkyl group substituents.

The term "aminoalkylene" refers to a diradical of a branched or unbranched saturated hydrocarbon chain in which one or more —CH$_2$— groups are replaced with —NH— groups or —NR'— groups (where each R' independently is hydrogen, alkyl, halogen or other substituent). Aminonalkylene linkers can have from 2-30 carbon atoms, 2-20 carbon atoms, 2-6 and 2-4 carbon atoms. Aminoalkylene linkers include those having the formula; —[(CH$_2$)$_a$—NR"—]$_b$—R", where each R" independently is H, an alkyl group or other substituent and where a is generally 1-6 and b is 1-6. More specifically, a can be 3 or 4 and b can be 1-4. Exemplary aminoalkylene linkers include among others the sperminyl linker (—(CH$_2$)$_3$—NH—(CH$_2$)$_4$—NH—(CH$_2$)$_3$—NH—), and the spermidinyl linker (—(CH$_2$)$_3$—NH—(CH$_2$)$_4$—NH—). Aminoalkylene linkers may be "carboxyaminealkylene linkers" which also contain one or more —CO— groups.

A specific "carboxyaminealkylene" linker is an "amidoalkylene" linker which refers to a diradical of a branched or unbranched saturated hydrocarbon chain in which one or more —CH$_2$— groups are replaced with an —CO—NR'— group (where each R' independently is hydrogen, alkyl, halogen or other substituent). Amidoalkylene linkers can have from 2-30 carbon atoms, 2-20 carbon atoms, 2-6,3-7 and 2-4 carbon atoms.

Alkylene groups —(CH$_2$)$_n$—, where n is 1-30, 1-20, 1-10, 1-6 or 1-3, include those having a carbon ring extending between two carbons of the alkylene, such as a cyclopentyl group:

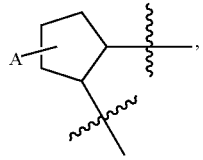

where A indicates optional substitution as defined herein on the ring.

One or more of the carbons of an alkylene linker are optionally substituted with non-hydrogen substituents.

Alkyleneoxy, alkylenethio and alkyleneamino linkers include those having carbocyclic and heterocyclic rings, such as:

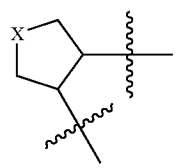

where X is —O—, —S—, —NH— or —NR—.

A linking diradical can also be formed from an aryl group or heteroaryl group, such are an arylene linker or heteroarylene linkers where the linker group is bonded through two bonds to the aryl or heteroaryl group, such as in

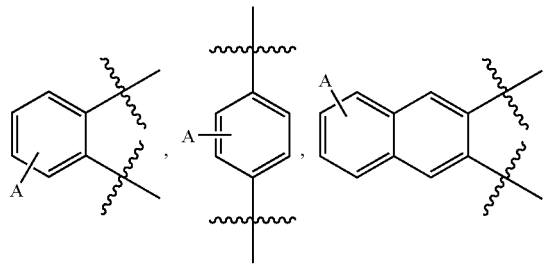

and the like

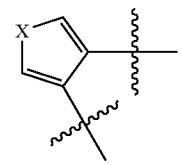

where X is O, S, NH or NR, A indicates optional substitution with one or more non-hydrogen substituents on the aryl ring(s). A linking diradical can also be formed from an alkyl substituted aryl or heteroaryl group, as for example:

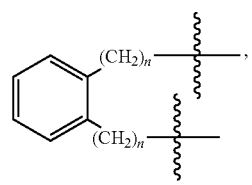

where n is 1-10, 1-6 or 1-3.

A linking diradical can also be formed from a heterocyclic group (a heterocyclene) where the linker group is bonded through two ring atoms in the heterocyclic ring. A heterocyclene contains at least one ring of atoms, which may be a saturated or unsaturated, but not aromatic. The ring contains at least two carbon atoms and one or more heteroatom (a non-carbon atom). To satisfy valence the heteroatom may be bonded to H or a substituent group. Heteroatoms include with —O—, —S—, —NR—, —N═, —PR—, or —POR among others. Preferred heteroatoms are O, S, or N. A heterocyclic ring typically contains from 3 to 10 ring member atoms. In specific embodiments, a heterocyclic ring contains 5-8 ring members and more specifically 5 and 6-ring members. A heterocyclic group may contain one or more rings, which may be linked through a bond or which may be fused. One or more carbons or heteroatoms (if chemically feasible) can be optionally substituted as defined below.

The term "alkyl" refers to a monoradical of a branched or unbranched (straight-chain or linear) saturated hydrocarbon and to cycloalkyl groups having one or more rings. Unless otherwise indicated alkyl groups have 1 to 30 carbon atoms, preferred alkyls have 1-22 carbon atoms. Shorter alkyl groups are those having 1 to 6 carbon atoms including methyl, ethyl, propyl, butyl, pentyl and hexyl groups, including all isomers thereof. Longer alkyl groups are those having 8-22 carbon atoms and preferably those having 12-22 carbon atoms, as well as those having 12-20 and those having 16-18 carbon atoms. The term "cycloalkyl" refers to cyclic alkyl groups having preferably 3 to 30 carbon atoms (preferably having 1-22 carbon atoms) having a single cyclic ring or multiple condensed rings. Cycloalkyl groups include among others those having 5, 6, 7, 8, 9 or 10 carbon ring members. Cycloalkyl groups include, by way of example, single ring structures such as cyclopropyl, cyclobutyl, cyclopentyl, cyclohexyl, cyclooctyl, and the like, or multiple ring structures such as adamantanyl, and the like. Unless otherwise indicated alkyl groups including cycloalkyl groups are optionally substituted as defined below. Specific substituted alkyl groups are aryl alkyl groups in which an alkyl group is substituted with one or more aryl groups. Exemplary arylalkyl groups are optionally substituted benzyl groups and phenethyl groups.

The term alkoxy refers to the group —OR where R is an alkyl group as defined above. Specific substituted alkoxy groups are halogenated alkoxy groups where the alkyl group of the alkoxy group is substituted with one or more halogens, including, among others, fluorinated alkoxy groups, perhalogenated alkoxy groups, perfluorinated alkoxy groups and more specifically trifluoromethoxy and pentafluoroethoxy groups.

The term alkylthio refers to the group —SR where R is an alkyl group as defined above.

The term oxoalkyl is used herein to refer generally to a group which contains one or more oxo (O=) moiety substituted on an alkyl group as defined above. Such groups may be derived formally from ketones R—CO—R, where each R is an alkyl or aryl group and at least one R is an alkyl group by removal of a hydrogen from an alkyl group, for example as in a 2-oxo-propyl group (CH$_3$—CO—CH$_2$—). Such groups may also be derived from cyclic alkyl groups, for example as in a 2-cyclopentyloxy group:

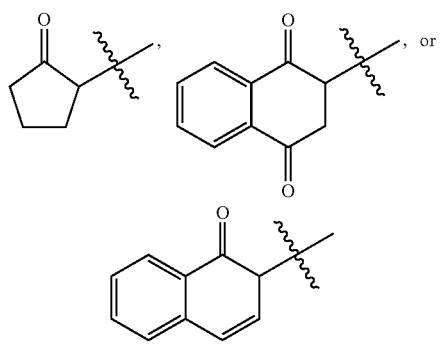

each of which may be optionally substituted. Additional examples of oxoalkyl groups include 2,4-dioxohexyl (CH$_3$CH$_2$COCH$_2$COCH$_2$—), 2-cyclohexyloxy, 2,4,-dioxy cyclopentyl, 2,5-dioxycyclohexyl, and 2-oxo-phenethyl:

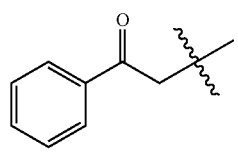 [SMILES: *CC(=O)c1ccccc1]

each of which may be optionally substituted. Additional examples include those in an alkyl group is substituted with an aryl ketone as in:

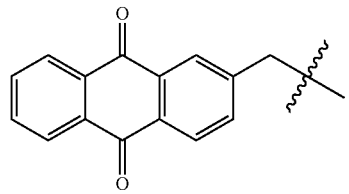 [SMILES: *Cc1ccc2c(c1)C(=O)c1ccccc1C2=O]

(anthroquinonylmethyl) which may be optionally substituted. Alkyl and aryl groups of oxoalkyl groups may be optionally substituted with groups other than oxo moieties.

The term "alkenyl" refers to a monoradical of a branched or unbranched unsaturated hydrocarbon group having one or more double bonds and to cycloalkenyl group having one or more rings wherein at least one ring contains a double bond. Unless otherwise indicated alkenyl groups have 1 to 30 carbon atoms and preferred alkenyl have 1-22 carbon atoms. Alkenyl groups may contain one or more double bonds (C=C) which may be conjugated or unconjugated. Preferred alkenyl groups are those having 1 or 2 double bonds and include omega-alkenyl groups. Shorter alkenyl groups are those having 2 to 6 carbon atoms including ethylene (vinyl), propylene, butylene, pentylene and hexylene groups including all isomers thereof. Longer alkenyl groups are those having 8-22 carbon atoms and preferably those having 12-22 carbon atoms as well as those having 12-20 carbon atoms and those having 16-18 carbon atoms. The term "cycloalkenyl" refers to cyclic alkenyl groups of from 3 to 30 carbon atoms having a single cyclic ring or multiple condensed rings in which at least one ring contains a double bond (C=C). Cycloalkenyl groups include, by way of example, single ring structures (monocyclic) such as cyclopropenyl, cyclobutenyl, cyclopentenyl, cyclohexenyl, cyclooctenyl, cylcooctadienyl and cyclooctatrienyl as well as multiple ring structures. Cycloalkenyl groups include among others those having 5, 6, 7, 8, 9 or 10 carbon ring members. Unless otherwise indicated alkyl groups including cycloalkyl groups are optionally substituted as defined below.

The term alkenyloxy refers to the group —OR where R is an alkenyl group as defined above.

The term alkenylthio refers to the group —SR where R is an alkenyl group as defined above.

The term oxoalkenyl is used herein to refer generally to a group which contains one or more oxo (O=) moieties substituted on an alkenyl group as defined above.

The term "alkynyl" refers to a monoradical of an unsaturated hydrocarbon having one or more triple bonds (C≡C). Unless otherwise indicated preferred alkyl groups have 1 to 30 carbon atoms and more preferred are those that contain 1-22 carbon atoms. Alkynyl groups include ethynyl, propargyl, and the like. Short alkynyl groups are those having 2 to 6 carbon atoms, including all isomers thereof. Long alkynyl groups are those having 8-22 carbon atoms and preferably those having 12-22 carbon atoms as well as those having 12-20 carbon atoms and those having 16-18 carbon atoms. The term "cycloalkynyl" refers to cyclic alkynyl groups of from 3 to 30 carbon atoms having a single cyclic ring or multiple condensed rings in which at least one ring contains a triple bond (C≡C). Unless otherwise indicated alkynyl groups including cycloalkynyl groups are optionally substituted as defined below.

The term alkynyloxy refers to the group —OR where R is an alkynyl group as defined above.

The term alkynylthio refers to the group —SR where R is an alkynyl group as defined above.

The term oxoalkynyl is used herein to refer generally to a group which contains one or more oxo (O=) moieties substituted on an alkynyl group as defined above.

The term "carbocyclic" generically refers to a monoradical that contains a carbon ring which may be a saturated ring (e.g., cyclohexyl) or unsaturated (e.g., cyclohexenyl), but is not aromatic (e.g., the term does not refer to aryl groups). Ring structures have three or more carbon atoms and typically have 3-10 carbon atoms. As indicated above for cycloalkane, cycloalkenes and cycloakynes, alicyclic radical can contain one ring or multiple rings (bicyclic, tricyclic etc.). One or more carbons of a carbocyclic group can be optionally substituted as defined herein.

The term "aryl" refers to a monoradical containing at least one aromatic ring. The radical is formally derived by removing a H from a ring carbon. Aryl groups contain one or more rings at least one of which is aromatic. Rings of aryl groups may be linked by a single bond or a linker group or may be fused. Exemplary aryl groups include phenyl, biphenyl, naphthyl, fluorenyl groups as well as groups formed from anthracene, phenanthrene, azulene, and acenaphthalene. Aryl groups include those having from 6 to 30 carbon atoms and those containing 6-12 carbon atoms. Unless otherwise noted aryl groups are optionally substituted as described herein. Specific substituted aryl groups are alkylaryl groups in which an aryl group is substituted with one or more alkyl groups. Exemplary alkylaryl groups are optionally substituted xylyl and toluoyl groups (e.g., formed from various xylene isomers and toluene, respectively).

The term aryloxy refers to the group —OR where R is an aryl group as defined above.

The term aryllthio refers to the group —SR where R is an aryl group as defined above.

The term oxyaryl is used herein to refer generally to a group which contains one or more oxo (O=) moiety substituted on an alkyl group as defined above. Such groups may be derived formally from ketones R—CO—R, where R can be alkyl or aryl groups and at least one R is an aryl group by removal of a hydrogen from an aryl group, for example as in phenyl groups substituted with oxoalkyl groups, e.g.:

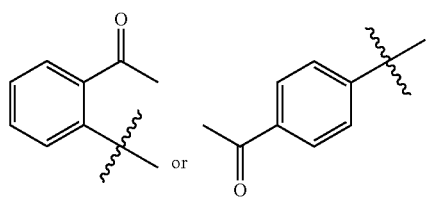

each of which may be optionally substituted. Alkyl and aryl groups of oxoaryl groups may be optionally substituted with groups other than oxo moieties.

The term aminooxy refers generally to the group —O—N(R)2 where R is an alkyl or aryl group as defined above. The term also refers to cyclic aminooxy groups where the N is in a ring, as, for example, in the following groups:

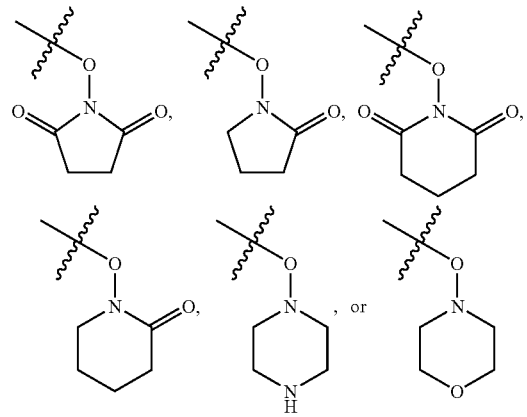

which may be optionally substituted.

The term "heterocyclic" generically refers to a monoradical that contains at least one ring of atoms, which may be a saturated or unsaturated, but not aromatic, wherein one or more carbons of the ring are replaced with a heteroatom (a non-carbon atom). To satisfy valence the heteroatom may be bonded to H or a substituent group. Heteroatoms include with —O—, —S—, —NR—, —N=, —PR—, or —POR among others. Preferred heteroatoms are O, S, or N. A heterocyclic ring typically contains from 3 to 10 ring member atoms. In specific embodiments, a heterocyclic ring contains 5-8 ring members and more specifically 5 and 6-ring members. A heterocyclic group may contain one or more rings, which may be linked through a bond or which may be fused. One or more carbons or heteroatoms (if chemically feasible) can be optionally substituted as defined below. Heterocyclic groups for example, include among others, 2-pyrrolinyl, 2,4-imidazolidinyl, 2,3-pyrazolidinyl, 2-piperidyl, 3-piperidyl, 4-piperdyl, and 2,5-piperzinyl and morpholinyl groups, including 2-morpholinyl and 3-morpholinyl groups.

The term "heteroaryl" refers to a group that contains at least one aromatic ring in which one or more of the ring carbons is replaced with a heteroatom (non-carbon atom). To satisfy valence the heteroatom may be bonded to H or a substituent groups. Ring carbons may be replaced with —O—, —S—, —NR—, —N=, —PR—, or —POR among others, where R is an alkyl, alkenyl, alkynyl, aryl, heterocyclic or heteroaryl group. Heteroaryl groups may also include one or more aryl groups (carbon aromatic rings). Heteroaromatic and aryl rings of the heteroaryl group may be linked by a single bond or a linker group or may be fused. Heteroaryl groups include those having aromatic rings with 5- or 6-member rings where 1-3 ring atoms are heteroatoms. Preferred heteroatoms are —O—, —S—, —NR— and —N=. Heteroaryl groups include those containing 6-12 carbon atoms. Unless otherwise noted, carbon atoms and heteroatoms (if chemically feasible) of heteroaryl groups are optionally substituted as described herein. Examples of heteroaryl groups include, but are not limited to, systems (as numbered from the linkage position assigned priority 1), such as 2-pyridyl, 3-pyridyl, 4-pyridyl, 2,3-pyrazinyl, 3,4-pyrazinyl, 2,4-pyrimidinyl, 3,5-pyrimidinyl, 2,3-pyrazolinyl, 2,4-imidazolinyl, isoxazolinyl, oxazolinyl, thiazolinyl, thiadiazolinyl, tetrazolyl, thienyl, benzothiophenyl, furanyl, benzofuranyl, benzoimidazolinyl, indolinyl, pyridizinyl, triazolyl, quinolinyl, pyrazolyl, and 5,6,7,8-tetrahydroisoquinoline.

The term heteroaryloxy refers to the group —OR where R is an aryl group as defined above.

The term heteroarylthio refers to the group —SR where R is an aryl group as defined above.

The term "amino" refers generically to a —N(R")2 group wherein each R", independently, is hydrogen, alkyl, alkenyl, alkynyl, aryl, heterocyclic, or heteroaryl radical as described above. Two of R" may be linked to form a heterocyclic ring containing at least one nitrogen. An "alkyl amino" group refers to an amino group wherein at least one R" is alkyl. An "aryl amino" group refers to an amino group wherein at least one R" is aryl. Amino groups may contain aryl and alkyl groups.

The term "amido" refers generically to an —CO—N(R")2 group wherein R" independently of other R" is hydrogen, alkyl, alkenyl, alkynyl, aryl, heterocyclic, or heteroaryl radical as described above. Two of R" may be linked to form a ring. An "alkyl amido" group refers to an amido group wherein at least one R" is alkyl. An "aryl amido" group refers to an amido group wherein at least one R" is aryl. Amido groups may contain both aryl and alkyl groups.

The term "aminoacyl" group" refers generically to an —NR"—CO—R" group wherein R' independently of other R' is hydrogen, alkyl, alkenyl, alkynyl, aryl, heterocyclyl, or heteroaryl radical as described above. Two of R" may be linked to form a ring. An "alkyl aminoacyl" group refers to an aminoacyl group wherein at least one R" is alkyl. An "aryl amido" group refers to an aminoacyl group wherein at least one R" is aryl.

The term "alkoxyalkyl" (also called an ether group) refers to an alkyl group in which one or more —CH2- groups are replaced with —O. Unless otherwise specified preferred alkoxyalkyl groups have from 2 to 10 carbon atoms and more preferably have 3 to 6 carbon atoms. Alkoxyalkyl groups include groups of the formula: —[(CH2)a-O-]b-CH3 where a is 1-10 and b is 1-6.

The term "thioxyalkyl" (also called a thioether group) refers to an alkyl group in which one or more —CH2- groups are replaced with —S—. Unless otherwise specified, preferred thioxyalkyl groups have from 3 to 30 carbon atoms and more preferably have 6 to 22 carbon atoms. Thioalkoxylalkyl groups include groups of the formula: [(CH2)a-S-]b-CH3 where a is 1-10 and b is 1-6. Alkoxyalkyl, thioalkoxyalkyl and dithioalkoxyalkyl groups can be branched by substitution of one or more carbons of the group with alkyl groups.

The term "sulfonyl" refers to the radical —SO2-R' where R' is an alkyl, alkenyl, alkynyl, aryl, heterocyclic, or heteroaryl radical as described above.

The term "sulfonate" refers to the radical —SO3-R" where R" is hydrogen, alkyl, alkenyl, alkynyl, aryl, heterocyclyl, or heteroaryl radical as described above. An "alkyl sulfonate" group refers to a sulfonate group wherein R" is alkyl. An "aryl sulfonate" group refers to a sulfonate group wherein at least one R" is aryl. The group —SO3H can be in the ionic form —SO3—.

A triazene generically refers to a compound of having a —NR'—N=N—R' group, where each R', independently, is hydrogen, alkyl, alkenyl, alkynyl, aryl, heteroaryl, heterocyclic, or carbocyclic group, each of which groups can be optionally substituted. An acyl triazene is a compound as in FIG. 2 or Scheme 1, having the group —CO—NR'—N=N—R' where each R' is as for the triazene.

The term protecting groups is used herein as broadly as the term is used in the art to refer to a chemical group that is introduced into a molecule by reaction with a function group to protect that function group from further reaction under a given set of reaction conditions, but which can be selective removed (by deprotection) to regenerate that functional group when protection is no longer needed or desired. The protecting group is selected as is well-known in the art for ease of addition to and removal from (protection and deprotection of) a given functional group and to be non-reactive (i.e., protective) under conditions in which protection is desired. A wide variety of protective groups is known in the art. See, for example, P. G. M. Wuts and T. W. Greene (2006) Greene's Protective Groups in Organic Synthesis, 4th Ed. (Wiley-Interscience) and P. J. Kocienski (2005) Protecting Groups, 3rd Ed. (Georg Thieme Verlag, New York, which provide a description of protecting groups for various functional groups and also provide a description of reagents for introduction of protecting groups and a description of how deprotection is achieved. These references are specifically incorporated by reference herein for the structure of protecting groups (particularly amine protecting groups) and for methods for protecting and deprotecting functional groups including amines. Protective groups are often classified for the group which they protect, for example, the term amine protecting group refers to a protecting group that can be introduced into a molecule carrying an amine functional group to protect the amine group. In this case, the protecting group is bonded to the nitrogen of the amine to form —NR—PR, where PR is the protecting group and R is any other appropriate atom or group (e.g., hydrogen, alkyl group, aryl group etc.). Other classes of protecting groups include alcohol protecting groups, carbonyl protecting groups or carbonylic acid protecting groups. It is understood in the art, that a given protecting group may be useful for protecting different functional groups. In specific embodiments, herein, compounds of the invention may contain one or more protecting group. In more specific embodiments, compounds of the invention may contain protected amine functional groups —NR—PR, where PR is an amine protecting group. Amine protecting groups as is well-known in the art include among other: RP1-O—CO— or RP1-CO— (where RP1 is, for example, certain optionally substituted alkyl and aryl groups, including alkyl, fluorinated alkyl, methyl, trifluoromethyl, t-butyl, benzyl, p-methoxybenzyl, fluorinated benzyl or fluorenylmethyl); RP2- groups (where RP2 is, for example, an optionally substituted benzyl or phenyl group, including, among others, benzyl, p-methoxybenzyl, 3,4-dimethoxybenzyl, or p-methoxypheny; or a trityl group which is optionally substituted, for example with alkyl or alkoxy groups); or RP3-SO2-O— (where RP3 is an aryl or substituted aryl group, particularly a substituted phenyl group, for example, p-methylphenyl, p-bromophenyl, p-nitorphenyl, or 2-nitrophenyl).

Alkyl, alkenyl, alkynyl, aryl, heteroaryl, heterocyclic, carbocyclic, and diradical linkers as noted above are optionally substituted. Optional substitution means substitution, unless otherwise noted, by one or more non-hydrogen substituents. Halogens (e.g., Br—, I—, Cl—, F—), nitro groups (NO2-), cyano (NC—), isocyano (CN—), thiocyano ((NCS—), isothiocyano (SCN—), sulfuryl (SO2-), —N(R')2,
—COR', —COOR', —CON(R')2, —NR'—CO—N(R')2-, —CO—SR', —OR', or —SR' (where each R', independently, is hydrogen, alkyl, alkenyl, alkynyl, aryl, heteroaryl, heterocyclic groups), alkyl, alkenyl, alkynyl, aryl, heteroaryl, or heterocyclic groups. In certain embodiments, optional substitution includes substitution with azide groups. Alkyl, alkenyl, alkynyl, aryl, heteroaryl and heterocyclic substituent groups may in turn be substituted with one or more optional substituents, particularly one or more halogens, nitro, cyano, isocyano, thiocyano, isothiocyano, sulfuryl, —N(R')2, —OR', or —SR' groups. Additional exemplary substituents include —CF3, -pentafluorphenyl or other halogenated alkyl or aryl groups. In specific embodiments phenyl groups may be substituted with 1, 2, 3, 4 or 5 substituent groups. In a specific embodiment, alkyl groups are substituted with 1 or 2 of these substituent groups. In a specific embodiment, phenyl rings have a single substituent group (e.g., a nitro, cyano, isocyano, thiocyano, isothiocyano, or sulfuryl) in the para-position.

Optional substitution refers generally to optional substitution of any carbon of any variable with one or more than one non-hydrogen substituent, such that the substitution is compatible with the chemistry that is to be carried out in the methods of the invention. For example, disulfide and peroxide substituents are not preferred. More specifically optional substitution refers to substitution of one or more carbons of any alkyl, alkenyl, alkynyl, aryl, heteroaryl, heterocyclic ring, carbocyclic ring, substituent group or linker group herein. Additionally, any N, O, P or S atoms of the groups, linkers and substituents herein can be optionally substituted with a non-hydrogen substituent as is chemically feasible and as is compatible with the chemistry that is to be carried out in the methods of this invention. In specific embodiments, alkyl, alkenyl, alkynl, aryl, heterocyclic, carbocyclic and heteroaryl groups herein can be substituted with one or more halogens, hydroxy, thiol, alkyl, aryl, alkoxy, aryloxy, cyano, or isocyano. In specific embodiments, optional substitution includes substitution with one or more azide groups.

Optional substitution also encompasses substitution with protected functional groups. A substituent group may be reactive under the reaction conditions of this invention and may be protected employing art-known techniques and protecting groups to avoid reaction. In a given substrate, reagent or product of the methods of this invention, a substitutent may be protected because that protection was needed in the preparation of the substrate or reagent or will be needed in further reaction of a product of the reaction of this invention. One of ordinary skill in the art can readily select protecting groups appropriate for protection of reactive substituents and functional groups. As noted above, in specific embodiments, —$NH_2$ groups may be protected as known in the art with amine protecting groups.

Alkyl, alkenyl, and alkynyl groups may be optionally substituted as described herein and may contain non-hydrogen substituents dependent upon the number of carbon atoms in the group and the degree of unsaturation of the group. Unless otherwise indicated substituted alkyl, alkenyl, alkynyl, aryl, heterocyclic and heterocyclyl groups preferably contain 1-10, and more preferably 1-6, and more preferably 1, 2 or 3 non-hydrogen substituents.

As to any of the above groups or linkers which contain one or more substituents, it is understood, that such groups or linkers do not contain any substitution or substitution patterns which are sterically impractical and/or synthetically non-feasible. In addition, the compounds of this invention include all stereochemical isomers arising from the substitution of these compounds.

In general descriptions of reagents or reactions products herein a chemical species may be described as "containing, "carrying" or "bearing" a particular atom or chemical moiety or group (e.g., a N atom or a —CO— group). This description is intended to indicate that the listed atom, moiety or groups is covalently linked to other atoms or groups within the chemical species. For example, an R3 group containing an EWG group indicates that an EWG group is covalently linked to other atoms (determined by the definition of R3) within the R3 group or is formed by covalent linkage of atoms in that chemical species.

When a group of substituents is disclosed herein, it is understood that all individual members of those groups and all subgroups, including any isomers and enantiomers of the group members are disclosed separately. When a compound is claimed, it should be understood that compounds known in the art including the compounds disclosed in the references disclosed herein are not intended to be included in the claim. When a Markush group or other grouping is used herein, all individual members of the group and all combinations and subcombinations possible of the members of the groups therein are intended to be individually included in the disclosure. Every formulation or combination of components described or exemplified herein can be used to practice the invention, unless otherwise stated.

Specific names of compounds are intended to be exemplary, as it is known that one of ordinary skill in the art can name the same compounds differently.

When a compound is described herein such that a particular isomer, enantiomer or diastereomer of the compound is not specified, for example, in a formula or in a chemical name, that description is intended to include each isomer and enantiomer of the compound described individually or in any combination (e.g., cis/trans isomers, R/S enantiomers). The compounds of this invention may contain one or more chiral centers. Accordingly, this invention is intended to include racemic mixtures, non-racemic mixtures enriched in one or more steroisomer. The invention is intended to include individual enantiomers and diastereomers substantially free (less than 95% and preferably less than 99% by weight) of other enantiomers and/or diastereomers.

Additionally, unless otherwise specified, all isotopic variants of compounds disclosed herein are intended to be encompassed by the disclosure. For example, it will be understood that any one or more hydrogens in a molecule disclosed can be replaced with deuterium or tritium. Isotopic variants of a molecule are generally useful as standards in assays for the molecule and in chemical and biological research related to the molecule or its use. Isotopic variants may also be useful in diagnostic assays and in therapeutics. Methods for making such isotopic variants are known in the art.

Molecules disclosed herein contain one or more ionizable groups [groups from which a proton can be removed (e.g., —COOH) or added (e.g., amines) or which can be quaternized (e.g., amines)]. Additionally certain compounds of the invention may be cationic or anionic, e.g., contain cationic sulfonium or phosphonium groups. It is understood that such compounds can be in the form of salts with appropriate counterions. All possible ionic forms of such molecules and salts thereof are intended to be included individually in the disclosure herein. With regard to salts of the compounds herein, one of ordinary skill in the art can select from among a wide variety of available counterions those that are appropriate for preparation of salts of this invention for a given application. In specific applications, the selection of a given anion or cation for preparation of a salt may result in increased or decreased solubility of that salt. Exemplary anions for such salts include halides (e.g., Cl—, Br—), carboxylates (e.g., R—CO2-, where R is optionally substituted alkyl or aryl). Exemplary cations for such salts include alkali metal cations (e.g., Na+, K+, etc.), alkaline earth cations (e.g., Mg2+, Ca2+, etc.), ammonium cations N(R)4+, where each R is H, optionally substituted alkyl or aryl (e.g., NH4+, N(CH$_3$)4+.

Every formulation or combination of components described or exemplified herein can be used to practice the invention, unless otherwise stated.

Whenever a range is given in the specification, for example, a temperature range, pressure range, a time range, a range of values for a given variable, or a composition or concentration range, all intermediate ranges and subranges, as well as all individual values included in the ranges given are intended to be included in the disclosure. Unless otherwise noted all ranges noted herein are inclusive of the lower and upper range value listed. It will be understood that any subranges or individual values in a range or subrange that are included in the description herein can be excluded from the claims herein.

One of ordinary skill in the art will appreciate that synthetic methods, starting materials, reagents, reaction conditions, methods of purification, and assay methods other than those specifically exemplified can be employed in the practice of the invention without resort to undue experimentation. All art-known functional equivalents, of any such methods and materials are intended to be included in this invention.

The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by examples, preferred embodiments and optional features, modification and variation of the concepts herein disclosed may be resorted to by those skilled in the art, and that such modifications and variations are considered to be within the scope of this invention as defined by the appended claims.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. Any recitation herein of the broad term "comprising", particularly in a description of components of a composition or in a description of elements of a device, is intended to encompass and describe the terms "consisting essentially of" or "consisting of".

Although the description herein contains many specificities, these should not be construed as limiting the scope of the invention, but as merely providing illustrations of some of the embodiments of the invention. All references cited herein are incorporated by reference herein in their entirety. However in the event of inconsistency between a cited reference and the specification, the specification is to be given preference except in the event of obvious clerical or typographic error in the specification. Some references provided herein are incorporated by reference herein to provide details concerning additional starting materials, additional reagents (e.g., strong bases), additional methods of synthesis, additional methods of purification, additional methods of analysis and additional uses of the invention.

Results and Discussion with Respect to Specific Embodiments

In order to determine if triazene and ultimately diazo compounds could be produced by the reaction of certain phosphines with azide, we have specifically investigated the reaction of azido glycine derivative 2a with a series of phosphines that contained ester substituents of increasing leaving-group ability (Scheme 2). As expected, the reaction of azide 2a and phosphinoester 1a, the latter being of the type used in a Staudinger ligation, provided the amide 3 as the predominant product (~90% yield). Early success was achieved with phosphinothioester 1b: upon allowing the reaction mixture to stir beyond the time necessary for complete consumption of the phosphine, the solution gradually turned a yellow color, indicative of the presence of diazo-compound. Chromatography and subsequent analysis confirmed the presence of diazo-compound 5a (30% yield) along with primary amide 4 (33% yield) and Staudinger ligation product 3 (60% yield). Ultimately, using phosphine-N-hydroxysuccinimyl ester 1c, conditions were developed that provided diazo-compound 5a in excellent yield. For this particular combination, a white precipitate formed after a few hours in 1,4-dioxane/H2O or THF/H2O solvent mixtures. Upon allowing the mixture to stir for a few days, the suspension eventually gave way to a clear yellow solution. After some experimentation, we found that treating the suspension with sat. aq. NaHCO3 or NEt3 (2 equiv), facilitated the formation of the diazo-compound within minutes.

The aforementioned white precipitate and presumed precursor to the diazo-compound was tentatively characterized as acyl triazene 6 (Scheme 2). The 1H NMR spectrum of the intermediate, acquired in CDCl3 at 25° C., was broad and exhibited a conspicuous downfield signal at ~13.4 ppm. Lowering the temperature to ~6° C. led to decoalescence and sharpening of the spectrum to reveal a pair of isomers, in a ratio of 3:1, exhibiting downfield signals at ~13.5 ppm and ~12.8 ppm, respectively, that disappear following a "D2O shake". Acyl alkyl-triazenes and alkyl aryl-triazenes are known to exist in solution as a mixture of tautomers, wherein the acidic proton resides on either terminus of the triazene moiety.[14f, 17] Unfortunately, we failed in our attempts to obtain crystals of the intermediate that were suitable for X-ray crystallography, due in part to its thermal instability. When, however, aryl azide 7 was allowed to react with phosphine 1c, acyl triazene 8 was isolated in excellent yield by column chromatography, and its structure was confirmed by X-ray crystallography (Scheme 3). The 1H NMR spectrum of acyl triazene 8 exhibited a downfield signal at ~12.9 ppm, providing strong evidence that the asserted precursor to diazo-compound 5a is indeed acyl triazene 6.

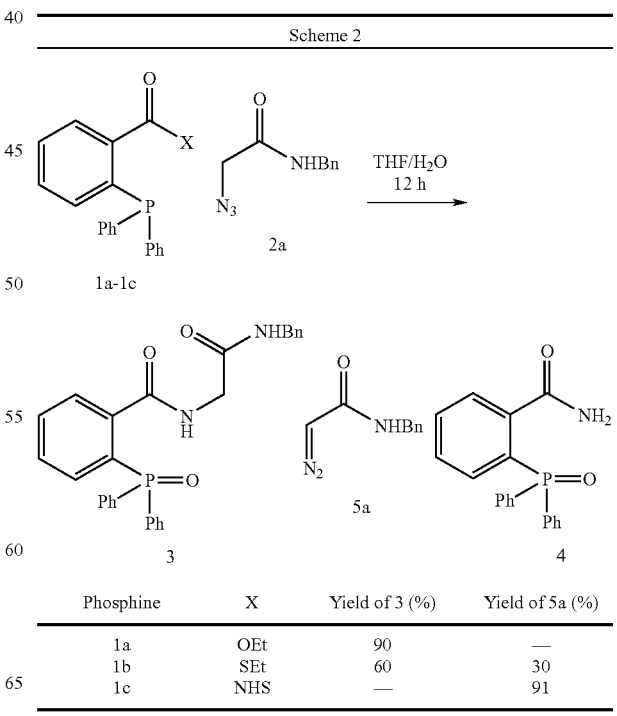

Scheme 2

| Phosphine | X | Yield of 3 (%) | Yield of 5a (%) |
|---|---|---|---|
| 1a | OEt | 90 | — |
| 1b | SEt | 60 | 30 |
| 1c | NHS | — | 91 |

Although the yield of diazo-compound 5a from azide 2a was satisfactory, the rate of reaction was unacceptably low. By following the progress of the reaction of 1c and 2a by 31P NMR spectroscopy, we observed that only 50% conversion to acyl triazene 6 was achieved after 100 min. We attributed this low reaction rate to delocalization of electron density from the phosphorous atom into the electron-deficient aromatic ring, thereby slowing down its addition to the azide. Accordingly, we designed an alternative reagent in which the phosphine and activated-ester moieties were not in conjugation. Phosphine 1e (Scheme 4), prepared in excellent yield by 1,4-addition of diphenylphosphine to methyl acrylate followed by saponification and carbodiimide-mediated esterification, reached 50% conversion in its reaction with 2a after just 20 min. Hence, phosphine 1e is a preferred reagent for mediating the conversion of an azide to a diazo-compound.

Scheme 3

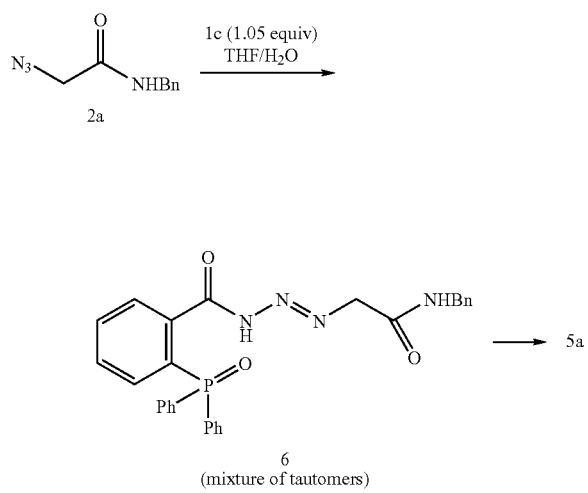

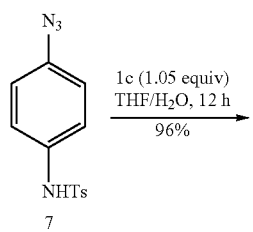

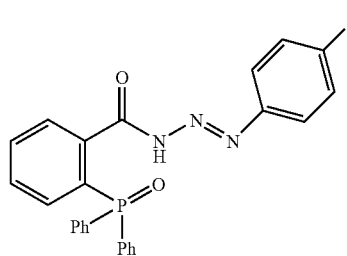

structure confirmed by X-ray crystallography

Scheme 4

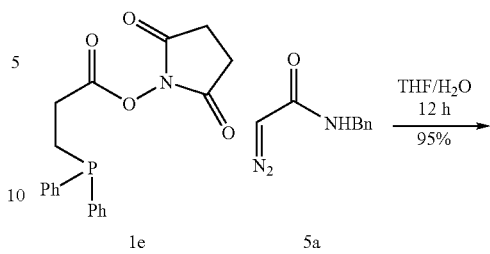

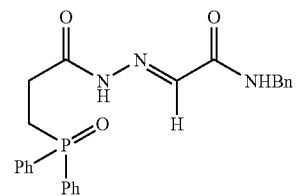

Conducting the reaction in a wet solvent (THF/H2O) and using near equimolar amounts of phosphine (1.05 equiv) were found to be crucial for effectuating good conversion to diazo-compound. When the reaction of azide 2a was conducted under anhydrous conditions (e.g., in CH2Cl2), diazo-compound 5a was formed quickly in situ, presumably via fragmentation of the putative acyl triazenophosphonium salt (FIG. 2 and Scheme 1). Unfortunately, although the phosphine was consumed completely, the yield of diazo-compound 5a was moderate (~50%) and a substantial amount of the azide starting material was reisolated (~10-15%). Subsequent investigation revealed the origin of the diminished conversion: phosphine 1e (and 1c) reacted with diazo-compound 5a at a rate that was comparable to that of its reaction with azide 2a to give a compound whose spectroscopic data were consistent with acyl hydrazone 9 (Scheme 4).[14a, 18] Under wet conditions and preceding basic workup, the thermal decomposition of acyl triazene 6 (the hydrolysis product of the acyl triazenophosphonium salt) is slow, allowing near complete consumption of azide and phosphine before accumulation of appreciable concentrations of the diazo-compound.

The mechanism of fragmentation of acyl triazene 6 under thermal conditions presumably involves scission of the pertinent N—N bond to give the diazonium salt and the conjugate base of primary amide 4 (4-CB) followed by proton transfer to give diazo-compound 5a and 4 (Scheme 5). As acyl triazene 6 is likely to be relatively acidic, the fragmentation might be acid-catalyzed and thus autocatalytic.[19] In a basic environment, the acyl triazene 6 would exist primarily as its conjugate base (6-CB), albeit in equilibrium with 6. Deprotonation of 6 at the α-carbon would give the alternative conjugate base 6-CB'. In a manner reminiscent of the Bamford-Stevens reaction—the base catalyzed fragmentation of p-toluenesulfonylhydrazones[7a]—such a species could undergo N—N scission to give diazo-compound 5a. Alternatively, unstable 6-CB' could arise directly from 6-CB via an intramolecular proton transfer. For certain substrates the latter might be a contributory pathway under the conditions prior to basic workup (vide infra).

The scope of the reductive fragmentation reaction was found to be quite general. Using phosphine 1e, a-azido esters and lactones (2d-g, Scheme 6) were converted to their diazo-compound derivatives in excellent yield. As complete consumption of the azide was achieved within a few hours and the side products were relatively polar (primary amide, hydrolyzed phosphine reagent, and/or trace amounts of hydrazone), short-path column chromatography was sufficient in providing diazo-compound in excellent purity. a-Azido ketones proved to be problematic due to the difficulty of avoiding pre-workup fragmentation to a diazo-compound and subsequent reaction to form an acyl hydrazone, as in Scheme 4. Nevertheless, α-diazo cyclohexanone 5h and α-diazo acetophenone 5i were obtained in yields of 67% and 49%, respectively. For the latter, conducting the reaction in anhydrous toluene followed by column chromatography proved to be slightly superior with respect to yield. In addition to the glycine derivative 2a, other azido-amides were found to be excellent substrates. For example, the azido-amide derivative of phenylalanine 2b was transformed to diazo-compound 5b in 81% yield. It was observed that a prolonged basic workup (sat. aq. NaHCO3, overnight) was required for fragmentation of the putative triazene, presumably due to steric hindrance at the pertinent site of deprotonation. In contrast, an alternative workup involving isolation of the crude triazene and its treatment with the much stronger base DBU (1.2 equiv) in CH$_2$Cl$_2$ furnished 5b within a few minutes and in 85% yield; NEt$_3$ was ineffectual in this instance. Similarly, azido lactam 2c (with DBU workup) gave the diazo-compound 5c in 95% yield.

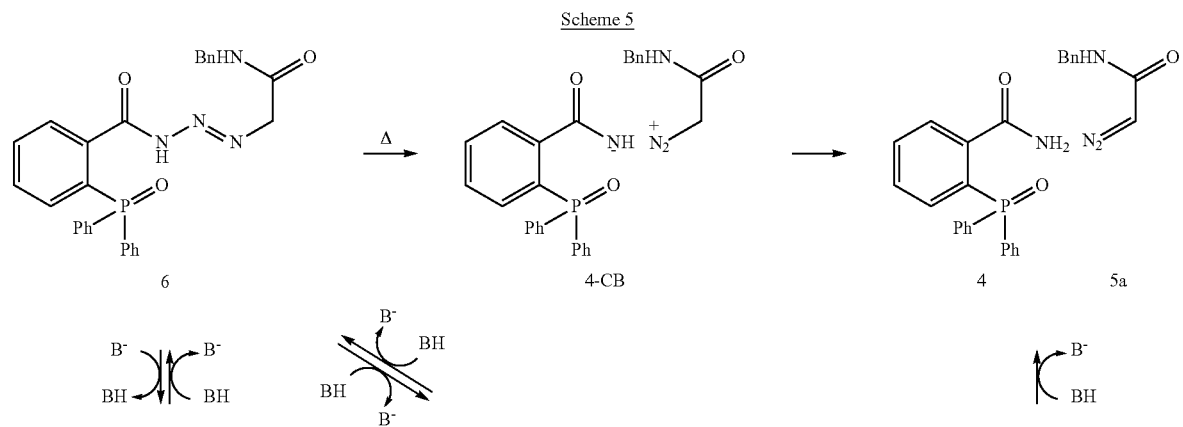

Scheme 5

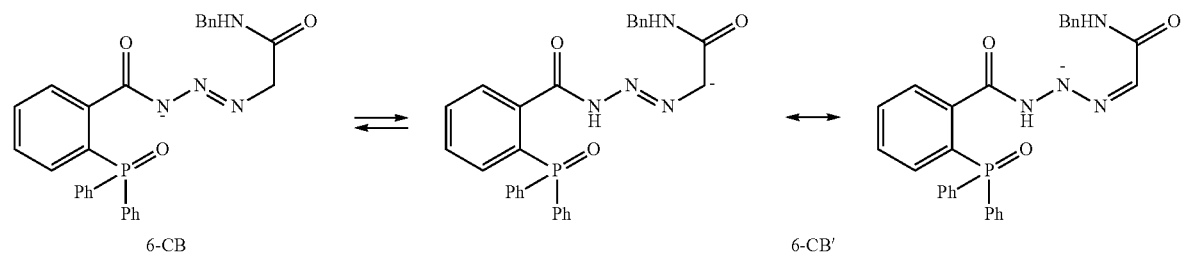

Scheme 6

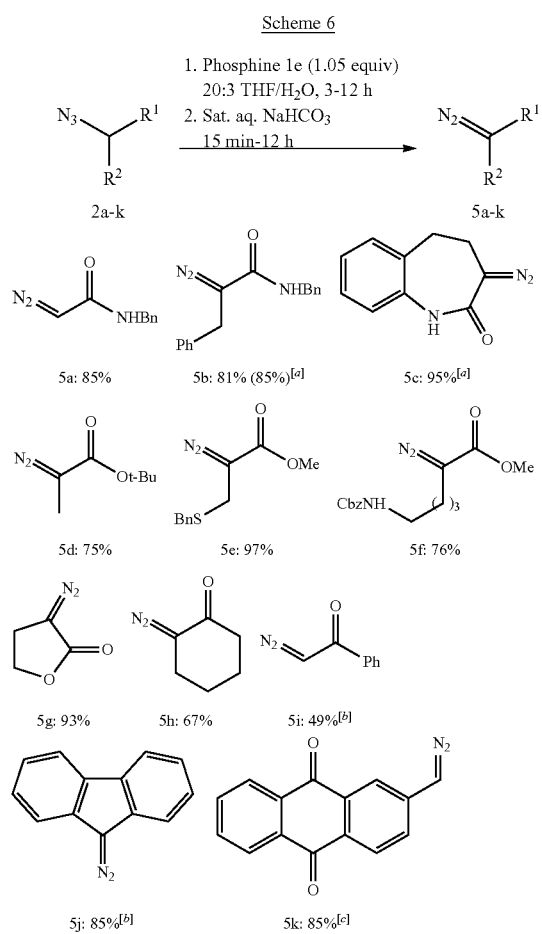

To probe the scope of the reaction even further, we investigated the synthesis of semi-stabilized diazo-compounds. Treatment of 9-azido-fluorene 2j with phosphine 1e under anhydrous conditions at low temperature (toluene, 0° C.), followed by loading the red solution directly on basic alumina (Grade 5) and eluting with 10% $CH_2Cl_2$/hexanes, 9-diazo-fluorene 5j was isolated in 85% yield and excellent purity (96%). Apparently, thermal fragmentation of the putative triazenophosphonium salt, which more than likely exists in its neutral $\lambda^5$-phosphorane form[16] is suppressed sufficiently for this substrate under the reaction conditions. The low temperature and low polarity of the solvent probably contribute to that greater stability. Under the standard conditions (THF/$H_2O$), incomplete conversion of the azide 2j and contamination of the diazo-compound 5j with substantial amounts of other products, probably arising from alternative triazene decomposition and dimerization of the diazo-compound, were apparent. Finally, a vinylogous diazo-carbonyl compound 5k (96% purity) was prepared in good yield from anthraquinone-based azide 2k using the standard conditions.

Benzyl azide, whose pertinent hydrogens are relatively non-acidic, was converted in good yield to acyl triazene 10 and, unsurprisingly, failed to undergo smooth conversion to the diazo-compound under the standard conditions (Scheme 7). Yet, when a solution of 10 in toluene was heated to 80° C. in the presence of phenylalanine carboxylic acid derivative 11, the benzyl ester 12 was isolated in 50% yield. Presumably, under the latter conditions the acyl triazene undergoes protic acid-induced fragmentation to the benzyl diazonium salt and primary amide followed by rapid alkylation of carboxylate. [19]

These results demonstrate that we have developed a mild method for the conversion of azides to their diazo-compound derivatives using phosphine reagents which are exemplified by reagent 1e. The reaction observed can be characterized as a "deimidogenation" reaction which is highly selective in most chemical environments and thus allows for the synthesis of diazo-compounds in the presence of delicate functionality, which is a challenge given current methodology. The methods of this invention are particularly useful in processes for preparing water-soluble phosphine reagents for applications in chemical biology,[21] for example, in which azide moieties on biomolecules[22] can be converted to diazonium groups which in turn can be employed in a variety of application, for example for the generation of the corresponding carbenes.

Scheme 7

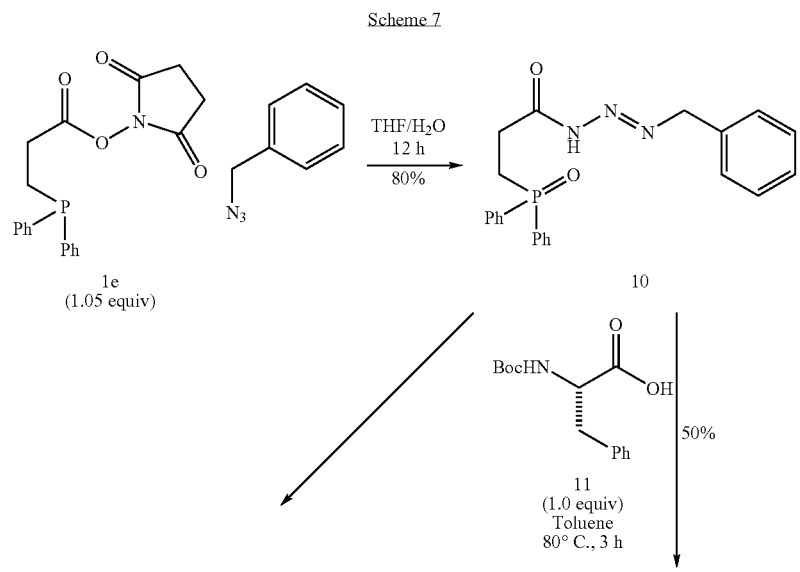

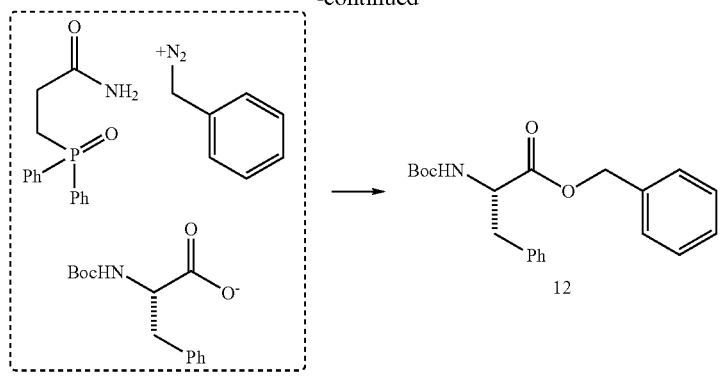
-continued

THE EXAMPLES

Example 1

General Methods

Reagent chemicals were obtained from commercial suppliers, and reagent grade solvents were used without further purification. Anhydrous $CH_2Cl_2$ was obtained from a CYCLE-TAINER® solvent delivery system (Baker). Anhydrous Toluene and $CH_3CN$ were obtained from Sigma-Aldrich. Procedures were performed at room temperature (~23° C.) unless indicated otherwise. Reactions were monitored by thin-layer chromatography using Whatman® aluminum-backed silica gel TLC plates with visualization by UV light. Compounds were purified by flash chromatography on silica gel, which had a mesh of 230-400 (ASTM) and a pore size of 60 Å or on basic aluminum oxide (Brockmann Grade V), which had an approximate mesh of 150 and a pore size of 58 Å. The removal of solvents and other volatile materials "under reduced pressure" refers to the use of a rotary evaporator at water-aspirator pressure (<20 torr) and a water bath of <40° C.

Instrumentation

NMR spectra were acquired at ambient temperature with a Bruker DMX-400 Avance spectrometer ($^1H$, 400.1 MHz; $^{13}C$, 100.6 MHz; $^{31}P$, 162.0 MHz at the National Magnetic Resonance Facility at Madison (NMRFAM). Carbon-13 and Phosphorus-31 spectra were proton-decoupled. $^1H$ NMR spectra were referenced to TMS or to the residual solvent peak. $^{13}C$ NMR spectra were referenced to the residual solvent peak. $^{31}P$ NMR spectra were referenced to an external source of 85% $H_3PO_4$. In certain Carbon-13 spectra the phrase "observed signals" is used when there is coincidental overlap of signals or the non-appearance of a quaternary carbon. Mass spectrometry was performed with a Micromass LCT (electrospray ionization, ESI) in the Mass Spectrometry Facility in the Department of Chemistry at the University of Wisconsin-Madison. X-Ray data were acquired at the Molecular Structure Laboratory in the Department of Chemistry at the University of Wisconsin-Madison using a Bruker-AXS SMART APEX2 with Cu $K_\alpha$ ($\lambda$=1.54178 Å) radiation at 100(2) K.

Example 2

Synthesis of Phosphines

Ethyl 2-(diphenylphosphanyl)benzoate (1a)

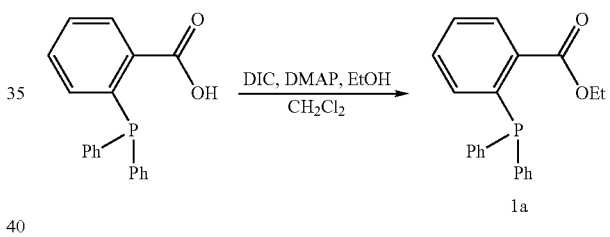

2-(Diphenylphosphanyl)benzoic acid (0.50 g, 1.63 mmol) and 4-dimethylaminopyridine (DMAP, 20 mg, 0.163 mmol) were dissolved in $CH_2Cl_2$ (10 mL). Ethanol (0.29 mL, 4.89 mmol) was added, and the solution was placed under Ar(g) and cooled to 0° C. N,N'-Diisopropylcarbodiimide (DIC, 0.25 mL, 1.63 mmol) was added dropwise, and the resulting solution was allowed to warm to room temperature and stirred overnight. The solution was then filtered, and the filtrate was concentrated under reduced pressure. The resulting residue was purified by silica gel column chromatography, eluting with 10% EtOAc(ethylacetate)/hexanes, to give phosphine 1a as a pale yellow solid (0.44 g, 1.32 mmol, 81% yield). 2-(Diphenylphosphanyl)benzoic acid was purchased from Sigma-Aldrich (St. Louis, Mo.).

Data for 1a: $^1H$ NMR (400 MHz, $CDCl_3$) δ=8.07 (m, 1H, Ar.), 7.44-7.25 (m, 12H, Ar.), 6.93 (m, 1H, Ar.), 4.22 (q, 2H, J=7.1 Hz, $OCH_2CH_3$), 1.21 (t, 3H, J=7.1 Hz, $OCH_2CH_3$). $^{13}C$ NMR (100 MHz, $CDCl_3$, $^{31}P$-coupled; $^1H$-decoupled, observed signals) δ=166.9, 140.8, 140.0, 138.1, 137.9, 134.8, 134.6, 134.3, 134.0, 133.8, 131.8, 130.6, 128.6, 128.5, 128.4, 128.2, 61.2, 14.0. $^{31}$P NMR (162 MHz, CDCl$_3$) δ=−4.0. HRMS (ESI$^+$) m/z calculated for (C$_{21}$H$_{20}$O$_2$P)$^+$ 335.1196, measured 335.1208.

[2-(Diphenylphosphanyl)phenyl](ethylsulfanyl)methanone (1b)

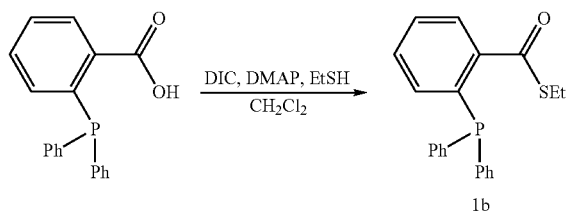

2-(Diphenylphosphanyl)benzoic acid (0.50 g, 1.63 mmol) and DMAP (20 mg, 0.163 mmol) were dissolved in CH$_2$Cl$_2$ (10 mL). Ethanethiol (EtSH, 0.35 mL, 4.89 mmol) was added, and the solution was placed under Ar(g) and cooled to 0° C. DIC (0.25 mL, 1.63 mmol) was added dropwise, and the resulting solution was allowed to warm to room temperature and stirred overnight. The solution was then filtered, and the filtrate was concentrated under reduced pressure. The resulting residue was purified by silica gel column chromatography, eluting with 10% EtOAc/hexanes, to give phosphine 1b as a pale yellow solid (0.43 g, 1.22 mmol, 75% yield).

Data for 1b: $^1$H NMR (400 MHz, CDCl$_3$) δ=8.02 (m, 1H, Ar.), 7.45-7.24 (m, 12H, Ar.), 6.99 (m, 1H, Ar.), 2.98 (q, 2H, J=7.4 Hz, SCH$_2$CH$_3$), 1.22 (t, 3H, J =7.4 Hz, SCH$_2$CH$_3$). $^{13}$C NMR (100 MHz, CDCl$_3$, $^{31}$P-coupled; $^1$H-decoupled, observed signals) δ=192.7, 141.9, 141.7, 138.0, 137.8, 137.7, 134.6, 134.0, 133.8, 131.7, 128.9, 128.6, 128.4, 128.4, 128.3, 24.0, 14.6. $^{31}$P NMR (162 MHz, CDCl$_3$) δ=−5.8. HRMS (ESI$^+$) m/z calculated for (C$_{21}$H$_{20}$OPS)$^+$351.0968, measured 351.0953.

2,5-Dioxopyrrolidin-1-yl-2-(diphenylphosphanyl)benzoate (1c)

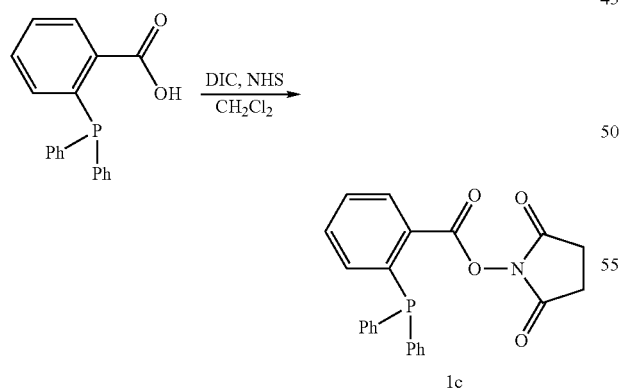

2-(Diphenylphosphanyl)benzoic acid (1.00 g, 3.26 mmol) was dissolved in CH$_2$Cl$_2$ (10 mL), and the solution was cooled to 0° C. N-Hydroxysuccinimide (NHS, 0.75 g, 6.53 mmol) and DIC (0.56 mL, 3.59 mmol) were added, and the mixture was allowed to warm to room temperature and stirred overnight under Ar(g). The resulting suspension was filtered, and the filtrate was concentrated under reduced pressure. The resulting residue was purified by silica gel flash chromatography, eluting with 30% EtOAc/hexanes, to give the ester as a pale yellow solid (1.28 g, 3.17 mmol, 97% yield).

Data for 1c: $^1$H NMR (400 MHz, CDCl$_3$) δ=8.34 (m, 1H, Ar), 7.55-7.22 (m, 12H, Ar), 7.02 (m, 1H, Ar), 2.83 (4H, s, CH$_2$CH$_2$). $^{13}$C NMR (100 MHz, CDCl$_3$, $^{31}$P-coupled; $^1$H-decoupled, observed signals) δ=169.0, 160.8, 143.2, 142.9, 136.8, 136.6, 134.8, 133.9, 133.8, 133.7, 131.6, 128.8, 128.5, 128.5, 25.5. $^{31}$P NMR (162 MHz, CDCl$_3$) δ=−4.0. HRMS (ESI$^+$) m/z calculated for (C$_{23}$H$_{19}$NO$_4$P)$^+$404.1052, measured 404.1063.

3-(Diphenylphosphanyl)propanoic acid (1d)

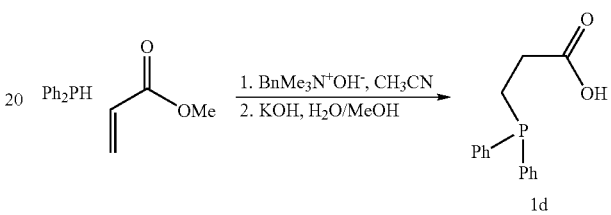

Diphenylphosphine (2.00 mL, 11.5 mmol) was dissolved in degassed CH$_3$CN (20 mL). Methyl acrylate (3.80 mL, 42.5 mmol) and a few drops of benzyltrimethylammonium hydroxide (40 wt. % in MeOH) were added, and the resulting solution was stirred under Ar(g). The reaction was monitored by TLC and after the introduction of additional drops of base (after 2 h) the reaction was found to be complete after 4 h. The solution was then concentrated under reduced pressure; the resulting oil was dissolved in CH$_2$Cl$_2$ (100 mL) and concentrated again. The resulting oil was then dissolved in MeOH (10 mL) and an aqueous solution of KOH (4.00 g, 71.4 mmol in 10 mL of H$_2$O) was added. The mixture was stirred under Ar(g). After 1 h, the reaction was found to be complete, and the solution was diluted with H$_2$O (200 mL) and acidified to pH 2 with 2M HCl. The suspension was then extracted with CH$_2$Cl$_2$ (2×150 mL), and the organic layers were combined, dried over Na$_2$SO$_4$(s) and concentrated under reduced pressure. The solid residue was purified by silica gel flash chromatography, eluting with 2% MeOH/CH$_2$Cl$_2$, to give the acid 1d as a white solid (2.74 g, 10.6 mmol, 92% yield).

Data for 1d: $^1$H NMR (400 MHz, CDCl$_3$) δ=7.46-7.32 (10H, m, Ar), 2.44 (m, 2H, CH$_2$), 2.35 (m, 2H, CH$_2$). $^{13}$C NMR (100 MHz, CDCl$_3$, $^{31}$P-coupled; $^1$H-decoupled, observed signals) δ=179.1, 179.0, 137.5, 137.4, 132.8, 132.6, 128.9, 128.6, 128.5, 30.5, 30.2, 22.7, 22.6. $^{31}$P NMR (162 MHz, CDCl$_3$) δ=−15.5. HRMS (ESI$^+$) m/z calculated for (C$_{15}$H$_{16}$O$_2$P)$^+$ 259.0888, measured 259.0895.

2,5-Dioxopyrrolidin-1-yl 3-(diphenylphosphanyl)propanoate (1e)

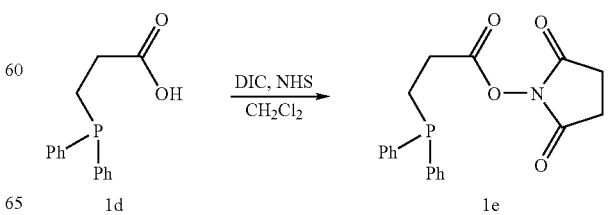

3-(Diphenylphosphanyl)propanoic acid 1d (1.20 g, 4.65 mmol) was dissolved in $CH_2Cl_2$ (10 mL), and the solution was cooled to 0° C. NHS (1.05 g, 9.30 mmol) and DIC (0.86 mL, 5.58 mmol) were added, and the mixture was allowed to warm to room temperature and stirred overnight under Ar(g). The resulting suspension was filtered, and the filtrate was concentrated under reduced pressure. The resulting residue was purified by silica gel flash chromatography, eluting with 30% EtOAc-hexanes, to give the ester 1e as a white solid (1.64 g, 4.62 mmol, 99% yield).

Data for 1e: $^1H$ NMR (400 MHz, $CDCl_3$) δ=7.47-7.32 (m, 10H, Ar), 2.82 (s, 4H, succinmyl), 2.67 (m, 2H, $CH_2$), 2.43 (m, 2H, $CH_2$). $^{13}C$ NMR (100 MHz, $CDCl_3$, $^{31}P$-coupled; $^1H$-decoupled, observed signals) δ=169.0, 168.5, 168.3, 137.0, 136.8, 132.8, 132.6, 129.1, 128.7, 128.7, 27.8, 27.6, 25.6, 22.7, 22.6. $^{31}P$ NMR (162 MHz, $CDCl_3$) δ=−15.3. HRMS (ESI$^+$) m/z calculated for $(C_{19}H_{19}NO_4P)^+$ 356.1052, measured 356.1060.

Example 3

Synthesis of Azides

2-Azido-N-benzyl-3-phenylpropanamide (2b)

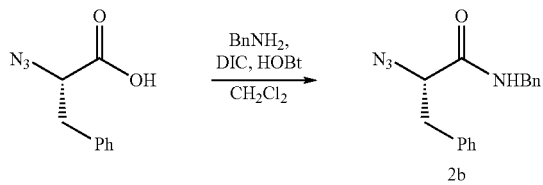

2-Azido-3-phenylpropanoic acid (J. T. Lundquist IV, J. C. Pelletier, Org. Lett. 2001, 3, 781-783) (112 mg, 0.588 mmol) and HOBt (108 mg, 0.705 mmol) were suspended in $CH_2Cl_2$ (2 mL), and the mixture was cooled to 0° C. under Ar(g). DIC (107 μL, 0.705 mmol) was added, and the resulting mixture was stirred for 30 min. Benzyl amine (122 μL, 1.06 mmol) was then added, and the mixture was allowed to warm to room temperature and then stirred overnight under Ar(g). The mixture was filtered, and the solvent was removed under reduced pressure. The residue was purified by silica gel flash chromatography, eluting with 15% EtOAc/hexanes, to give the required amide 2b as a white solid (117 mg, 0.418 mmol, 71% yield).

Data for 2b: $^1H$ NMR (400 MHz, $CDCl_3$) δ=7.35-7.21 (m, 7H, Ar.), 7.16-7.10 (m, 3H, Ar.), 6.52 (br. s, 1H, NH), 4.43 (dd, 1H, J=14.7, 6.1 Hz, NHCH$_2$Ph), 4.37 (dd, 1H, J=14.7, 5.4 Hz, NHCH$_2$Ph), 4.24 (dd, 1H, J=7.7, 4.0 Hz, CHCH$_2$Ph), 3.36 (dd, 1H, J=14.0, 4.0 Hz, CHCH$_2$Ph), 3.08 (dd, 1H, J=14.0, 7.7 Hz, CHCH$_2$Ph). $^{13}C$ NMR (100 MHz, $CDCl_3$, observed signals) δ=168.3, 137.3, 136.0, 128.7, 128.7, 127.7, 127.6, 127.2, 65.5, 43.6, 38.5. HRMS (ESI$^+$) m/z calculated for $(C_{16}H_{16}N_4O)^+$ 280.1319, measured 280.1315.

3-Azido-2,3,4,5-tetrahydro-1H-1-benzazepin-2-one (2c)

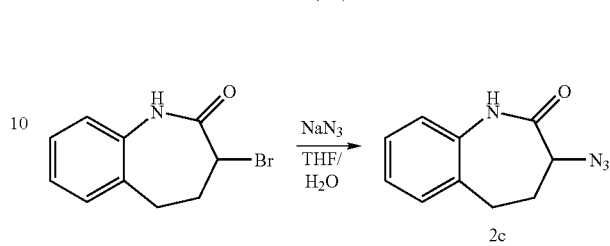

3-Bromo-2,3,4,5-tetrahydro-1H-1-benzazepin-2-one (Purchased from AK Scientific, Inc.) (0.50 g, 2.08 mmol) was dissolved in THF (5 mL). A solution of $NaN_3$ (1.36 g, 20.82 mmol) in $H_2O$ (2 mL) was added, and the resulting mixture was stirred vigorously for 3 days. THF was removed under reduced pressure, and the resulting aqueous slurry was extracted with $CH_2Cl_2$ (2×20 mL). The organic layers were combined, dried over $Na_2SO_4$(s), filtered, and concentrated under reduced pressure. The resulting off-white solid (0.40 g, 1.98 mmol, 95% yield) was found to be pure by NMR analysis and was used without further purification.

Data for 2c: $^1H$ NMR (400 MHz, $CDCl_3$) δ=7.77 (br. s, 1H, NH), 7.31-7.15 (m, 3H, Ar), 7.03 (d, 1H, J=7.8 Hz, Ar.), 3.88 (dd, 1H, J=11.0, 8.3 Hz, NHC(O)CHN$_3$), 3.00 (m, 1H, $CH_2$), 2.74 (m, 1H, $CH_2$), 2.53 (m, 1H, $CH_2$), 2.32 (m, 1H, $CH_2$). $^1H$ NMR (400 MHz, DMSO-d$_6$) δ=10.05 (br. s, 1H, NH), 7.30-7.22 (m, 2H, Ar), 7.12 (t, 1H, J=7.4 Hz, Ar), 7.00 (d, 1H, J=7.8 Hz, Ar.), 3.88 (dd, 1H, J=10.7, 8.5 Hz, NHC(O)CHN$_3$), 2.82-2.65 (m, 2H, $CH_2$), 2.40 (m, 1H, $CH_2$), 2.11 (m, 1H, $CH_2$). $^{13}C$ NMR (100 MHz, DMSO-d$_6$) δ=170.3, 137.5, 133.4, 130.0, 127.9, 125.7, 124.5, 122.5, 59.1, 34.8, 28.2. {Lit.: $^1H$ NMR (390 MHz, DMSO-d$_6$) δ=10.15 (br. s, 1H, NH), 7.22 (m, 4H, Ar), 3.88 (dd, 1H, NHC(O)CHN$_3$), 2.50 (m, 4H, $CH_2$) J. W. H. Watthey, J. L. Stanton, M. Desai, J. E. Babiarz, B. M. Finn, J. Med. Chem. 1985, 28, 1511-1516.}

Methyl 2-azido-3-(benzylsulfanyl)propanoate (2e)

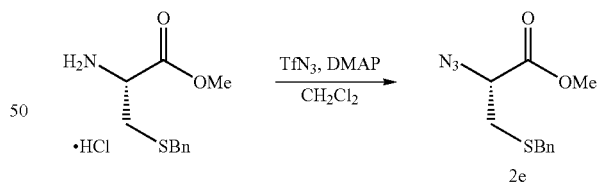

Following a method described by Aubé and coworkers [S. K. Ramanathan, J. Keeler, H.-L. Lee, D. S. Reddy, G. Lushington, J. Aubé, Org. Lett. 2005, 7, 1059-1062], a solution of $NaN_3$ (0.88 g, 13.7 mmol) in $H_2O$ (2.5 mL) was cooled to 0° C. and $CH_2Cl_2$ (4 mL) was added. Whilst the mixture was stirring vigorously, $Tf_2O$ ($CF_3SO_2OSO_2CF_3$, 0.47 mL, 2.26 mmol) was added dropwise. The resulting solution was stirred for an additional 2 h. The mixture was then placed in a separating funnel, and the organic layer was removed. The aqueous phase was extracted further with $CH_2Cl_2$ (2×3 mL). The organic layers were combined, washed with saturated $Na_2CO_3$, dried over $Na_2SO_4$(s), and filtered. The resulting solution of $TfN_3$ was added dropwise to a solution of methyl 2-amino-3-(benzylsulfanyl)propanoate hydrochloride salt (0.37 g, 1.40 mmol) and DMAP (0.75 g, 6.16 mmol) in CH$_2$Cl$_2$ (5 mL). The resulting solution was stirred overnight under Ar(g). The mixture was concentrated under reduced pressure and purified by silica gel flash chromatography, eluting with CH$_2$Cl$_2$, to give azide 2e as an oil (0.26 g, 1.05 mmol, 75% yield).

Data for 2e: $^1$H NMR (400 MHz, CDCl$_3$) δ=7.37-7.24 (m, 5H, Ar.), 3.98 (dd, 1H, J=7.5, 5.7 Hz, N$_3$CH), 3.82-3.79 (m, 5H, OCH$_3$ and CH$_2$Ph), 2.86 (dd, 1H, J=14.1, 5.7 Hz, CH$_2$SBn), 2.73 (dd, 1H, J=14.1, 7.5 Hz, CH$_2$SBn). $^{13}$C NMR (100 MHz, CDCl$_3$) δ=169.4, 137.5, 129.0, 128.6, 127.3, 62.3, 52.3, 36.8, 32.3. HRMS (ESI$^+$) m/z calculated for (C$_{11}$H$_{13}$N$_3$O$_2$SNa)$^+$ 274.0621, measured 274.0610.

Methyl 2-azido-6-{[(benzyloxy)carbonyl]amino}hexanoate (2f)

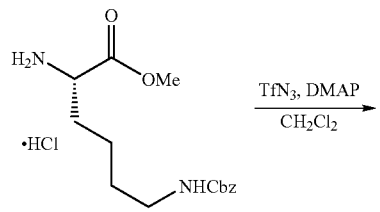

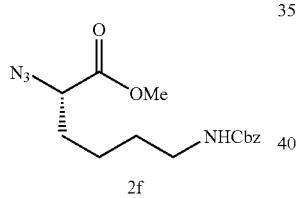

Following the method described by Aubé and coworkers, supra, a solution of NaN$_3$ (0.88 g, 13.7 mmol) in H$_2$O (2.5 mL) was cooled to 0° C. and CH$_2$Cl$_2$ (4 mL) was added. Whilst the mixture was stirring vigorously, Tf$_2$O (0.47 mL, 2.26 mmol) was added dropwise. The resulting solution was stirred for an additional 2 h. The mixture was then placed in a separating funnel, and the organic layer was removed. The aqueous phase was extracted further with CH$_2$Cl$_2$ (2×3 mL). The organic layers were combined, washed with saturated Na$_2$CO$_3$, dried over Na$_2$SO$_4$(s), and filtered. The resulting solution of TfN$_3$ was added dropwise to solution of methyl 2-amino-6-{[(benzyloxy)carbonyl]amino}hexanoate hydrochloride salt (0.46 g, 1.40 mmol) and DMAP (0.75 g, 6.16 mmol) in CH$_2$Cl$_2$ (5 mL). The resulting solution was stirred overnight under Ar(g). The mixture was concentrated under reduced pressure and purified by silica gel flash chromatography, eluting with 20% EtOAc/hexanes, to give azide 2f as an oil (0.43 g, 1.34 mmol, 96% yield).

Data for 2f: $^1$H NMR (400 MHz, CDCl$_3$) δ=7.38-7.28 (m, 5H, Ar.), 5.10 (s, 2H, OCH$_2$Ph), 4.80 (br. s, 1H, NH), 3.84 (m, 1H, N$_3$CH), 3.79 (s, 3H, OCH$_3$), 3.21 (m, 2H, CH$_2$NHCbz), 1.91-1.45 (m, 6H, CH$_2$CH$_2$CH$_2$NHCbz). $^{13}$C NMR (100 MHz, CDCl$_3$) δ=170.9, 156.4, 136.5, 128.5, 128.1, 128.1, 66.7, 61.8, 52.6, 40.7, 30.9, 29.4, 22.9. HRMS (ESI$^+$) m/z calculated for (C$_{15}$H$_{20}$N$_4$O$_4$Na)$^+$343.1377, measured 343.1366.

3-Azidooxolan-2-one (2g)

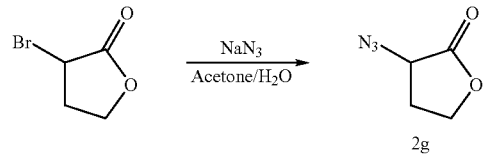 [SMILES: O=C1OCCC1Br ; "NaN3" ; [N-]=[N+]=NC1CCOC1=O]

3-Bromooxolan-2-one (0.50 g, 3.03 mmol) was dissolved in acetone (5 mL). To this was added a solution of NaN$_3$ (0.99 g, 15.2 mmol) in H$_2$O (2 mL). The resulting solution was stirred overnight. Acetone was removed by concentration under reduced pressure. The resulting aqueous mixture was extracted with CH$_2$Cl$_2$ (2×15 mL), and the organic layers were combined, dried over Na$_2$SO$_4$(s), filtered, and concentrated under reduced pressure. The resulting oil (0.29 g, 2.27 mmol, 75% yield) was found to be pure by NMR analysis and was used without further purification.

Data for 2g: $^1$H NMR (400 MHz, CDCl$_3$) δ=4.43 (ddd, 1H, J=9.0, 9.0, 3.5 Hz, OCH$_2$CH$_2$), 4.33-4.24 (m, 2H, OCH$_2$CH$_2$CHN$_3$), 2.56 (m, 1H, OCH$_2$CH$_2$), 2.19 (dddd, 1H, J=9.0, 9.0, 9.0, 13.3, OCH$_2$CH$_2$). $^{13}$C NMR (100 MHz, CDCl$_3$) δ=173.3, 65.8, 56.5, 28.9. HRMS (ESI$^+$) m/z calculated for (C$_4$H$_5$N$_3$O$_2$)$^+$127.0377, measured 127.0376.

2-Azidocyclohexan-1-one (2h)

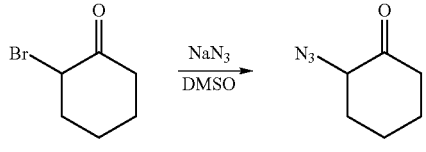

2-Bromocyclohexan-1-one (K. Tanemura, T. Suzuki, Y. Nishida, K. Satsumabayashi, T. Horaguchi, Chem. Commun. 2004, 470-471) (0.55 g, 3.11 mmol) was dissolved in DMSO (3 mL). Sodium azide (1.00 g, 15.5 mmol) was added, and the resulting mixture was stirred for 2 h. The solution was then diluted with water (50 mL) and extracted with diethyl ether (2×20 mL). The organic layers were combined, washed with water (2×20 mL), dried over Na$_2$SO$_4$(s), filtered, and concentrated under reduced pressure. The resulting oil was found to be pure by NMR analysis and was used without further purification (0.40 g, 2.87 mmol, 92% yield).

Data for 2 h: $^1$H NMR (400 MHz, CDCl$_3$) δ=3.94 (dd, 1H, J=11.4, 6.6 Hz, CHN$_3$), 2.57 (br. d, 1H, J=14.0 Hz), 2.41-2.28 (m, 2H), 2.14-1.93 (m, 2H), 1.80-1.61 (m, 3H). $^{13}$C NMR (CDCl$_3$, 400 MHz) δ=205.5, 66.5, 40.8, 33.6, 27.0, 23.8. {Lit: $^1$H NMR (400 MHz, CDCl$_3$) δ=3.93 (dd, 1H, J=11.4, 6.6 Hz, CHN$_3$), 2.56-1.66 (m, 8H). $^{13}$C NMR (CDCl$_3$, 400

MHz) δ=205.6, 66.5, 40.8, 33.6, 27.1, 23.8; [T. Patonay, R. V. Hoffman, *J. Org. Chem.* 1994, 59, 2902-2905].

2-Azido-1-phenylethan-1-one (2i)

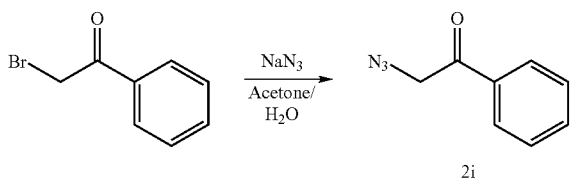 [SMILES: O=C(CBr)c1ccccc1 ; "NaN3" ; [N-]=[N+]=NCC(=O)c1ccccc1]

2-Bromo-1-phenylethan-1-one (1.00 g, 5.02 mmol) was dissolved in acetone (7 mL). To this was added a solution of NaN$_3$ (1.63 g, 25.1 mmol) in H$_2$O (3 mL). The resulting solution was stirred overnight. Acetone was removed under reduced pressure, and the resulting aqueous mixture was extracted with CH$_2$Cl$_2$ (2×15 mL). The organic layers were combined, dried over Na$_2$SO$_4$(s), filtered, and concentrated under reduced pressure. The resulting yellow oil (0.60 g, 3.72 mmol, 74% yield) was found to be pure by NMR analysis and was used without further purification.

Data for 2i: $^1$H NMR (400 MHz, CDCl$_3$) δ=7.93 (d, 2H, J=7.8 Hz, Ar.), 7.65 (t, 1H, J=7.2 Hz, Ar.), 7.52 (app. t, 2H, J=7.5 Hz), 4.59 (s, 2H, CH$_2$N$_3$). $^{13}$C NMR (CDCl$_3$, 400 MHz) δ=193.2, 134.3, 134.1, 129.0, 127.9, 54.9.: $^1$H NMR (400 MHz, CDCl$_3$) δ=7.99 (dd, 2H), 7.63 (m, 1H), 7.50 (dd, 2H), 4.57 (s, 2H). $^{13}$C NMR (CDCl$_3$, 400 MHz) δ=193.3, 134.3, 134.1, 129.0, 127.9, 54.9, (T. Patonay, R. V. Hoffman, *J. Org. Chem.* 1994, 59, 2902-2905.)

9-Azido-9H-fluorene (2j)

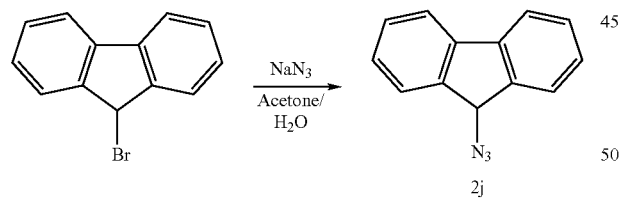

9-Bromo-9H-fluorene (1.00 g, 4.08 mmol) was dissolved in acetone (7 mL). To this was added a solution of NaN$_3$ (1.33 g, 20.4 mmol) in H$_2$O (3 mL). The resulting solution was stirred overnight. Acetone was removed by concentration under reduced pressure. The resulting aqueous mixture was extracted with CH$_2$Cl$_2$ (2×15 mL), and the organic layers were combined, dried over Na$_2$SO$_4$(s), filtered, and concentrated under reduced pressure. The resulting solid residue was purified by silica gel flash chromatography, eluting with hexanes, to give azide 2j as a white solid (0.74 g, 3.57 mmol, 87% yield).

Data for 2j: $^1$H NMR (400 MHz, CDCl$_3$) δ=7.74 (d, 2H, J=7.4 Hz, Ar.), 7.66 (d, 2H, J=7.4 Hz, Ar.), 7.47 (t, 2H, J=7.4 Hz, Ar.), 7.39 (t, 2H, J=7.4 Hz, Ar.), 5.23 (s, 1H, CHN$_3$). $^{13}$C NMR (100 MHz, CDCl$_3$) δ=141.6, 140.7, 129.4, 127.9, 125.2, 120.3, 64.3.

2-(Azidomethyl)-9,10-dihydroanthracene-9,10-dione (2k)

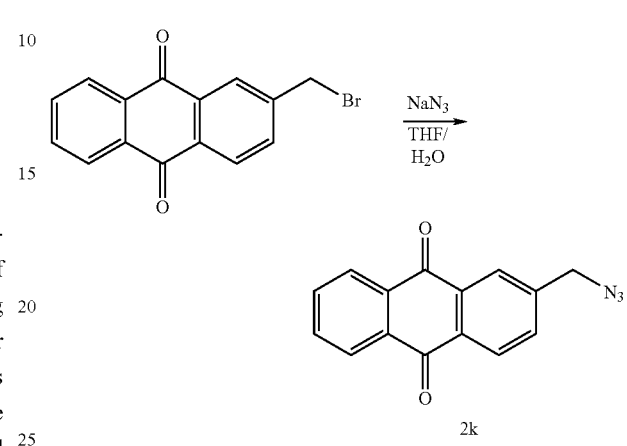

2-(Bromomethyl)-9,10-dihydroanthracene-9,10-dione (0.54 g, 1.66 mmol) was dissolved in THF (5 mL). To this was added a solution of NaN$_3$ (0.54 g, 8.30 mmol) in H$_2$O (2 mL), and the resulting mixture was stirred overnight. THF was removed by evaporation under reduced pressure, and the aqueous mixture was extracted with CH$_2$Cl$_2$ (2×15 mL). The organic layers were combined, dried over Na$_2$SO$_4$(s), filtered, and concentrated under reduced pressure to give a pale yellow solid (0.42 g, 1.59 mmol, 96% yield). The solid was found to be pure by NMR analysis and was used without further purification.

Data for 2k: $^1$H NMR (400 MHz, CDCl$_3$) δ=8.39-8.31 (m, 3H, Ar), 8.27 (s, 1H, Ar), 7.86-7.82 (m, 2H, Ar), 7.79 (d, 1H, J=7.9 Hz, Ar), 4.59 (s, 2H, CH-$_2$N3). $^{13}$C NMR (CDCl$_3$, 400 MHz, observed signals) δ=182.8, 182.6, 142.1, 134.3, 134.2, 133.8, 133.4, 133.2, 133.1, 128.0, 127.3, 126.4, 50.1.

N-(4-Azidophenyl)-4-methylbenzene-1-sulfonamide (7)

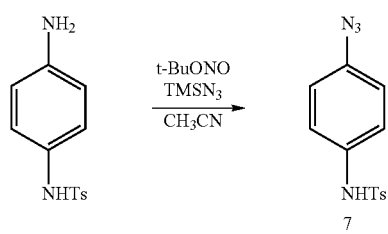

Following the procedure of Moses and coworkers (K. Barral, A. D. Moorhouse, J. E. Moses, *Org. Lett.* 2007, 9, 1809-1811). N-(4-aminophenyl)-4-methylbenzene-1-sulfonamide (1.00 g, 3.81 mmol) was dissolved in anhydrous CH$_3$CN (6 mL), and the resulting solution was placed under Ar(g) and cooled to 0° C. To this was added t-BuONO (0.68 mL, 5.71 mmol) followed by TMSN$_3$ (0.60 mL, 4.57 mmol) dropwise. The resulting solution was allowed to warm to room temperature and stirred for 2 h. The resulting mixture was concentrated under reduced pressure, and the residue was purified by silica gel column chromatography, eluting with 10% EtOAc/hexanes, to give aryl azide 7 (1.02 g, 3.54 mmol, 93% yield) as a white solid.

Data for 7: $^1$H NMR (400 MHz, CDCl$_3$) δ=7.68 (d, 2H, J=8.1 Hz, Ar.), 7.25 (d, 2H, J=8.1 Hz, Ar), 7.10 (d, 2H, J=8.2 Hz, Ar), 6.90 (d, 2H, J=8.2 Hz, Ar), 2.40 (s, 3H, CH$_3$). $^{13}$C NMR (100 MHz, CDCl$_3$) δ=144.1, 137.4, 135.7, 133.3, 129.7, 127.3, 123.7, 119.8, 21.5. HRMS (ESI$^+$) m/z calculated for $(C_{13}H_{12}N_4O_2S-N_2)^+$ 260.0614, measured 260.0623.

Example 4

Synthesis of Diazo-Compounds

N-Benzyl-2-diazoacetamide (5a)

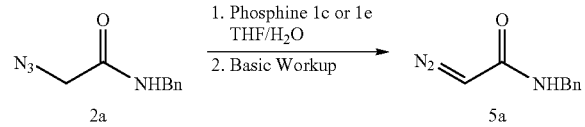

Method A: Using phosphine 1c; sat. aq. NaHCO$_3$ workup 2-Azido-N-benzylacetamide (B. L. Nilsson, L. L. Kiessling, R. T. Raines, *Org. Lett.* 2000, 2, 1939-1941) 2a (51 mg, 0.268 mmol) was dissolved in THF/H$_2$O (2 mL/300 μL). To this solution was added phosphine 1c (114 mg, 0.282 mmol), and the resulting solution was stirred overnight under Ar(g). Sat. aq. NaHCO$_3$ (2 mL) was then added, and the mixture was stirred vigorously for 4 h. The mixture was then diluted with sat. aq. NaCl (15 mL) and extracted with CH$_2$Cl$_2$ (2×15 mL). The organic layers were combined, dried over Na$_2$SO$_4$(s), filtered, and evaporated under reduced pressure. The residue was purified by silica gel flash chromatography, eluting with 30% EtOAc/hexanes, to give the diazo-compound 5a as a yellow solid (40 mg, 0.228 mmol, 85% yield).

Method B: Using phosphine 1c; NEt$_3$ (triethylamine) workup 2-Azido-N-benzylacetamide 2a (72 mg, 0.379 mmol) was dissolved in THF/H$_2$O (2 mL/300 μL). To this solution was added phosphine 1c (160 mg, 0.398 mmol), and the resulting solution was stirred overnight under Ar(g). NEt$_3$ (105 μL, 0.758 mmol) was then added, and the mixture was stirred for 1 h. The mixture was then diluted with sat. aq. NaCl (15 mL) and extracted with CH$_2$Cl$_2$ (2×15 mL). The organic layers were combined, dried over Na$_2$SO$_4$(s), filtered, and evaporated under reduced pressure. The residue was purified by silica gel flash chromatography, eluting with 30% EtOAc/hexanes, to give the diazo-compound 5a as a yellow solid (60 mg, 0.341 mmol, 90% yield).

Method C: Using phosphine 1e; sat. aq. NaHCO$_3$ workup 2-Azido-N-benzylacetamide 2a (57 mg, 0.300 mmol) was dissolved in THF/H$_2$O (2 mL/300 μL). To this solution was added phosphine 1e (112 mg, 0.315 mmol), and the resulting solution was stirred for 4 h under Ar(g). Sat. aq. NaHCO$_3$ (2 mL) was then added, and the mixture was stirred vigorously for 4 h. The mixture was then diluted with sat. aq. NaCl (15 mL) and extracted with CH$_2$Cl$_2$ (2×15 mL). The organic layers were combined, dried over Na$_2$SO(s), filtered, and evaporated under reduced pressure. The residue was purified by silica gel flash chromatography, eluting with 30% EtOAc/hexanes, to give the diazo-compound 5a as a yellow solid (45 mg, 0.255 mmol, 85% yield).

Data for 5a: $^1$H NMR (400 MHz, CDCl$_3$) δ=7.36-7.24 (m, 5H, Ar.), 5.73 (br. s, 1H, NH), 4.77 (1H, s, CHN$_2$), 4.43 (d, 2H, NHCH$_2$Ph). $^{13}$C NMR (100 MHz, CDCl$_3$) δ=165.6, 138.3, 128.7, 127.6, 127.5, 47.1, 43.9. HRMS (ESI$^+$) m/z calculated for $(C_9H_9N_3ONa)^+$ 198.0643, measured 198.0634.

N-Benzyl-2-diaza-3-phenylpropanamide (5b)

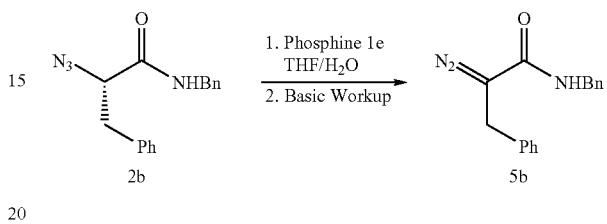

Method A (Sat. Aq. NaHCO$_3$ Workup):

2-Azido-N-benzyl-3-phenylpropanamide 2b (61 mg, 0.218 mmol) was dissolved in THF/H$_2$O (2 mL/300 μL). To this solution was added phosphine 1e (81 mg, 0.229 mmol), and the resulting solution was stirred for 5 h under Ar(g). Sat. aq. NaHCO$_3$ (2 mL) was then added, and the mixture was stirred vigorously overnight. The mixture was then diluted with sat. aq. NaCl (15 mL) and extracted with CH$_2$Cl$_2$ (2×15 mL). The organic layers were combined, dried over Na$_2$SO$_4$(s), filtered, and evaporated under reduced pressure. The residue was purified by silica gel flash chromatography, eluting with 20% EtOAc/hexanes, to give the diazo-compound 5b as a yellow oil (47 mg, 0.177 mmol, 81% yield).

Method B (DBU Workup):

2-Azido-N-benzyl-3-phenylpropanamide 2b (61 mg, 0.218 mmol) was dissolved in THF/H$_2$O (2 mL/300 μL). To this solution was added phosphine 1e (81 mg, 0.229 mmol), and the resulting solution was stirred for 5 h under Ar(g). The solution was then diluted with sat. aq. NaCl (10 mL), and the resulting mixture was extracted with CH$_2$Cl$_2$ (2×15 mL). The organic layers were combined, dried over Na$_2$SO$_4$(s), filtered, and evaporated under reduced pressure. The resulting residue was dissolved in CH$_2$Cl$_2$ (2 mL) and DBU (58 mL, 0.391 mmol) was added. The resulting solution was stirred for 20 min. The solution was placed directly onto a column of silica gel and eluted with 20% EtOAc/hexanes to give the diazo-compound 5b as a yellow oil (49 mg, 0.185 mmol, 85% yield).

Data for 5b: $^1$H NMR (400 MHz, CDCl$_3$) δ=7.37-7.24 (m, 9H, Ar.), 7.16 (d, 2H, J=7.0 Hz, Ar.), 5.35 (br. s., 1H, NH), 4.48 (d, 2H, J=5.5 Hz, NHCH$_2$Ph), 3.69 (s, 2H, CN$_2$CH$_2$Ph). $^{13}$C NMR (100 MHz, CDCl$_3$, observed signals) δ=165.9, 138.3, 136.6, 129.0, 128.6, 128.2, 127.6, 127.4, 57.3, 44.1, 29.8. HRMS (ESI+) m/z calculated for $(C_{16}H_{15}N_3O)^+$ 265.1210, measured 265.1223.

3-Diazynylidene-4,5-dihydro-1H-1-benzazepin-2-one 5c

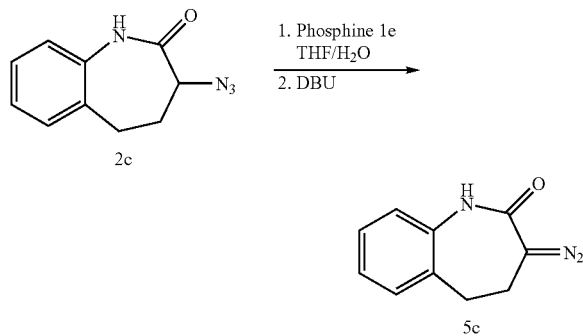

3-Azido-2,3,4,5-tetrahydro-1H-1-benzazepin-2-one 2c (66 mg, 0.326 mmol) was dissolved in THF/H$_2$O (2 mL/300 μL). To this was added phosphine 1e (122 mg, 0.343 mmol), and the resulting solution was stirred for 5 h under Ar(g). The solution was then diluted with sat. aq. NaCl (10 mL), and the resulting mixture was extracted with CH$_2$Cl$_2$ (2×15 mL). The organic layers were combined, dried over Na$_2$SO$_4$(s), filtered, and evaporated under reduced pressure. The resulting residue was dissolved in CH$_2$Cl$_2$ (2 mL) and DBU (58 mL, 0.391 mmol) was added. The resulting solution was allowed stirred for 20 min. The solution was placed directly onto a column of silica gel and eluted with 30% EtOAc/hexanes to give the diazo-compound 5c as a yellow solid (58 mg, 0.310 mmol, 95% yield).

Data for 5c: $^1$H NMR (400 MHz, CDCl$_3$) δ=7.68 (br. s, 1H, NH), 7.20 (app. t, 1H, J=7.5 Hz, Ar.), 7.11 (d, 1H, J=7.3 Hz, Ar.), 7.02 (app. t, 1H, J=7.3 Hz, Ar.), 6.89 (d, 1H, J=7.5 Hz, Ar.), 3.03 (m, 2H, CH$_2$), 2.87 (m, 2H, CH$_2$). $^{13}$C NMR (100 MHz, CDCl$_3$) δ=167.3, 136.8, 130.8, 130.0, 127.9, 124.1, 120.3, 60.4, 32.5, 26.3.

t-Butyl 2-diazopropanoate (5d)

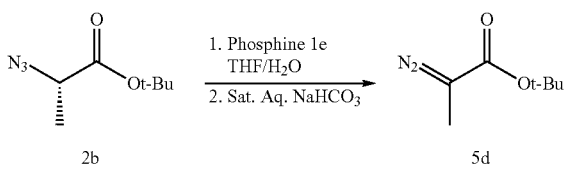

t-Butyl 2-azido propanoate (A. Tam, U. Arnold, M. B. Soellner, R. T. Raines, *J. Am. Chem. Soc.* 2007, 129, 12670-12671) 2d (66 mg, 0.386 mmol) was dissolved in THF/H$_2$O (2 mL/300 μL). To this solution was added phosphine 1e (144 mg, 0.405 mmol), and the resulting solution was stirred for 5 h under Ar(g). Sat. aq. NaHCO$_3$ (2 mL) was then added, and the mixture was stirred vigorously overnight. The mixture was then diluted with sat. aq. NaCl (15 mL) and extracted with CH$_2$Cl$_2$ (2×15 mL). The organic layers were combined, dried over Na$_2$SO$_4$(s), filtered, and evaporated under reduced pressure. The residue was purified by silica gel flash chromatography, eluting with CH$_2$Cl$_2$, to give the diazo-compound 5d as a yellow oil (45 mg, 0.290 mmol, 75% yield).

Data for 5d: $^1$H NMR (400 MHz, CDCl$_3$) δ=1.90 (s, 3H, CN$_2$CH$_3$), 1.47 (s, 9H, t-Bu). $^{13}$C NMR (100 MHz, CDCl$_3$, observed signals) δ=167.4, 81.0, 28.3, 8.4. HRMS (ESI+) m/z calculated for $(C_7H_{12}N_2O_2)^+$ 156.0894, measured 156.0896.

Methyl 3-(benzylsulfanyl)-2-diazopropanoate (5e)

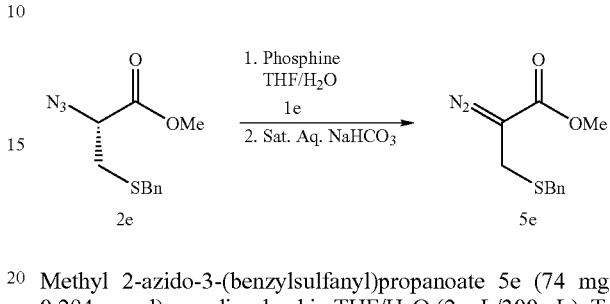

Methyl 2-azido-3-(benzylsulfanyl)propanoate 5e (74 mg, 0.294 mmol) was dissolved in THF/H$_2$O (2 mL/300 μL). To this solution was added phosphine 1e (110 mg, 0.309 mmol), and the resulting solution was stirred for 5 h under Ar(g). Sat. aq. NaHCO$_3$ (2 mL) was then added, and the mixture was stirred vigorously for 20 min. The mixture was then diluted with sat. aq. NaCl (15 mL) and extracted with CH$_2$Cl$_2$ (2×15 mL). The organic layers were combined, dried over Na$_2$SO$_4$(s), filtered, and evaporated under reduced pressure. The residue was purified by silica gel flash chromatography, eluting with CH$_2$Cl$_2$, to give the diazo-compound 5e as a yellow oil (67 mg, 0.285 mmol, 97% yield).

Data for 5e: $^1$H NMR (400 MHz, CDCl$_3$) δ=7.37-7.23 (m, 5H, Ar.), 3.78 (s, 2H, CH$_2$Ph), 3.77 (s, 3H, OCH$_3$), 3.45 (s, 2H, CN$_2$CH$_2$). $^{13}$C NMR (100 MHz, CDCl$_3$) δ=166.7, 137.7, 128.7, 128.5, 127.1, 56.7, 52.0, 36.0, 25.9. HRMS (ESI+) m/z calculated for $(C_{11}H_{12}N_2O_2SNa)^+$ 259.0506, measured 259.0506.

Methyl 6-{[(benzyloxy)carbonyl]amino}-2-diazohexanoate (5f)

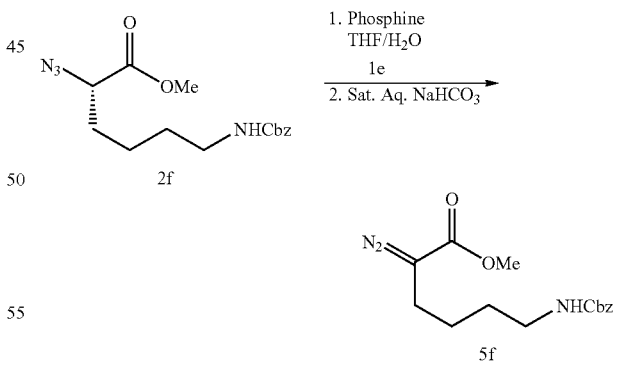

Methyl 2-azido-6-{[(benzyloxy)carbonyl]amino}hexanoate 2f (88 mg, 0.275 mmol) was dissolved in THF/H$_2$O (2 mL/300 μL). To this solution was added phosphine 1e (102 mg, 0.288 mmol), and the resulting solution was stirred for 5 h under Ar(g). Sat. aq. NaHCO$_3$ (2 mL) was then added, and the mixture was stirred vigorously overnight. The mixture was then diluted with sat. aq. NaCl (15 mL) and extracted with CH$_2$Cl$_2$ (2×15 mL). The organic layers were combined, dried over Na$_2$SO$_4$(s), filtered, and evaporated under reduced pressure. The residue was purified by silica gel flash chromatography, eluting with 20% EtOAc/hexanes, to give the diazo-compound 5f as a yellow oil (64 mg, 0.209 mmol, 76% yield).

Data for 5f: $^1$H NMR (400 MHz, CDCl$_3$, mixture of rotamers in ratio of 88:12) δ=7.42-7.31 (m, 5H, Ar.), 5.16 (s, 0.24H, CH$_2$Ph), 5.10 (s, 1.76H, CH$_2$Ph), 4.89 (br. s, 0.88H, NH), 4.70 (br. s, 0.12H, NH), 3.80-3.76 (m, 3H, OCH$_3$), 3.29-3.14 (m, 2H, CH$_2$NHCbz), 2.38-2.18 (m, 2H, CN$_2$CH$_2$), 1.62-1.49 (m, 4H, CN$_2$CH$_2$CH$_2$CH$_2$). $^{13}$C NMR (100 MHz, CDCl$_3$, signals corresponding to major rotamer) δ=167.9, 156.4, 136.4, 128.6, 128.2, 128.2, 66.7, 55.0, 52.0, 40.6, 29.1, 25.0, 22.9. HRMS (ESI$^+$) m/z calculated for (C$_{15}$H$_{19}$N$_3$O$_4$Na)$^+$ 328.1268, measured 328.1279.

3-Diazynylideneoxolan-2-one (5g)

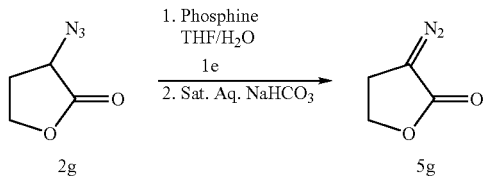

3-Azidooxolan-2-one 2g (69 mg, 0.545 mmol) was dissolved in THF/H$_2$O (2 mL/300 μL). To this was added phosphine 1e (203 mg, 0.572 mmol), and the resulting solution was stirred for 2 h under Ar(g). Sat. aq. NaHCO$_3$ (2 mL) was then added, and the mixture was stirred vigorously for 15 min. The mixture was then diluted with sat. aq. NaCl (15 mL) and extracted with CH$_2$Cl$_2$ (2×15 mL). The organic layers were combined, dried over Na$_2$SO$_4$(s), filtered, and evaporated under reduced pressure. The residue was purified by silica gel flash chromatography, eluting with CH$_2$Cl$_2$, to give the diazo-compound 5g as a yellow oil (57 mg, 0.507 mmol, 93% yield).

Data for 5g: $^1$H NMR (400 MHz, CDCl$_3$) δ=4.40 (t, 2H, J=7.8 Hz, OCH$_2$CH$_2$), 3.38 (t, 2H, J=7.8 Hz, OCH$_2$CH$_2$). $^{13}$C NMR (100 MHz, CDCl$_3$) δ=170.6, 65.3, 49.4, 23.1. HRMS (ESI$^+$) m/z calculated for (C$_4$H$_4$N$_2$O$_2$)$^+$ 112.0268, measured 112.0264.

2-Diazynylidenecyclohexan-1-one (5h)

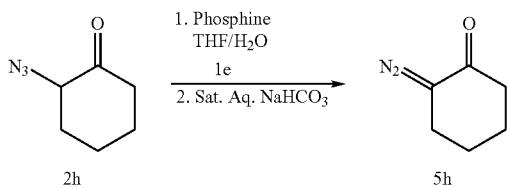

2-Azidocyclohexan-1-one 2h (62 mg, 0.442 mmol) was dissolved in THF/H$_2$O (2 mL/300 μL). To this was added phosphine 1e (165 mg, 0.465 mmol), and the resulting solution was stirred for 3 h under Ar(g). Sat. aq. NaHCO$_3$ (2 mL) was then added, and the mixture was stirred vigorously for 15 min. The mixture was then diluted with sat. aq. NaCl (15 mL) and extracted with CH$_2$Cl$_2$ (2×15 mL). The organic layers were combined, dried over Na$_2$SO$_4$(s), filtered, and evaporated under reduced pressure. The residue was purified by silica gel flash chromatography, eluting with 1% MeOH/CH$_2$Cl$_2$, to give the diazo-compound 5h as a yellow oil (37 mg, 0.296 mmol, 67% yield).

Data for 5 h: $^1$H NMR (400 MHz, CDCl$_3$) δ=2.73 (app. t, 2H, J=5.9 Hz), 2.36 (app. t, 2H, J=5.8 Hz), 1.86-1.74 (m, 4H). $^{13}$C NMR (100 MHz, CDCl$_3$) δ=194.3, 63.7, 37.3, 22.3, 22.3, 22.0. HRMS (ESI$^+$) m/z calculated for (C$_{12}$H$_{16}$N$_4$O$_2$Na, 2M+Na)$^+$ 271.1166, measured 271.1162.

2-Diazo-1-phenylethan-1-one (5i)

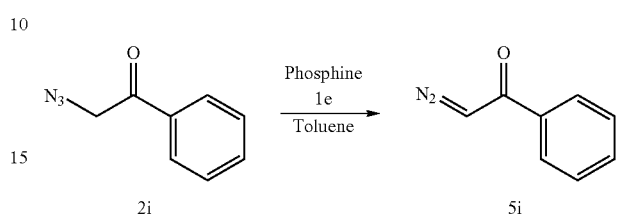

A solution of azide 2i (74 mg, 0.459 mmol) in anhydrous toluene (1.5 mL) was cooled to 0° C. A solution of phosphine 1e (171 mg, 0.482 mmol) in toluene (1.0 mL) was added dropwise. The resulting solution was maintained at 0° C. for 2 h and was then allowed to warm to room temperature. The mixture was then diluted with anhydrous CH$_2$Cl$_2$ (5 mL) and was stirred for an additional 30 min. The solution was then placed directly on a column of silica gel and eluted with 15% EtOAc/hexanes to give diazo-compound 5i as a yellow oil (33 mg, 0.226 mmol, 49% yield).

Data for 5i: $^1$H NMR (400 MHz, CDCl$_3$) δ=7.78 (d, 2H, J=7.7 Hz, Ar), 7.57 (t, 1H, J=7.4 Hz, Ar), 7.47 (app. t, 2H, J=7.4 Hz, Ar), 5.93 (s, 1H, CHN$_2$). $^{13}$C NMR (100 MHz, CDCl$_3$) δ=186.3, 136.6, 132.7, 128.6, 126.7, 54.1. HRMS (ESI$^+$) m/z calculated for (C$_8$H$_6$N$_2$ONa)$^+$ 169.0373, measured 169.0380.

9H-Fluoren-9-ylidenediazyne (5j)

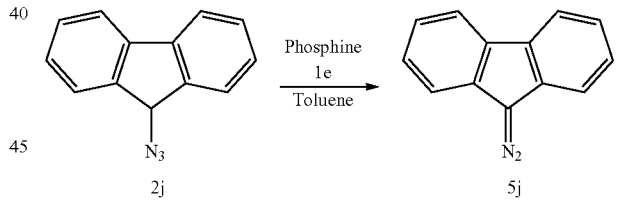

A solution of 9-azido-9H-fluorene 2j (62 mg, 0.303 mmol) in anhydrous toluene (1.5 mL) was placed under Ar(g) and cooled to 0° C. A solution of phosphine 1e in dry toluene (1 mL) was then added dropwise over 10 min whist maintaining the temperature at 0° C. The solution was then stirred for 5 h at 0° C. The solution was then allowed to warm to room temperature and stirred overnight. The resulting red solution (with white precipitate) was placed directly on a column of alumina (Basic, Grade 5) and eluted with hexanes to give diazo-compound 5j as a red solid (51 mg), which NMR analysis showed to be approximately 96% pure (the remainder being azide 2j), thus giving an 85% yield.

Data for 5j: $^1$H NMR (400 MHz, CDCl$_3$) δ=7.98 (d, 2H, J=7.5 Hz, Ar.), 7.54 (d, 2H, J=7.5 Hz, Ar.), 7.42 (t, 2H, J=7.5 Hz, Ar.), 7.36 (t, 2H, J=7.5 Hz, Ar.). $^{13}$C NMR (100 MHz, CDCl$_3$) δ=133.0, 131.4, 126.3, 124.5, 121.0, 119.3. 63.4. {Lit. $^1$H NMR (400 MHz, CDCl$_3$) δ=7.97 (ddd, 2H, J=7.6, 1.2, 0.8 Hz, Ar.), 7.53 (ddd, 2H, J=7.7, 1.2, 0.8 Hz, Ar.), 7.42 (td, 2H, J=7.4, 1.2 Hz, Ar.), 7.36 (td, 2H, J=7.5, 1.2 Hz, Ar.). $^{13}$C NMR (100 MHz, CDCl$_3$) δ=132.94, 131.41, 126.28, 124.48, 120.92, 119.27, 63.37. A. Levy, P. U. Biedermann, S. Cohen, I. Agranat, *J. Chem. Soc. Perkin. Trans.* 2, 2001, 2329-2341}

2-(Diazomethyl)-9,10-dihydroanthracene-9,10-dione (5k)

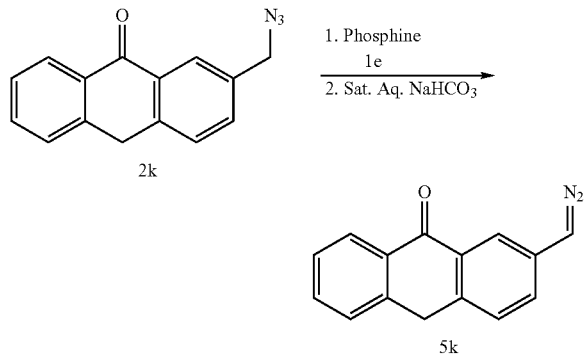

2-(Azidomethyl)-9,10-dihydroanthracene-9,10-dione 2k (78 mg, 0.296 mmol) was dissolved in THF/H$_2$O (1 mL/150 µL). To this was added phosphine 1e (116 mg, 0.326 mmol), and the resulting solution was stirred for 4 h under Ar(g). Sat. aq. NaHCO$_3$ (2 mL) was then added, and the mixture was stirred vigorously for 30 min. The mixture was then diluted with sat. aq. NaCl (15 mL) and extracted with CH$_2$Cl$_2$ (2×15 mL). The organic layers were combined, dried over Na$_2$SO$_4$(s), filtered, and evaporated under reduced pressure. The residue was purified by alumina (Basic-Grade 5) flash chromatography, eluting with 50% CH$_2$Cl$_2$/hexanes, to give 65 mg of an orange solid. The material was found to be 96% pure by NMR analysis (the remainder being the azide 2k), thus giving 85% yield of diazo-compound 5k.

Data for 5k: $^1$H NMR (400 MHz, CDCl$_3$) δ=8.36-8.27 (m, 2H, Ar.), 8.24 (d, 1H, J=8.2 Hz, Ar), 7.84-7.77 (m, 3H, Ar), 7.28 (s, 1H, Ar) 5.23 (s, 1H, CHN$_2$). $^{13}$C NMR (100 MHz, CDCl$_3$, observed signals) δ=183.2, 182.0, 138.3, 134.2, 133.7, 133.3, 129.1, 128.4, 127.1, 125.5, 118.8, 49.8. HRMS (ESI$^+$) m/z calculated for (C$_{15}$H$_8$N$_2$O$_2$)$^+$ 248.0581, measured 248.0588.

Example 5

Reaction of Phosphine 1a with Azide 2a

N-Benzyl-2-{[2-(diphenylphosphoryl)phenyl]formamido}acetamide 3

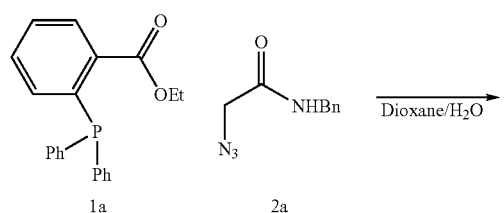

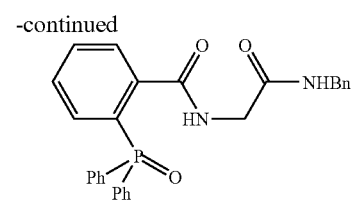

Azide 2a (36 mg, 0.188 mmol) was dissolved in 1,4-dioxane/H$_2$O (2 mL/4:1) and phosphine 1a (63 mg, 0.188 mmol) was added. The resulting solution was stirred for 5 h under Ar(g). The solution was diluted with sat. aq. NaCl (15 mL) and extracted with CH$_2$Cl$_2$ (2×15 mL). The organic layers were combined, dried over Na$_2$SO$_4$(s), filtered, and evaporated under reduced pressure. The residue was purified by silica gel flash chromatography, eluting with 2% MeOH/CH$_2$Cl$_2$, to give the amide 3 as a white solid (79 mg, 0.169 mmol, 90% yield).

Data for 3: $^1$H NMR (400 MHz, CDCl$_3$) δ=8.53 (br. s., 1H, NH), 7.71 (m, 1H, Ar.), 7.64-7.15 (m, 17H, Ar. and NH), 7.09 (dd, 1H, J=13.6, 7.7 Hz, Ar.), 4.45 (d, 2H, J=5.2 Hz, NHCH$_2$Ph), 3.90 (d, 1H, J=5.8 Hz, NHCH$_2$C(O)NHBn). $^{13}$C NMR (100 MHz, CDCl$_3$, $^{31}$P-coupled; $^1$H-decoupled, observed signals) δ=168.9, 141.0, 140.9, 138.8, 133.4, 133.3, 132.4, 132.4, 131.8, 131.7, 130.8, 130.0, 130.0, 129.9, 129.6, 129.5, 128.8, 128.7, 128.4, 127.8, 126.9, 44.2, 43.2. $^{31}$P NMR (162 MHz, CDCl$_3$) δ=34.3. HRMS (ESI$^+$) m/z calculated for (C$_{28}$H$_{25}$N$_2$O$_3$PNa)$^+$ 491.1496, measured 491.1516.

Example 6

Reaction of Phosphine 1b with Azide 2a

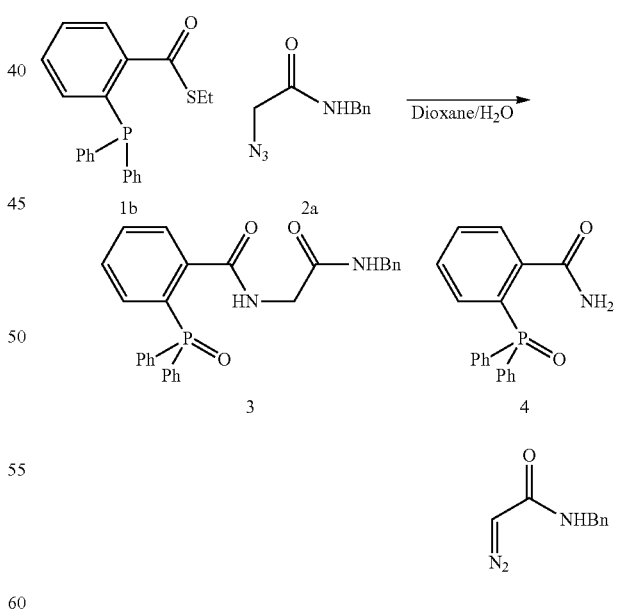

Azide 2a (36 mg, 0.188 mmol) was dissolved in 1,4-dioxane/H$_2$O (2 mL/4:1) and phosphine 1b (66 mg, 0.188 mmol) was added. The resulting solution was stirred for 2 days under Ar(g). The solution was diluted with sat. aq. NaCl (15 mL) and extracted with CH$_2$Cl$_2$ (2×15 mL). The organic layers were combined, dried over Na$_2$SO$_4$(s), filtered, and evaporated under reduced pressure. The residue was purified by silica gel flash chromatography, eluting with 30% EtOAc/hexanes and then 2% MeOH/CH$_2$Cl$_2$, to give diazo-compound 5a (10 mg, ~30% yield) as a yellow solid, and secondary amide 3 (53 mg, 60% yield) and primary amide 4 (20 mg, 33% yield) as white solids.

Data for 3 are as given above.

Data for 4: $^1$H NMR (400 MHz, CDCl$_3$) δ=8.99 (br. s, 1H, NH), 8.08 (m, 1H, Ar.), 7.72-7.38 (m, 12H, Ar.), 7.08 (dd, 1H, J=14.6, 7.1 Hz, Ar.), 5.58 (br. s, 1H, NH). $^{31}$P NMR (162 MHz, CDCl$_3$) δ=36.1. HRMS (ESI$^+$) m/z calculated for (C$_{19}$H$_{16}$NO$_2$PNa)$^+$ 344.0811, measured 344.0819.

Data for 5a are as given above.

Example 7

Reaction of Phosphine 1c with Aryl Azide 7: Triazene 8

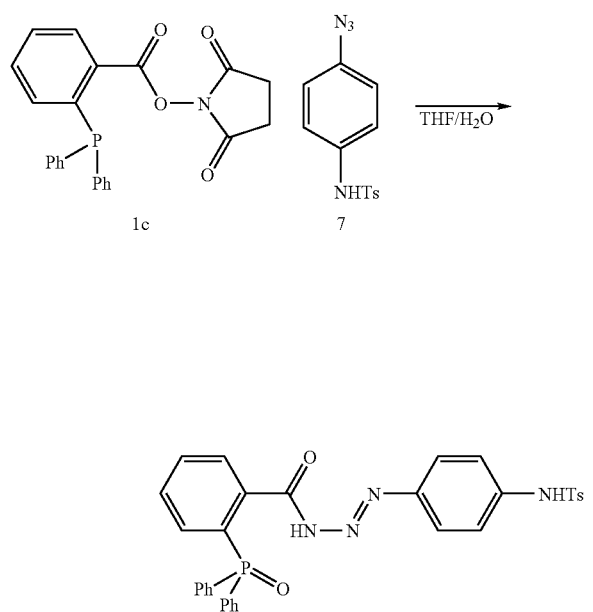

Aryl azide 7 (43 mg, 0.149 mmol) was dissolved in THF/H$_2$O (2 mL/300 μL). Phosphine 1c (63 mg, 0.156 mmol) was added, and the resulting solution was stirred overnight under Ar(g). The solution was diluted with sat. aq. NaCl (15 mL) and extracted with CH$_2$Cl$_2$ (2×15 mL). The organic layers were combined, dried over Na$_2$SO$_4$(s), filtered, and evaporated under reduced pressure. The residue was purified by silica gel flash chromatography, eluting with 2% MeOH/CH$_2$Cl$_2$ to give triazene 8 (85 mg, 0.143 mmol, 96% yield) as an off-white solid.

Data for 8: $^1$H NMR (400 MHz, CDCl$_3$, broad signals indicative of interconversion of isomers, most probably tautomers) δ=12.89 (br. s., 1H, NHNN), 8.59 (br. s, 1H, NHTs), 8.16 (br. s, 1H, Ar), 7.78-7.00 (m, 21H, Ar), 2.30 (br. s, 3H, CH$_3$). $^{13}$C NMR (100 MHz, CDCl$_3$, $^{31}$P-coupled; $^1$H-decoupled, observed signals) δ=143.6, 138.9, 136.4, 133.6, 133.5, 132.6, 132.0, 131.9, 130.9, 130.0, 129.5, 128.8, 128.7, 127.2, 21.5. $^{31}$P NMR (162 MHz, CDCl$_3$) δ=35.6. HRMS (ESI$^+$) m/z calculated for (C$_{32}$H$_{27}$N$_4$O$_4$PSNa)$^+$ 617.1383, measured 617.1360.

Example 8

Reaction of Phosphine 1e with Diazo-Compound 5a: Hydrazone 9

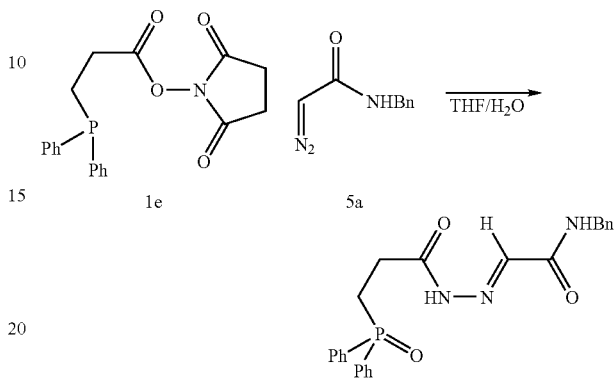

Diazo-compound 5a (50 mg, 0.286 mmol) was dissolved in THF/H$_2$O (2 mL/300 μL). Phosphine 1e (107 mg, 0.300 mmol) was added, and the resulting solution was stirred overnight under Ar(g). The solution was diluted with sat. aq. NaCl (15 mL) and extracted with CH$_2$Cl$_2$ (2×15 mL). The organic layers were combined, dried over Na$_2$SO$_4$(s), filtered, and evaporated under reduced pressure. The residue was purified by silica gel flash chromatography, eluting with 2% MeOH/CH$_2$Cl$_2$ to give acyl hydrazone 9 (118 mg, 95% yield) as a white solid.

Data for 9: $^1$H NMR (400 MHz, DMSO-d$_6$, mixture of isomers 1.6:1) δ=11.73 (s, 0.38H, CHCONHBn), 11.65 (s, 0.62H, CHCONHBn), 8.98 (t, 0.62H, J=5.8 Hz, NHBn), 8.75 (t, 0.38H, J=5.5 Hz, NHBn), 7.86-7.76 (m, 4H, Ar.), 7.60-7.45 (m, 6H, Ar.), 7.36-7.19 (m, 5H, Ar.), 4.41-4.34 (m, 2H, CH$_2$Ph), 2.78 (m, 1.24H, P(O)CH$_2$CH$_2$), 2.74-2.64 (m, 2H, P(O)CH$_2$CH$_2$), 2.42 (m, 0.76H, P(O)CH-$_2$CH$_2$). $^{13}$C NMR (100 MHz, CDCl$_3$, $^{31}$P-coupled; $^1$H-decoupled, observed signals, mixture of isomers) δ=175.5, 174.4, 174.3, 169.0, 168.8, 163.1, 163.0, 140.4, 137.9, 132.4, 132.4, 132.1, 131.5, 131.4, 130.7, 130.6, 130.5, 129.1, 129.0, 128.8, 128.7, 128.5, 127.7, 127.4, 127.2, 43.0, 26.9, 25.1, 25.0, 24.7, 24.2, 24.0. $^{31}$P NMR (162 MHz, CDCl$_3$) δ=35.3 (major isomer), 33.6 (minor isomer). HRMS (ESI$^+$) m/z calculated for (C$_{24}$H$_{26}$N$_3$O$_3$P)$^+$ 434.1629, measured 434.1613.

Example 9

Reaction of Phosphine 1e with Benzyl Azide: Triazene (10)

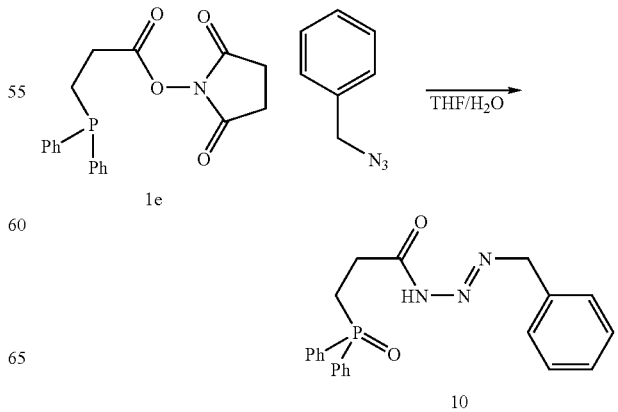

Benzyl azide (purchased from Frinton Laboratories, Inc.) (43 mg, 0.319 mmol) was dissolved in THF/H$_2$O (2 mL/300 µL). Phosphine 1e (119 mg, 0.335 mmol) was added, and the resulting solution was stirred overnight under Ar(g). The solution was diluted with sat. aq. NaCl (15 mL) and extracted with CH$_2$Cl$_2$ (2×15 mL). The organic layers were combined, dried over Na$_2$SO$_4$(s), filtered, and evaporated under reduced pressure. The residue was purified by silica gel flash chromatography, eluting with 2% MeOH/CH$_2$Cl$_2$ to give triazene 10 (100 mg, 0.255 mmol, 80% yield) as a white solid.

Data for 10: $^1$H NMR (400 MHz, CDCl$_3$, mixture of tautomers 1.5:1, broad signals) δ=12.89 (br. s, 0.4H, NHNN), 9.82 (br. s, 0.6H, NHNN), 7.84-7.22 (m, 15H, Ar.), 4.92 (br. s, 0.8H, CH$_2$Ph), 4.83 (br. s, 1.2H, CH$_2$Ph), 3.20-3.05 (m, 1.2H, P(O)CH$_2$CH$_2$), 2.90-2.50 (m, 2.8H, P(O)CH$_2$CH$_2$). $^{31}$P NMR (162 MHz, CDCl$_3$) δ=34.3 (minor tautomer), 33.1 (major tautomer). HRMS (ESI$^+$) m/z calculated for (C$_{22}$H$_{22}$N$_3$O$_2$P)$^+$ 391.1450, measured 391.1431.

Example 10

Benzyl 2-{[(t-butoxy)carbonyl]amino}-3-phenylpropanoate (12)

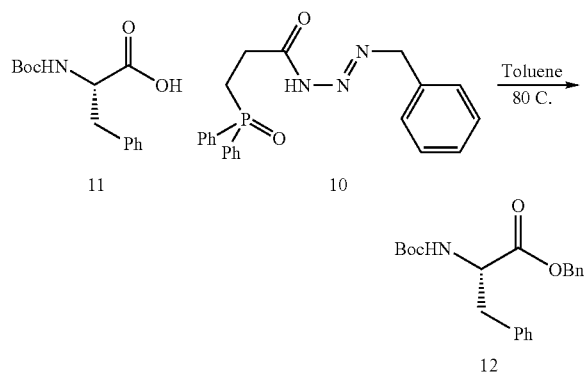

Carboxylic acid 11 (61 mg, 0.230 mmol) and acyl triazene 10 (90 mg, 0.230 mmol) were suspended in anhydrous toluene (2 mL). The mixture was warmed to 80° C., and the resulting solution was stirred at that temperature for 3 h. The resulting suspension was placed directly on a column of silica gel and eluted with 10% EtOAc/hexanes to give ester 12 as a waxy solid (41 mg, 0.116 mmol, 50% yield).

Data for 12: $^1$H NMR (400 MHz, CDCl$_3$) δ=7.43-7.21 (m, 8H, Ar), 7.11-7.03 (m, 2H, Ar), 5.19 (d, 1H, J=12.7 Hz, OCH$_2$Ph), 5.13 (d, 1H, J=12.7 Hz, OCH$_2$Ph), 5.00 (br. m, 1H, NHBoc), 4.65 (br. m, 1H, CHCH$_2$Ph), 3.16-3.05 (m, 2H, CHCH$_2$Ph), 1.43 (s, 9H, t-Bu). $^{13}$C NMR (100 MHz, CDCl$_3$, observed signals) δ=171.7, 155.0, 135.8, 135.2, 129.3, 128.5, 128.4, 127.0, 79.9, 67.1, 54.4, 38.3, 28.3. HRMS (ESI$^+$) m/z calculated for (C$_{21}$H$_{25}$NO$_4$)$^+$ 355.1779, measured 355.1776.

Example 11

Synthesis of Exemplary Water Soluble Phosphine Reagents

Certain phosphine reagents of the invention, such as those of formula V, can be prepared by adaptation of methods described in Tam and Raines 2009[23]. Scheme 8 illustrates a specific example of the synthesis of phosphine 15 and activated ester 15e.

In Scheme 8, 4-bromophenethyl alcohol is converted to the corresponding mesylate, and then to the corresponding amine, as indicated. Addition of its Grignard reagent to diethyl phosphite gives the corresponding phosphine oxide. The phosphine oxide is reduced by treatment with diisobutyl aluminum hydride (DIBAl-HX)[23]. As described in Example 2, the phosphine is reacted methyl acrylate and a few drops of benzyltrimethylammonium hydroxide (40 wt. % in MeOH) in CH$_3$CN under Ar(g). On completion of the reaction, the reaction mixture is concentrated under reduced pressure and the resulting residue is treated with KOH in aqueous methanol. The solution is diluted with H$_2$O, acidified to pH 2 with 2M HCl, extracted with CH$_2$Cl$_2$, dried and concentrated under reduced pressure. The resulting propanoic acid 15 can be further purified if desired. Compound 15 can be converted to a variety of activated esters. For example, compound 15 can be converted to the 2,5-dioxopyrrolidin-1-yl ester 15e as described in Example 2 by reaction with NHS in the presence to DIC.

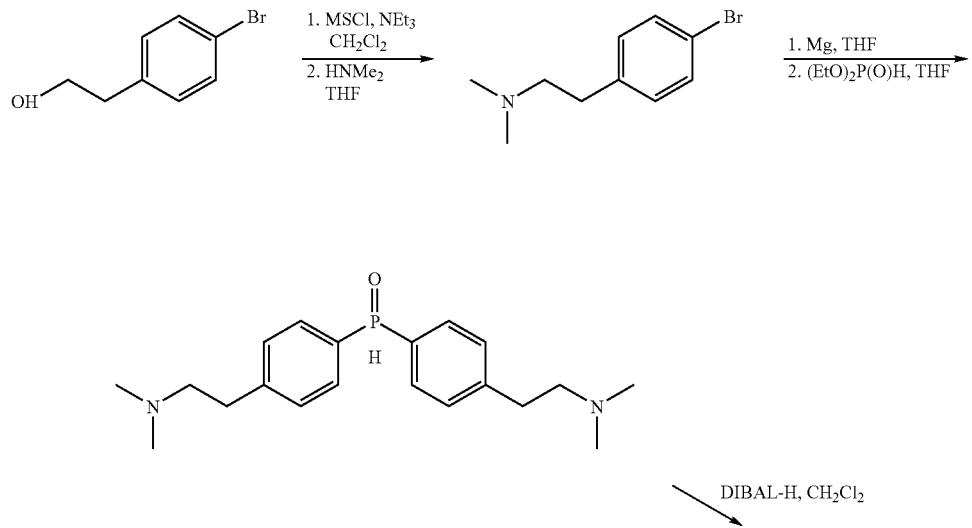

Scheme 8

-continued
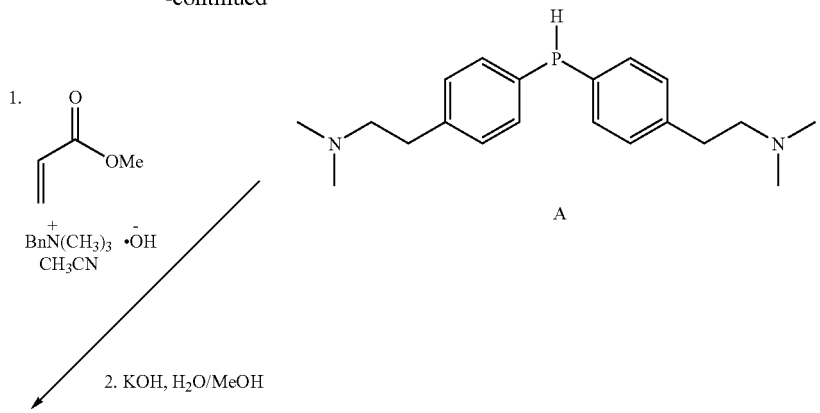
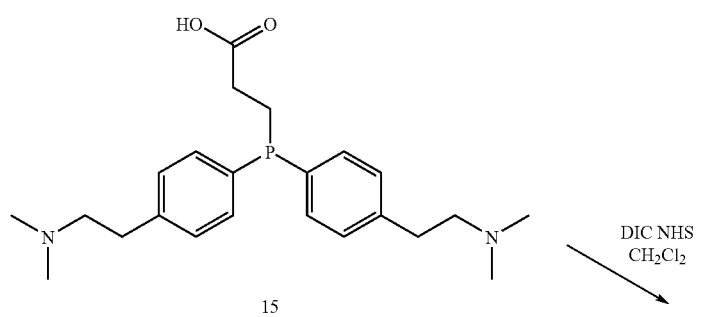
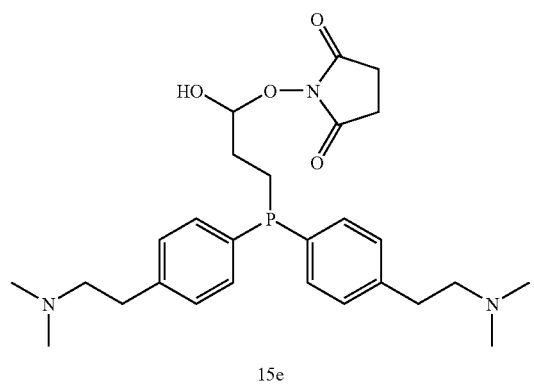

Scheme 9

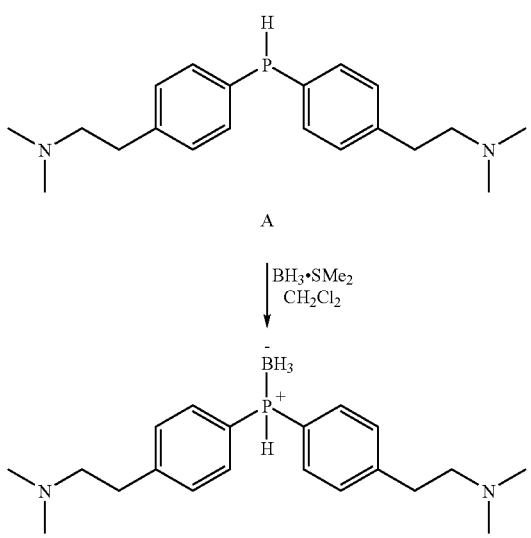

As illustrated in Scheme 9, a phosphine-borane complex can be prepared to facilitate storage of the phosphine A. The phosphine can be regenerated by reaction with diazabicyclo [2,2,2]-octane (DABCO) at reflux. Various compounds of the invention, particularly those in which $R^1$ and/or $R^2$ are groups of structure V can be prepared by the method of this example. More specifically, compounds of formulas VII-1, VII-2, or VII-3, where n is 1-6, 1-4 or 1-2 and w is 1-6, 1-4, or 1- and X, $R^5$, and $R_N$ are as defined herein, for example, can be prepared by the method of this example. Compounds of these formulas are water-soluble. Additionally, compounds of formulas VII-1, VII-2 and VII include water-soluble reagents

REFERENCES

[1] a) M. Regitz, G. Maas, *Diazo Compounds: Properties and Synthesis*, Academic Press, London, 1986, pp. 65-198; b) A. Padwa, M. D. Weingarten, *Chem. Rev.* 1996, 96, 223-269; c) M. P. Doyle, M. A. McKervey, T. Ye, *Modern Catalytic Methods for Organic Synthesis with Diazo Compounds*, John Wiley & Sons, New York, 1998; d) H. M. L. Davies, R. E. J. Beckwith, *Chem. Rev.* 2003, 103, 2861-2904; e) Z. Zhang, J. Wang, *Tetrahedron* 2008, 64, 6577-6605.

[2] Q. R. Bartz, C. C. Elder, R. P. Frohardt, S. A. Fusari, T. H. Haskell, D. W. Johannessen, A. Ryder, *Nature* 1954, 173, 72-73.

[3] a) S. Ito, T. Matsuya, S. Omura, M. Otani, A. Nakagawa, H. Takeshima, Y. Iwai, M. Ohtani, T. Hata, *J. Antibiot.* 1970, 23, 315-316; b) S. J. Gould, N. Tamayo, C. R. Melville, M. C. Cone, *J. Am. Chem. Soc.* 1994, 116, 2207-2208; c) S. Mithani, G. Weeratunga, N. J. Taylor, G. I. Dmitrienko, *J. Am. Chem. Soc.* 1994, 116, 2209-2210.

[4] H. He, W.-D. Ding, V. S. Bernan, A. D. Richardson, C. M. Ireland, M. Greenstein, G. A. Ellestad, G. T. Carter, *J. Am. Chem. Soc.* 2001, 123, 5362-5363.

[5] a) M. Regitz, *Angew. Chem.* 1967, 79, 786-801; *Angew. Chem. Int. Ed.* 1967, 6, 733-749; b) J. S. Baum, D. A. Shook, H. M. L. Davies, D. H. Smith, *Synth. Commun.* 1987, 17, 1709-1716.

[6] a) T. Curtius, *Ber,* 1883, 16, 2230-2231; b) E. C. Horning, *Org. Syn. Coll. Vol.* 3, Wiley, New York, 1955, p 392.

[7] a) W. R. Bamford, T. S. Stevens, *J. Chem. Soc.* 1952, 4735-4740; b) J. R. Fulton, V. K. Aggarwal, J. de Vicente, Eur. *J. Org. Chem.* 2005, 1479-1492.

[8] a) T. L. Holton, H. Shechter, *J. Org. Chem.* 1995, 60, 4725-4729; b) M. E. Furrow, A. G. Myers, *J. Am. Chem. Soc.* 2004, 126, 12222-12223.

[9] T. J. De Boer, H. J. Backer, *Org. Synth., Coll. Vol.* 1963, 4, 250-253.

[10] a) R. J. Baumgarten, *J. Org. Chem.* 1967, 32, 484-485; b) M. Schroen, S. Bräse, *Tetrahedron* 2005, 61, 12186-12192.

[11] a) T. Ye, M. A. McKervey, *Tetrahedron* 1992, 48, 8007-8022; b) Y. Zhao, J. Wang, *Synlett* 2005, 2886-2892; c) M. E. Meyer, E. M. Ferreira, B. M. Stoltz, *Chem. Commun.* 2006, 1316-1318; d) Y. Liu, Y. Zhang, N. Jee, M. P. Doyle, *Org. Lett.* 2008, 10, 1605-1608.

[12] D. B. Kimball, M. M. Haley, *Angew. Chem.* 2002, 114, 3484-3498; *Angew. Chem. Int. Ed.* 2002, 41, 3338-3351.

[13] a) H. Wamhoff, G. Richardt, S. Stölben, *Adv. Heterocycl. Chem.* 1995, 33, 159-249; b) P. M. Fresneda, P. Molina, *Syn. Lett.* 2004, 1197-1218.

[14] a) P. Molina, C. López-Leonardo, J. Llamas-Botía, C. Foces-Foces, C. Fernández-Castaño, *Tetrahedron* 1996, 52, 9629-9642; b) M. Mizuno, I. Muramoto, K. Kobayashi, H. Yaginuma, T. Inazu, *Synthesis* 1999, 162-165; c) M. D. Velasco, P. Molina, P. M. Fresneda, M. A. Sanz, *Tetrahedron* 2000, 56, 4079-4084; d) J. A. Restituyo, L. R. Comstock, S. G. Peterson, T. Stringfellow, S. R. Rajski, *Org. Lett.* 2003, 5, 4357-4360; e) X. Liu, N. Thirupathi, I. A. Guzei, J. G. Verkade, *Inorg. Chem.* 2004, 43, 7431-7440; f) A. Charafeddine, W. Dayoub, H. Chapuis, P. Strazewski, *Chem. Eur. J.* 2007, 13, 5566-5584.

[15] a) E. Saxon, C. R. Bertozzi, *Science* 2000, 287, 2007-2010; b) B. L. Nilsson; L. L. Kiessling; R. T. Raines, *Org. Lett.* 2000, 2, 1939-1941; c) M. Köhn, R. Breinbauer, *Angew. Chem.* 2004, 116, 3168-3178; *Angew. Chem. Int. Ed.* 2004, 43, 3106-3116.

[16] F. L. Lin, H. M. Hoyt, H. van Halbeek, R. G. Bergman, C. R. Bertozzi, *J. Am. Chem. Soc.* 2005, 127, 2686-2695.

[17] a) G. Oddo, A. Algerino, *Ber. Dtsch. Chem. Ges. B* 1936, 69B, 279-282; b) M. A. Kelly, M. Murray, M. L. Sinnott, *J. Chem. Soc., Perkin Trans.* 2 1982, 1649-1654.

[18] a) P. Krommes, J. Lorberth, *J. Organomet. Chem.* 1977, 127, 19-31; b) G. Wittig, W. Haag, *Chem. Ber.* 1955, 88, 1655-1666; c) H. Staudinger, J. Meyer, *Helv. Chim. Acta* 1919, 2, 619-635.

[19] a) J. L. Ozment, A. M. Schmeidekamp, L. A. Schultz-Merkel, R. H. Smith Jr., C. J. Michejda, *J. Am. Chem. Soc.* 1991, 113, 397-405; b) R. H. Smith Jr., B. D. Wladkowski, J. A. Herling, T. D. Pfaltzgraff, B. Pruski, J. Klose, C. J. Michejda, *J. Org. Chem.* 1992, 57, 654-661; c) S. Bräse, S. Dahmen, *Chem. Eur. J.* 2000, 6, 1899-1905; d) J. Rademann, J. Smerdka, G. Jung, P. Grosche, D. Schmid, *Angew. Chem.* 2001, 113, 390-394; *Angew. Chem. Int. Ed.* 2001, 40, 381-385.

[20] a) D. Y. Curtin, J. D. Druliner, *J. Org. Chem.* 1967, 32, 1552-1557; b) H. Lu, C. Li, *Tetrahedron Lett.* 2005, 46, 5983-5985.

[21] a) J. M. Antos, M. B. Francis, *J. Am. Chem. Soc.* 2004, 126, 10256-10257; b) A. Tam, M. B. Soellner, R. T. Raines, J. Am. Chem. Soc. 2007, 129, 11421-11430.

[22] a) S. T. Laughlin, N. J. Agard, J. M. Baskin, I. S. Carrico, P. V. Chang, A. S. Ganguli, M. J. Hangauer, A. Lo, J. A. Prescher, C. R. Bertozzi, *Methods Enzymol.* 2006, 415, 230-250. b) M. Francis in *Chemical Biology: From Small Molecules to Systems Biology and Drug Design* (Eds.: S. L. Schreiber, T. M. Kapoor, G. Wess), Wiley-VCH, Weinheim, 2007, pp 593-634.

[23] A. Tam and R. T. Raines Bioorg. Med. Chem. 2009, 17:1055-1063.

[24] Busacca, C. A.; Lorenz, J. C.; Grinberg, N.; Haddad, N.; Hrapchak, M.; Latli, B.; Lee, H.; Sabila, P.; Saha, A.; Sarvestani, M.; Shen, S.; Varsolona, R.; Wei, X. D. Senanayake, C. H. *Org. Lett.* 2005, 7, 4277-4280

We claim:

1. A method for making an acyl triazene, a diazo-compound or a diazonium salt thereof which comprises reacting a tertiary phosphine carrying an activated ester group with an azide; and isolating the acyl triazene or after optional thermal conversion or optional base conversion of the acyl triazene to the diazo-compound or diazonium salt thereof, isolating said diazo-compound or isolating or trapping said diazonium salt.

2. The method of claim of claim 1 wherein the tertiary phosphine is a compound of formula:

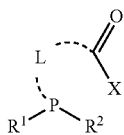

and salts thereof
wherein:

X is —$OR^5$ and —$COOR^5$ is an activated ester group;

$R^1$ and $R^2$, independently, are alkyl, alkenyl, alkynyl, aryl, alkylaryl, arylalkyl, heteroaryl, heterocyclic, —OR', —$N(R")_2$, —$P(R''')_{3-r}(OR')_r$, —$P(R''')_{3-r}(N(R")_2)_r$, or —$P(R''')_{3-s-t}(OR')_s(N(R")_2)_t$ groups, each of which is optionally substituted;

where r is 1-3, s and t are 1 or 2;

where each R' and R''', independently, is a hydrogen, alkyl, aryl, alkoxyalkyl, alkylaryl, arylalkyl, heteroaryl or heterocylic group;

each R" is a hydrogen, guanidine, alkyl, alkenyl, alkynyl, aryl, alkoxyalkyl, alkylaryl, arylalkyl, heteroaryl or heterocylic group; or two R" or R''' together form a 5- to 8-membered optionally substituted heterocyclic ring containing one or more heteroatoms, and optionally one or more —CO— groups; or $R^1$ and $R^2$ together form a 5- to 10-membered optionally substituted heterocyclic ring containing the phosphorous atom and optionally containing one or more additional heteroatoms, one or more —CO— groups or both; or one of $R^1$ or $R_2$ provides a linker to a solid surface; and L is a linking diradical which is an optionally substituted alkylene, arylene, heterocyclene, heteroarylene or combinations thereof; or L is a linking diradical which is an optionally substituted alkylene, arylene, heterocyclene, heteroarylene or combinations thereof wherein one or more of the —C—, —CH—, or —$CH_2$— moieties of the linker are optionally replaced with one or more —O—, —S—, —NR—, —CO—, —COO—, —CONR—, —CS—O—, or —NRCO—NR— moieties, where each R is a hydrogen, an alkyl group or an aryl group.

3. The method of claim 1 wherein the azide carries an electron withdrawing group.

4. The method of claim 3 wherein the azide has the formula:

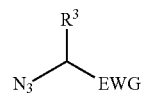

where EWG is an electron withdrawing group; and $R^3$ is hydrogen, or an optionally substituted alkyl, alkenyl, alkynyl, aryl, heteroaryl, heterocyclic group or an electron withdrawing group or $R^3$ and EWG together form an optionally substituted carbocyclic or heterocylic ring.

5. The method of claim 3 wherein $R^3$ is an electron withdrawing group or is an alkyl, alkenyl, alkynyl, aryl, heteroaryl, or heterocyclic group substituted with an electron withdrawing group that is the same or different from EWG.

6. The method of claim 1 wherein the azide is an azidosugar.

7. The method of claim 6 wherein the azidosugar is immobilized in a cell or on a cell surface.

8. The method of claim 2 wherein the tertiary phosphine is immobilized on a solid.

9. The method of claim 1 which is carried out in the presence of water, in a wet organic solvent or in aqueous medium.

10. The method of claim 1 wherein the tertiary phosphine reagent is, at least in part, water soluble and the reaction is carried out in aqueous medium.

11. The method of claim 1 wherein the diazo-compound is the predominant reaction product.

12. The method of claim 11 wherein acyl triazene formed in the reaction is converted to the diazo-compound or diazonium salt thereof thermally or by addition of base.

13. The method of claim 1 wherein the acyl triazene is the predominant reaction product.

14. The method of claim 1 wherein the tertiary phosphine is a compound of formula I-1, I-2 V-3 or V-4:

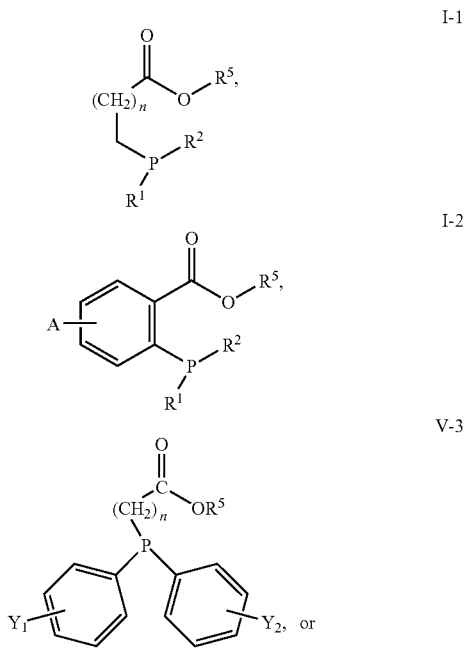

-continued

V-4

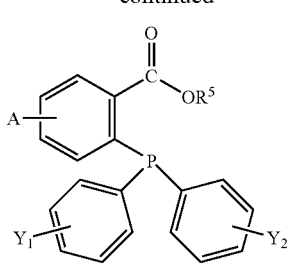

where n is an integer ranging from 1-5 inclusive;
A represents one to five optional non-hydrogen substituents on the ring;
—CO—OR⁵ is an activated ester group;
$R^1$ and $R^2$, independently, are alkyl, alkenyl, alkynyl, aryl, alkylaryl, arylalkyl, heteroaryl, heterocyclic, —OR', or —N(R")₂ groups, each of which is optionally substituted; where each R' and R", independently, is a hydrogen, guanidine, alkyl, alkenyl, alkynyl, aryl, alkoxyalkyl, alkylaryl, arylalkyl, heteroaryl or heterocylic group, or two R" together form a 5- to 8-membered optionally substituted heterocyclic ring containing the nitrogen atom and optionally containing one or more additional heteroatoms, one or more —CO— groups or both; one of $R^1$ or $R^2$ is a linker to a solid surface; or $R^1$ and $R^2$ together form a 5- to 10-membered optionally substituted heterocyclic ring containing the phosphorous atom and optionally containing one or more additional heteroatoms, one or more —CO— groups or both; and
$Y_1$ and $Y_2$ represent one or more non-hydrogen substituents on the indicated phenyl ring, wherein each $Y_1$ substituent and each $Y_2$ substituent is, independently, halogen, —OH, —N(R_N)₂, an alkoxyalkyl group or an alkyl group, each of which is optionally substituted with one or more —OH, —N(R_N)₂, —COOH, or —COOR_C groups, where each R_N is, independently, hydrogen, an alkyl, an alkenyl, an alkynyl, an aryl, an arylalkyl, an alkylaryl group or a guanidine, and Rc is an optionally substituted alkyl, aryl, arylalkyl or alkylaryl group or two R_N are linked together to form a 5-8-membered ring which contains the nitrogen atom and optionally contains one or more additional heteroatoms, one or more —CO— groups, or both; and wherein substitution of any optionally substituted group or ring is substitution with one or more halogens, hydroxyl, nitro, cyano, isocyano, thiocyano, isothiocyano, —SO₃R, —N(R)₂, —COR, —COOR, —CON(R)₂, —NR—CO—N(R)₂, —CO—SR, —OR, or —SR, where each R, independently, is hydrogen, alkyl, halogenated alkyl, alkenyl, alkynyl, aryl, halogenated aryl, heteroaryl, or heterocyclic groups.

15. The method of claim 14 wherein —OR⁵ is:
(1) a —ON(R⁷)₂ group, a —O—NR⁷—CO—R⁷ group or a —O—N(COR⁷)—COR⁷, where each R⁷ is an optionally substituted alkyl or aryl group, or where the two R⁷ groups together form an optionally substituted 5-8-membered heterocyclic ring having one or more heteroatoms and optionally one or more —CO— groups in the ring;
(2) a phenyloxy group substituted with one or more halogens, hydroxyl, nitro, alkyl, alkenyl, alkynyl, aryl, halogenated alkyl, hydroxyl-substituted alkyl, amino-substituted alkyl, cyano, isocyano, thiocyano, isothiocyano, —SO₃R, —N(R)₂, —COR, —COOR, —CON(R)₂, —NR—CO—N(R)₂, —CO—SR, —OR, or —SR, where each R, independently, is hydrogen, alkyl, halogenated alkyl, alkenyl, alkynyl, aryl, halogenated aryl, heteroaryl, or heterocyclic groups, or two R together form a 5- to 8-membered optionally substituted heterocyclic ring containing one or more heteroatoms, and optionally one or more —CO— groups;
(3) —O—R⁵ where R⁵ is an optionally substituted heterocylic or heteroaromatic group; or
(4) —O—SO₂—O-Rs where Rs is halogen, optionally substituted alkyl, optionally substituted aryl, optionally substituted phenyl, halogenated alkyl, halogenated aryl, halogenated phenyl, fluorinated alkyl, fluorinated aryl, fluorinated phenyl, unsubstituted alkyl, unsubstituted phenyl, methyl, ethyl, —CF₃, or —C₄F₉.

16. The method of claim 14 wherein R⁵ is pentafluorophenyl, difluorophenyl, trifluorophenyl, 4-nitrophenyl, 3-dialkyl aminophenyl, 3-dimethylaminophenyl, 3-diethylaminophenyl, 3-pyridinyl, 2, 5-dioxo pyrrolidinyl, 2-oxopyrrolidinyl, 2, 6-dioxopiperidinyl, 1-piperazinyl, 1-piperidinyl, or 1-pyrrolidinyl.

17. The method of claim 14 wherein one or both of $R^1$ and $R^2$ are independently

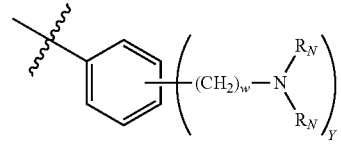

or protonated or quaternary ions or salts thereof;
wherein:
w is an integer ranging from 1-6,
Y is 1 or 2 and each $R_N$ is, independently, hydrogen, an alkyl, an alkenyl, an alkynyl, an aryl, an arylalkyl, an alkylaryl group or a guanidine, or two $R_N$ are linked together to form a 5- to 8-membered ring which contains the nitrogen atom and optionally contains one or more additional heteroatoms, one or more —CO— groups or both.

18. The method of claim 17 wherein —OR⁵ is:
(1) a phenyloxy group substituted with one or more halogens, hydroxyl, nitro, alkyl, alkenyl, alkynyl, aryl, halogenated alkyl, hydroxyl-substituted alkyl, amino-substituted alkyl, cyano, isocyano, thiocyano, isothiocyano, —SO₃R, —N(R)₂, —COR, —COOR, —CON(R)₂, —NR—CO—N(R)₂, —CO—SR, —OR, or —SR, groups, where each R, independently, is hydrogen, alkyl, halogenated alkyl, alkenyl, alkynyl, aryl, halogenated aryl, heteroaryl, or heterocyclic groups, or two R together form a 5- to 8-membered optionally substituted heterocyclic ring containing one or more heteroatoms, optionally one or more —CO— groups or both;
(2) —O—R⁵ where R⁵ is an optionally substituted heterocylic or heteroaromatic group; or
(3) —O—SO₂—O-Rs where Rs is halogen, optionally substituted alkyl, optionally substituted aryl, optionally substituted phenyl, halogenated alkyl, halogenated aryl, halogenated phenyl, fluorinated alkyl, fluorinated aryl, fluorinated phenyl, unsubstituted alkyl, unsubstituted phenyl, methyl, ethyl, —CF₃, or —C₄F₉.

19. The method of claim 1 wherein the activated ester is —COOR⁵ and —OR⁵ is:
(1) a phenyloxy group substituted with one or more halogens, hydroxyl, nitro, alkyl, alkenyl, alkynyl, aryl, halogenated alkyl, hydroxyl-substituted alkyl, amino-substituted alkyl, cyano, isocyano, thiocyano, isothiocyano, —SO₃R,—N(R)₂, —COR, —COOR, —CON(R)₂, —NR—CO—N(R)₂, —CO—SR, —OR, or —SR groups, where each R, independently, is hydrogen, alkyl, halogenated alkyl, alkenyl, alkynyl, aryl, halogenated aryl, heteroaryl, or heterocyclic groups, or two R together form a 5- to 8-membered optionally substituted heterocyclic ring containing one or more heteroatoms, optionally one or more —CO— groups or both;
(2) —O—R⁵ where R⁵ is an optionally substituted heterocylic or heteroaromatic group; or
(3) —O—SO₂—O-Rs where Rs is halogen, optionally substituted alkyl, optionally substituted aryl, optionally substituted phenyl, halogenated alkyl, halogenated aryl, halogenated phenyl, fluorinated alkyl, fluorinated aryl, fluorinated phenyl, unsubstituted alkyl, unsubstituted phenyl, methyl, ethyl, —CF₃, or —C₄F₉.

20. The method of claim 1 wherein the activated ester is —COOR⁵ and R⁵ is pentafluorophenyl, difluorophenyl, trifluorophenyl, 4-nitrophenyl, 3-dialkyl aminophenyl, 3-dimethylaminophenyl, 3-diethylaminophenyl, 3-pyridinyl, 2,5-dioxo pyrrolidinyl, 2-oxopyrrolidinyl, 2, 6-dioxopiperidinyl, 1-piperazinyl, 1-piperidinyl, or 1-pyrrolidinyl.

21. The method of claim 2 wherein —OR⁵ is:
(1) a phenyloxy group substituted with one or more halogens, hydroxyl, nitro, alkyl, alkenyl, alkynyl, aryl, halogenated alkyl, hydroxyl-substituted alkyl, amino-substituted alkyl, cyano, isocyano, thiocyano, isothiocyano, —SO₃R,—N(R)₂, —COR, —COOR, —CON(R)₂, —NR—CO—N(R)₂, —CO—SR, —OR, or —SR groups, where each R, independently, is hydrogen, alkyl, halogenated alkyl, alkenyl, alkynyl, aryl, halogenated aryl, heteroaryl, or heterocyclic groups, or two R together form a 5- to 8-membered optionally substituted heterocyclic ring containing one or more heteroatoms, optionally one or more —CO— groups or both;
(2) —O—R⁵ where R⁵ is an optionally substituted heterocylic or heteroaromatic group; or
(3) —O—SO₂—O-Rs where Rs is halogen, optionally substituted alkyl, optionally substituted aryl, optionally substituted phenyl, halogenated alkyl, halogenated aryl, halogenated phenyl, fluorinated alkyl, fluorinated aryl, fluorinated phenyl, unsubstituted alkyl, unsubstituted phenyl, methyl, ethyl, —CF₃, or —C₄F₉.

22. The method of claim 2 wherein the azide has the formula:

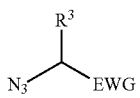

where EWG is an electron withdrawing group; and R³ is hydrogen, or an optionally substituted alkyl, alkenyl, alkynyl, aryl, heteroaryl, heterocyclic group or an electron withdrawing group or wherein R³ and EWG together form an optionally substituted carbocyclic or heterocylic ring.

23. A method for making an acyl triazene, a diazo-compound or a diazonium salt thereof which comprises reacting a tertiary phosphine with an azide to form the acyl triazene or the diazo-compound or diazonium salt thereof after optional thermal conversion or optional base conversion of the acyl triazene, wherein:

(a) the tertiary phosphine has formula:

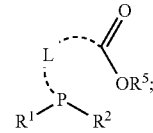

(b) the azide has formula:

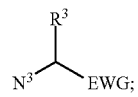

(c) the acyl triazene has formula:

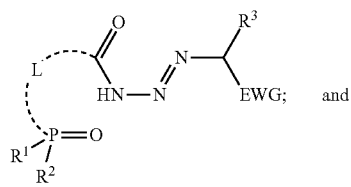

(d) the diazo-compound has formula:

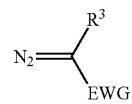

where:

—COOR⁵ is an activated ester group;

R¹ and R², independently, are alkyl, alkenyl, alkynyl, aryl, alkylaryl, arylalkyl, heteroaryl, heterocyclic, —OR', —N(R")₂, —P(R''')₃₋ᵣ(OR')ᵣ, —P(R''')₃₋ᵣ(N(R")₂)ᵣ, or —P(R''')₃₋ₛ₋ₜ(OR')ₛ(N(R")₂)ₜ groups, each of which is optionally substituted, where r is 1-3;

s and t are 1 or 2;

each R' and R''', independently, is a hydrogen, alkyl, aryl, alkoxyalkyl, alkylaryl, arylalkyl, heteroaryl or heterocylic group;

each R" is a hydrogen, guanidine, alkyl, alkenyl, alkynyl, aryl, alkoxyalkyl, alkylaryl, arylalkyl, heteroaryl or heterocyclic group; or two R" or R''' together with the heteroatom to which they are attached form a 5- to 8-membered optionally substituted heterocyclic ring containing one or more heteroatoms, and optionally one or more —CO— groups;

R¹ and R² together with the phosphorous to which they are attached form a 5- to 10-membered optionally substituted heterocyclic ring optionally containing one or more additional heteroatoms, one or more —CO— groups or both; or one of $R^1$ or $R^2$ provides a linker to a solid surface;

L is a linking diradical which is an optionally substituted alkylene, arylene, heterocyclene, heteroarylene or combinations thereof; or L is a linking diradical which is an optionally substituted alkylene, arylene, heterocyclene, heteroarylene or combinations thereof wherein one or more of the —C—, —CH—, or —CH$_2$— moieties of the linker are optionally replaced with one or more —O—, —S—, —NR—, —CO—, —COO—, —CONR—, —CS—O—, or —NRCO—NR— moieties, where each R is a hydrogen, an alkyl group or an aryl group;

EWG is an electron withdrawing group; and $R^3$ is hydrogen, or an optionally substituted alkyl, alkenyl, alkynyl, aryl, heteroaryl, heterocyclic group or an electron withdrawing group; or $R^3$ and EWG together form an optionally substituted carbocyclic or heterocylic ring.

* * * * *